(12) United States Patent
Hatakeyama et al.

(10) Patent No.: US 11,163,232 B2
(45) Date of Patent: *Nov. 2, 2021

(54) RESIST COMPOSITION, PATTERNING PROCESS, AND BARIUM SALT

(71) Applicant: Shin-Etsu Chemical Co., Ltd., Tokyo (JP)

(72) Inventors: Jun Hatakeyama, Joetsu (JP); Takeshi Sasami, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 114 days.

This patent is subject to a terminal disclaimer.

(21) Appl. No.: 16/161,459

(22) Filed: Oct. 16, 2018

(65) Prior Publication Data

US 2019/0113846 A1 Apr. 18, 2019

(30) Foreign Application Priority Data

Oct. 18, 2017 (JP) .............................. JP2017-201726

(51) Int. Cl.
| | | |
|---|---|---|
| G03F 7/004 | (2006.01) | |
| G03F 7/30 | (2006.01) | |
| C07C 303/32 | (2006.01) | |
| C07C 309/06 | (2006.01) | |
| C07C 309/07 | (2006.01) | |
| C07C 309/09 | (2006.01) | |
| C07C 309/12 | (2006.01) | |
| C07C 309/24 | (2006.01) | |
| G03F 7/039 | (2006.01) | |
| G03F 7/20 | (2006.01) | |
| G03F 7/38 | (2006.01) | |

(52) U.S. Cl.
CPC .......... *G03F 7/0045* (2013.01); *C07C 303/32* (2013.01); *C07C 309/06* (2013.01); *C07C 309/07* (2013.01); *C07C 309/09* (2013.01); *C07C 309/12* (2013.01); *C07C 309/24* (2013.01); *G03F 7/0046* (2013.01); *G03F 7/0048* (2013.01); *G03F 7/0392* (2013.01); *G03F 7/0397* (2013.01); *G03F 7/38* (2013.01); *G03F 7/70625* (2013.01)

(58) Field of Classification Search
CPC .... G03F 7/0045; G03F 7/0392; G03F 7/0397; C07C 303/32; C07C 309/06; C07C 309/07; C07C 309/09; C07C 309/12; C07C 309/24

See application file for complete search history.

(56) References Cited

U.S. PATENT DOCUMENTS

| | | | | |
|---|---|---|---|---|
| 7,875,417 B2* | 1/2011 | Ogihara | .................. | C08L 83/04 |
| | | | | 430/270.1 |
| 8,283,104 B2* | 10/2012 | Ohashi | ..................... | G03F 1/50 |
| | | | | 430/270.1 |
| 9,360,753 B2 | 6/2016 | Hatakeyama | | |
| 10,078,264 B2* | 9/2018 | Hatakeyama | ......... | C07C 309/06 |
| 2017/0115566 A1 | 4/2017 | Hatakeyama et al. | | |

FOREIGN PATENT DOCUMENTS

| | | |
|---|---|---|
| JP | 2006-178317 A | 7/2006 |
| JP | 2010-152136 A | 7/2010 |
| JP | 2013-025211 A | 2/2013 |
| KR | 10-2017-0048175 A | 5/2017 |

OTHER PUBLICATIONS

Office Action dated Mar. 4, 2020, issued in counterpart TW Application No. 107136120. (5 pages).

Hinsberg et al., "Extendibility of Chemically Amplified Resists : Another Brick Wall?", SPIE, 2003, vol. 5039, pp. 1-14, cited in Specification (14 pages).

Kishikawa et al., "Assessment of trade-off between resist resolution and sensitivity for optimization of hyper-NA immersion lithography" SPIE, 2007, vol. 6520, pp. 65203L-1-65203L-9, cited in Specification (9 pages).

Office Action dated Feb. 13, 2020, issued in counterpart KR Application No. 10-2018-0123148, with English Translation. (12 pages).

\* cited by examiner

*Primary Examiner* — John S Chu

(74) *Attorney, Agent, or Firm* — Westerman, Hattori, Daniels & Adrian, LLP

(57) ABSTRACT

A resist composition comprising a base resin comprising recurring units having an acid labile group, and a metal salt of sulfonic acid exhibits a high sensitivity and high resolution, and forms a pattern of satisfactory profile with minimal LWR or improved CDU when processed by lithography.

14 Claims, No Drawings

RESIST COMPOSITION, PATTERNING PROCESS, AND BARIUM SALT

CROSS-REFERENCE TO RELATED APPLICATION

This non-provisional application claims priority under 35 U.S.C. § 119(a) on Patent Application No. 2017-201726 filed in Japan on Oct. 18, 2017, the entire contents of which are hereby incorporated by reference.

TECHNICAL FIELD

This invention relates to a resist composition, a patterning process using the same, and a barium salt.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of 13.5 nm wavelength, and double patterning version of the ArF lithography, on which active research efforts have been made.

The current technology is approaching to the processing size which is reduced below 50 nm as minimum line width. When the processing size is so reduced, the thickness of resist film must be reduced below 100 nm, depending on the surface material of the substrate to be processed, because of such factors as the structural strength to maintain the pattern against the surface tension of developer and the adhesion strength to the substrate. On use of prior art chemically amplified resist materials intended to form high-resolution resist film, for example, based on a base resin having an acetal protective group, no significant degradation of line edge roughness (LER) does occur with a resist film having a thickness of 150 nm, but LER is substantially exacerbated when the film thickness is reduced below 100 nm.

With respect to high-energy radiation of very short wavelength such as EB or x-ray, hydrocarbons used in resist materials have little absorption. Then hydrocarbon (typically polyhydroxystyrene) base resist materials are under consideration. Resist materials for EB lithography are practically used in the mask image writing application. Recently, the mask manufacturing technology becomes of greater interest. Reduction projection exposure systems or steppers have been used since the time when the exposure light was g-line. While their demagnification factor was ⅕, a factor of ¼ is now used as a result of chip size enlargement and projection lens diameter increase. It becomes of concern that a dimensional error of a mask has an impact on the dimensional variation of a pattern on wafer. It is pointed out that as the pattern feature is reduced, the value of a dimensional variation on the wafer becomes greater than the value of a dimensional error of the mask. This is evaluated by a mask error enhancement factor (MEEF) which is a dimensional variation on wafer divided by a dimensional error of mask. Patterns on the order of 45 nm often show an MEEF in excess of 4. In a situation including a demagnification factor of ¼ and a MEEF of 4, the mask manufacture needs an accuracy substantially equivalent to that for equi-magnification masks.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage increased from 10 kV to 30 kV and reached 50 kV in the current mainstream system, with a voltage of 100 kV being under investigation.

As the accelerating voltage increases, a lowering of sensitivity of resist film becomes of concern. As the accelerating voltage increases, the influence of forward scattering in a resist film becomes so reduced that the contrast of electron image writing energy is improved to ameliorate resolution and dimensional control whereas electrons can pass straightforward through the resist film so that the resist film lowers its sensitivity.

Since the mask exposure tool is designed for exposure by direct continuous writing, a lowering of sensitivity of resist film leads to an undesirably reduced throughput. Due to a need for higher sensitivity, chemically amplified resist compositions are contemplated.

As the feature size is reduced, image blurs due to acid diffusion become a problem (see Non-Patent Document 1). To insure resolution for fine patterns with a size of 45 nm et seq., not only an improvement in dissolution contrast is requisite, but control of acid diffusion is also important (see Non-Patent Document 2). Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast.

Addition of an acid generator capable of generating a bulky acid is effective for suppressing acid diffusion. It is then proposed to incorporate in a polymer recurring units derived from an onium salt having a polymerizable unsaturated bond serving as acid generator. Sulfonium and iodonium salts having a polymerizable unsaturated bond capable of generating a sulfonic acid are proposed in Patent Document 1 and other documents. Patent Document 1 also discloses a sulfonium or iodonium salt having sulfonic acid directly attached to the backbone.

It was avoided to use metal-containing materials as the lithography resist material for the semiconductor device fabrication because of a possible malfunction of semiconductor devices. However, it is known in the application other than the semiconductor, for example, as the resist material for forming color filters for LCD, to use a metal-containing (meth)acrylate as a copolymerizable monomer.

Patent Document 2 discloses EB resist and antistatic film having alkali metal and alkaline earth metal salts added thereto. These salts improve the sensitivity on EB exposure at no sacrifice of resolution. Patent Document 3 discloses a chemically amplified resist composition having a metal salt of carboxylic acid or β-diketone added thereto. The metal salt of carboxylic acid or β-diketone functions as a quencher through its ion exchange with a sulfonic acid generated from the acid generator.

CITATION LIST

Patent Document 1: JP-A 2006-178317
Patent Document 2: JP-A 2010-152136
Patent Document 3: JP-A 2013-025211 (U.S. Pat. No. 9,360,753)
Non-Patent Document 1: SPIE Vol. 5039 p1 (2003)
Non-Patent Document 2: SPIE Vol. 6520 p65203L-1 (2007)

DISCLOSURE OF INVENTION

While the miniaturization of the pattern rule is in progress to meet the demand for higher integration density and operating speed of LSIs as alluded to previously, there is a need for a resist composition which has a high sensitivity despite a high resolution and forms a pattern of satisfactory profile with a minimal LWR or improved CDU after exposure and development.

An object of the invention is to provide a resist composition which has both high resolution and sensitivity and forms a pattern with a satisfactory profile and minimal LWR or improved CDU after exposure and development, a patterning process using the resist composition, and a novel barium salt useful in the resist composition.

The inventors have found that a resist composition comprising a base resin comprising recurring units having an acid labile group and a sodium, magnesium, potassium, calcium, rubidium, strontium, yttrium, cesium, barium or cerium salt of fluorosulfonic acid having a benzene ring substituted with a plurality of iodine or bromine atoms exhibits a high sensitivity, forms a pattern of satisfactory profile with minimal LER or improved CDU after exposure and development, and is effective for preventing electrostatic charges during EB image writing. The resist composition is thus suited as the micropatterning material for the fabrication of VLSIs and photomasks.

In one aspect, the invention provides a resist composition comprising a base resin comprising recurring units having an acid labile group, and a metal salt of sulfonic acid having the formula (1).

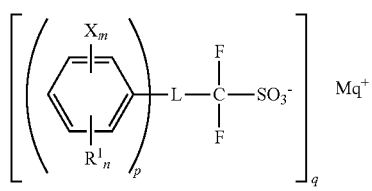
(1)

Herein X is each independently iodine or bromine; R1 is hydroxy, $C_1$-$C_{20}$ alkyl, $C_1$-$C_{20}$ alkoxy, $C_2$-$C_{20}$ acyloxy, fluorine, chlorine, amino, —$NR^2$—$C(=O)$—$R^3$, or —$NR^2$—$C(=O)$—$O$—$R^3$, at least one hydrogen on the alkyl, alkoxy or acyloxy group may be substituted by fluorine, chlorine, bromine, iodine, hydroxyl, amino or a $C_1$-$C_6$ alkoxy moiety; $R^2$ is a $C_1$-$C_6$ alkyl group; $R^3$ is a $C_1$-$C_{16}$ alkyl, $C_2$-$C_{16}$ alkenyl or $C_6$-$C_{12}$ aryl group in which at least one hydrogen may be substituted by a halogen, hydroxyl, $C_1$-$C_6$ alkoxy, $C_2$-$C_6$ acyl or $C_2$-$C_6$ acyloxy moiety; L is a single bond or a (p+1)-valent $C_1$-$C_{20}$ hydrocarbon group which may contain an ether bond, carbonyl, ester bond, amide bond, sultone, lactam, carbonate, halogen, hydroxyl or carboxyl moiety; $M^{q+}$ is a sodium, magnesium, potassium, calcium, rubidium, strontium, yttrium, cesium, barium or cerium ion; m is an integer of 2 to 5, n is an integer of 0 to 3, m+n is 2 to 5, p is an integer of 1 to 3, and q is an integer of 1 to 3.

In a preferred embodiment, the recurring units having an acid labile group have the formula (a1) or (a2).

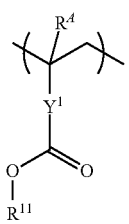
(a1)

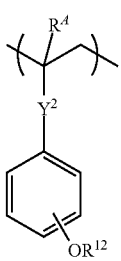
(a2)

Herein $R^A$ is each independently hydrogen or methyl, $R^{11}$ and $R^{12}$ each are an acid labile group, Y1 is a single bond or a $C_1$-$C_{15}$ linking group containing an ester bond, lactone ring, phenylene or naphthylene moiety, and $Y^2$ is a single bond, ester bond or amide bond.

In a preferred embodiment, the base resin further composes recurring units of at least one type selected from the formulae (b1) to (b3).

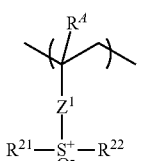
(b1)

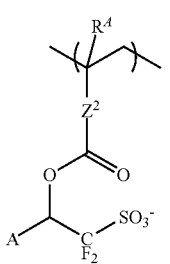
(b2)

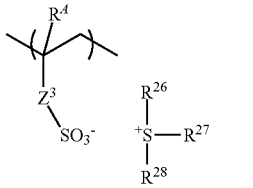
(b3)

Herein $R^A$ is each independently hydrogen or methyl; $Z^1$ is a single bond, phenylene group, —O—$Z^{11}$—, —C(=O)—O—$Z^{11}$—, or —C(=O)—NH—$Z^{11}$—; $Z^2$ is a single bond, —C(=O)—O—$Z^{11}$—, or —C(=O)—NH—$Z^{11}$—; $Z^3$ is a single bond, methylene, ethylene, phenylene, fluorinated phenylene, —O—$Z^{11}$—, —C(=O)—O—$Z^{11}$—, or —C(=O)—NH—$Z^{11}$—; $Z^{11}$ is a $C_1$-$C_6$ alkanediyl group, phenylene group, or $C_2$-$C_{10}$ alkenediyl group, which may contain a carbonyl, ester bond, ether bond or hydroxyl moiety; $R^{21}$ to $R^{28}$ are each independently a $C_1$-$C_{20}$ monovalent hydrocarbon group which may contain a heteroatom, a pair of $R^{21}$ and $R^{22}$ may bond together to form a ring with the sulfur atom to which they are attached, any two of $R^{23}$, $R^{24}$ and $R^{25}$ or any two of $R^{26}$, $R^{27}$ and $R^{28}$ may bond together to form a ring with the sulfur atom to which they are attached; A is hydrogen or trifluoromethyl; and $Q^-$ is a non-nucleophilic counter ion.

More preferably, the base resin comprises recurring units of formula (b2).

Typically the resist composition is a chemically amplified positive resist composition.

The resist composition may further comprise an organic solvent, acid generator, quencher, and/or surfactant.

In another aspect, the invention provides a process for forming a pattern comprising the steps of applying the resist composition defined above onto a substrate, baking to form a resist film, exposing the resist film to high-energy radiation, and developing the exposed film in a developer.

In a preferred embodiment, the high-energy radiation is EUV of wavelength 3 to 15 nm or EB emitted at an accelerating voltage of 1 to 150 kV.

Preferably, during the exposure step, the surface of the substrate underlying the resist film is electrically charged positive.

In a further aspect, the invention provides a barium salt having the formula (2).

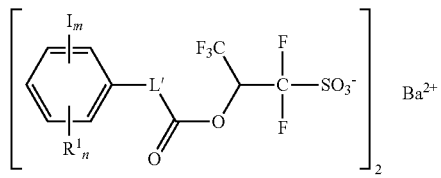

(2)

Herein $R^1$, m and n are as defined above, L' is a single bond, or a $C_1$-$C_{12}$ alkanediyl, $C_2$-$C_{12}$ alkenediyl or $C_6$-$C_{10}$ arylene group which may contain an ether bond or ester bond.

ADVANTAGEOUS EFFECTS OF INVENTION

The resist composition has many advantages including a significantly high contrast of alkaline dissolution rate before and after exposure, a high sensitivity, a high resolution, exposure latitude, process adaptability, a satisfactory pattern profile after exposure, a controlled rate of acid diffusion, and a minimal LWR or improved CDU. The resist composition is suited as the micropatterning material for VLSIs and photomasks, and the patterning material in the EB and EUV lithography. The resist composition is used not only in the lithography for semiconductor circuit formation, but also in the formation of mask circuit patterns, micro-machines, and thin-film magnetic head circuits.

DESCRIPTION OF EMBODIMENTS

The singular forms "a," "an" and "the" include plural referents unless the context clearly dictates otherwise. "Optional" or "optionally" means that the subsequently described event or circumstance may or may not occur, and that the description includes instances where the event occurs and instances where it does not. As used herein, the notation ($C_n$-$C_m$) means a group containing from n to m carbon atoms per group. Me stands for methyl and Ac for acetyl.

The abbreviations and acronyms have the following meaning.
EUV: extreme ultraviolet
EB: election beam
Mw: weight average molecular weight
Mn: number average molecular weight
Mw/Mn: molecular weight distribution or dispersity
GPC: gel permeation chromatography
PEB: post-exposure bake
LWR: line width roughness
CDU: critical dimension uniformity Resist Composition One embodiment of the invention is a resist composition comprising a base resin comprising recurring units containing an acid labile group, and a sulfonic acid metal salt.

Metal Salt

The sulfonic acid metal salt has the formula (1).

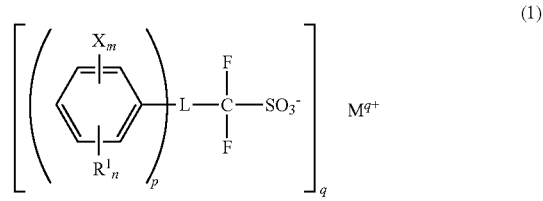

(1)

In formula (1), X is each independently iodine or bromine.

$R^1$ is hydroxy, $C_1$-$C_{20}$ alkyl, $C_1$-$C_{20}$ alkoxy, $C_2$-$C_{20}$ acyloxy, fluorine, chlorine, amino, —$NR^2$—C(=O)—$R^3$, or —$NR^2$—C(=O)—O—$R^3$. In the alkyl, alkoxy or acyloxy group, at least one (one or more or even all) hydrogen may be substituted by fluorine, chlorine, bromine, iodine, hydroxyl, amino or a $C_1$-$C_6$ alkoxy moiety. $R^2$ is a $C_1$-$C_6$ alkyl group. $R^3$ is a $C_1$-$C_{16}$ alkyl, $C_2$-$C_{16}$ alkenyl or $C_1$-$C_{12}$ aryl group in which at least one (one or more or even all) hydrogen may be substituted by a halogen, hydroxyl, $C_1$-$C_6$ alkoxy, $C_2$-$C_6$ acyl or $C_2$-$C_6$ acyloxy moiety. The alkyl, alkoxy, acyloxy, alkenyl and acyl groups may be straight, branched or cyclic. Inter alia, $R^1$ is preferably hydroxyl, —$NR^2$—C(=O)—$R^3$, methyl or methoxy.

L is a single bond or a (p+1)-valent $C_1$-$C_{20}$ hydrocarbon group which may contain an ether bond, carbonyl, ester bond, amide bond, sultone, lactam, carbonate, halogen, hydroxyl or carboxyl moiety.

$M^{q+}$ is a sodium, magnesium, potassium, calcium, rubidium, strontium, yttrium, cesium, barium or cerium ion.

The subscript m is an integer of 2 to 5, n is an integer of 0 to 3, m+n is 2 to 5, preferably m is an integer of 2 to 4, most preferably 2 or 3. The subscript p is an integer of 1 to 3, and q is an integer of 1 to 3.

Upon imagewise exposure to EB or EUV, the sodium, magnesium, potassium, calcium, rubidium, strontium, yttrium, cesium, barium or cerium ion generates secondary electrons, to which the acid generator is sensitive. This leads to a high sensitivity. However, if secondary elections randomly diffuse in the resist film, the image is blurred. With this combined with diffusion of the acid generated by the acid generator, the image blur is exaggerated, inviting an increase of edge roughness. If secondary electron diffuse in the thickness direction of the resist film, i.e., perpendicular to the substrate, then the image blur is suppressed. When the substrate is electrically charged positive (+), secondary electrons move as if they were sucked into the substrate, that is, secondary electrons diffuse perpendicularly. Then the sensitivity can be improved while suppressing the image blur, and without degrading the edge roughness.

Since the sulfonic acid metal salt having formula (1) does not undergo ion exchange with the acid generated from the acid generator, it does not function as a quencher. This allows the salt having formula (1) to be added in a more amount than quenchers. Thus the advantages of increased absorption of EB or EUV and increased sensitivity are available.

Specifically the sulfonic acid metal salt having formula (1) is a sodium, magnesium, potassium, calcium, rubidium, strontium, yttrium, cesium, barium or cerium salt as shown below.

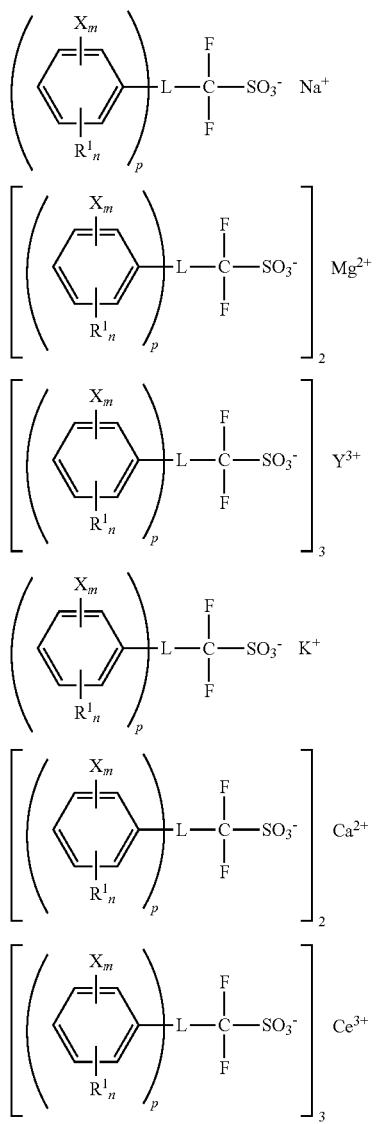

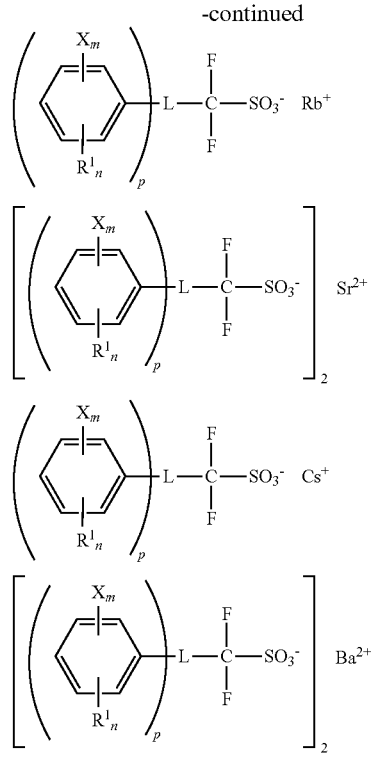

Herein X, $R^1$, L, m, n and p are as defined above.

It is believed that the sulfonic acid metal salt functions as follows. The sulfonic acid metal salt has an anion of α-fluorosulfonic acid having an iodized or brominated benzene ring. Since the iodine atom is highly absorptive to EUV, it absorbs energy during EUV exposure. Where the anion is an anion of α-fluorosulfonic acid having an iodized benzene ring, the sulfonic acid metal salt absorbs EUV, which causes the metal ion to emit secondary electrons. The bromine atom is ionized upon EUV or EB exposure. Where the anion is an anion of α-fluorosulfonic acid having a brominated benzene ring, the bromine atom is ionized by EUV or EB, which causes the metal ion to emit secondary elections. In this context, the iodine and bromine atoms are effective for facilitating the emission of secondary electrons from the sodium, magnesium, potassium, calcium, rubidium, strontium, yttrium, cesium, barium or cerium ion.

Examples of the anion of the sulfonic acid metal salt are shown below, but not limited thereto.

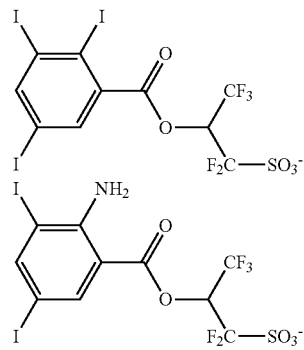

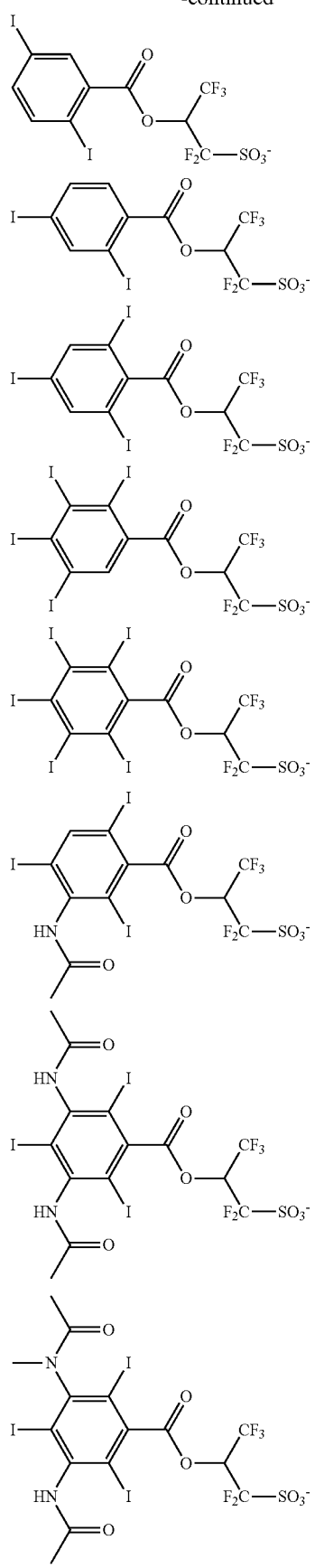
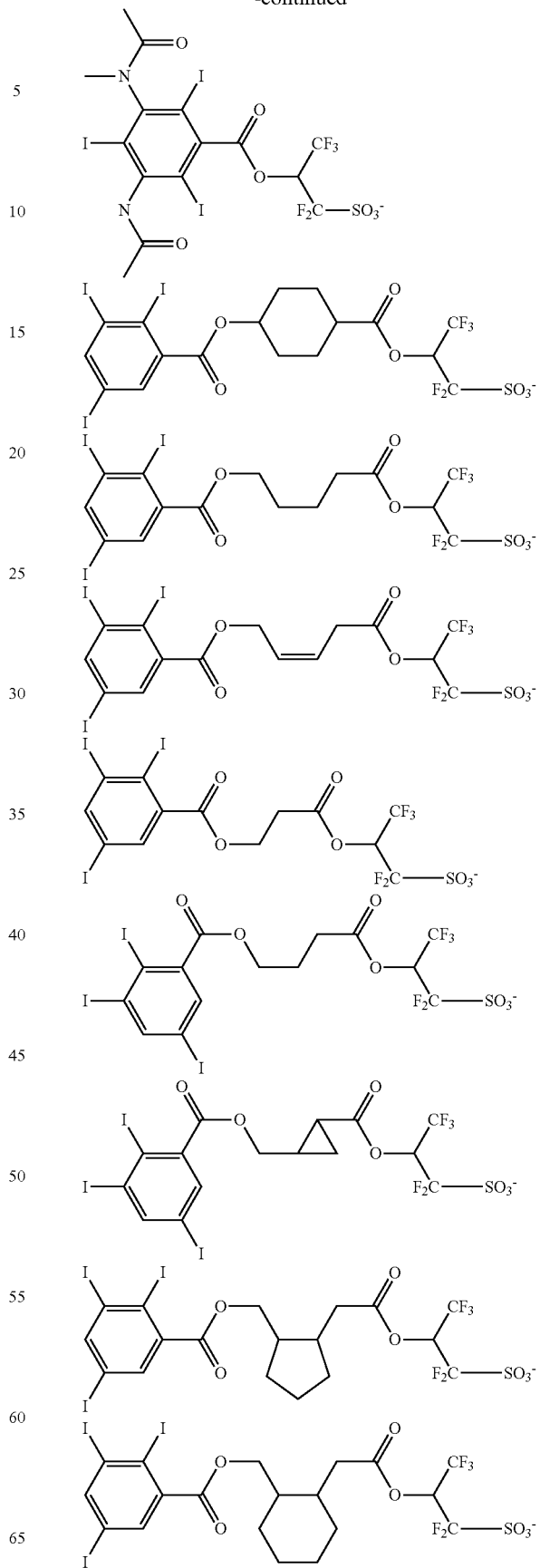

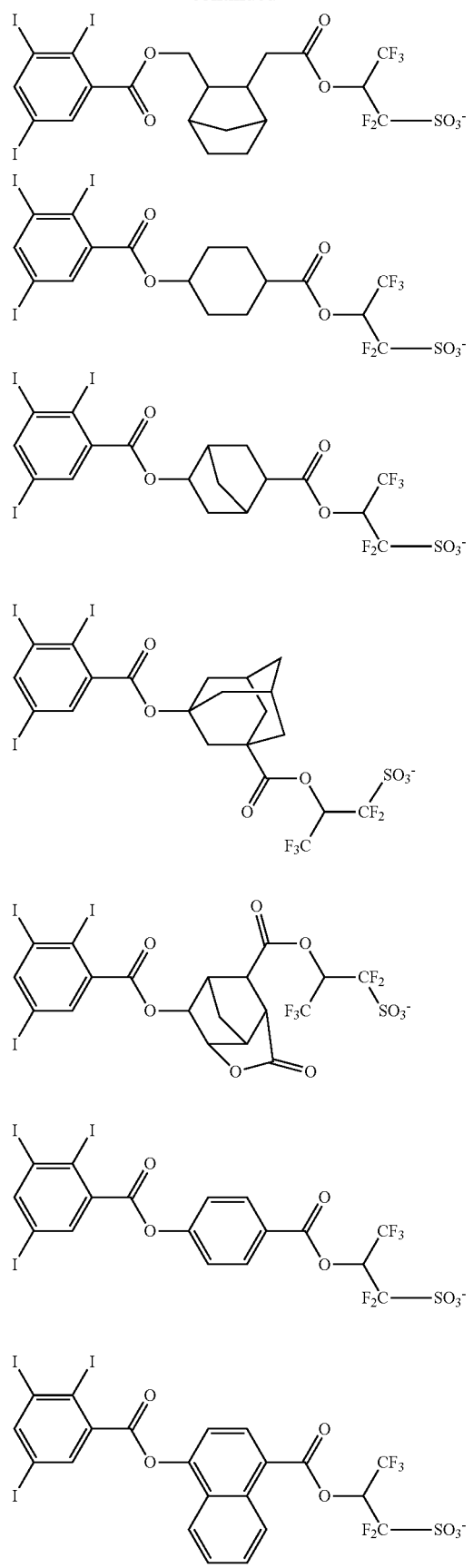
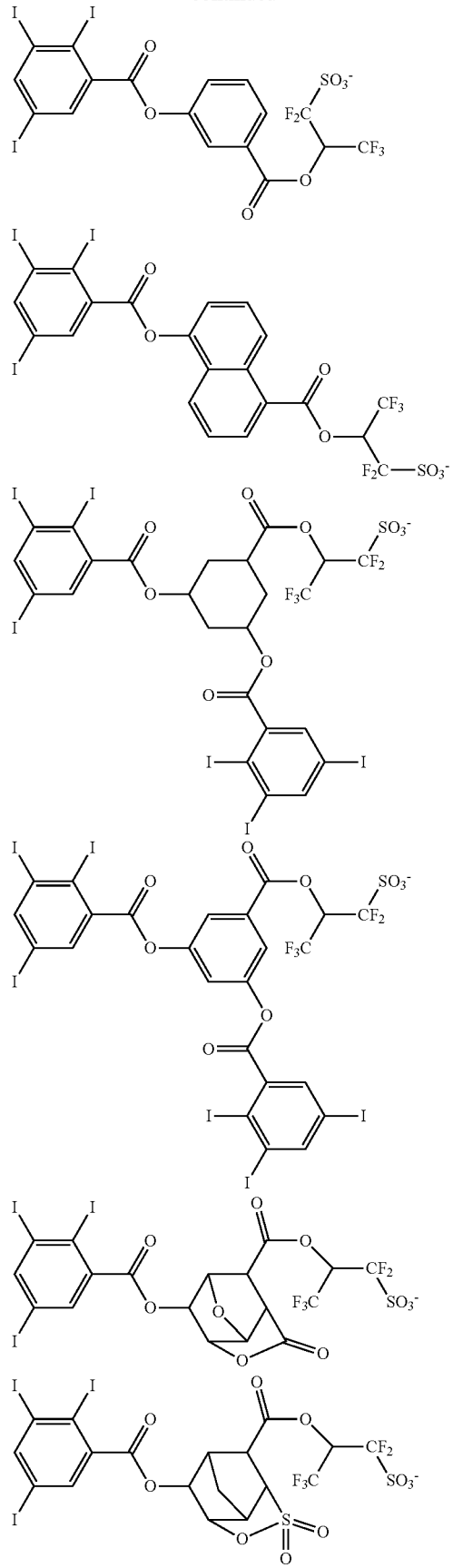

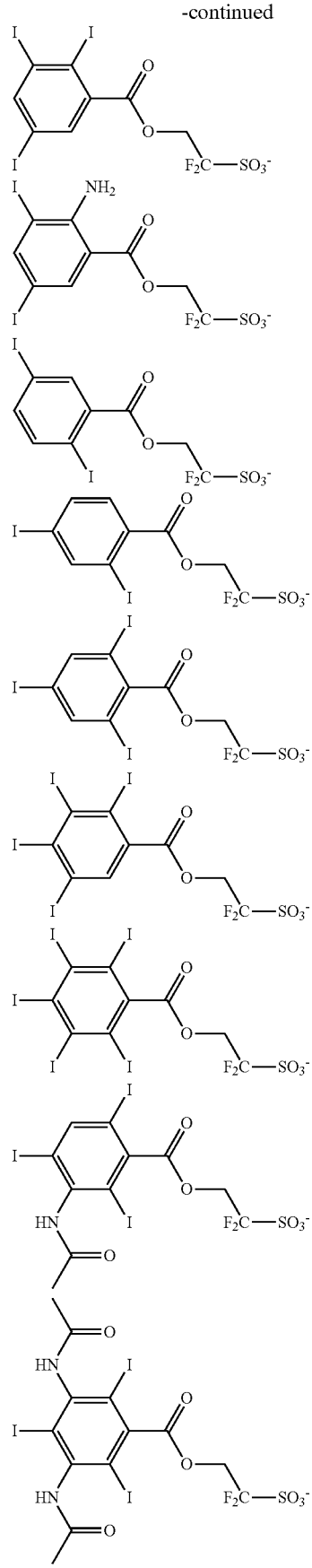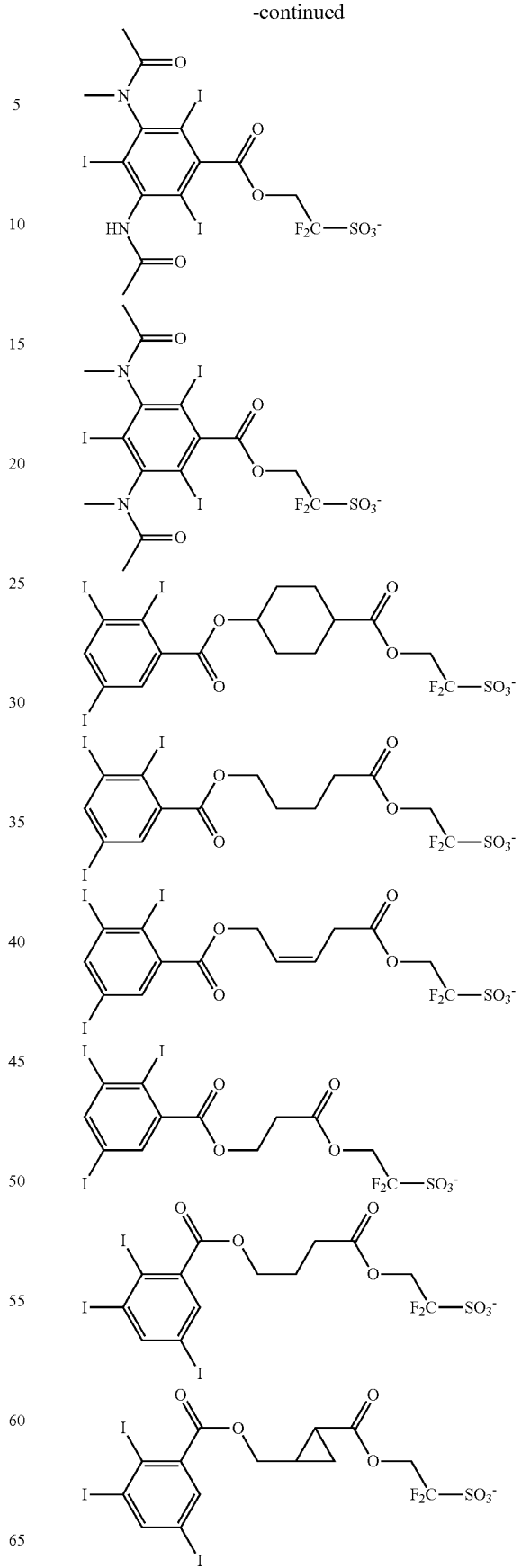

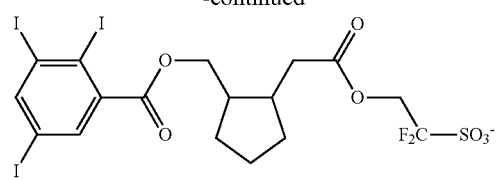
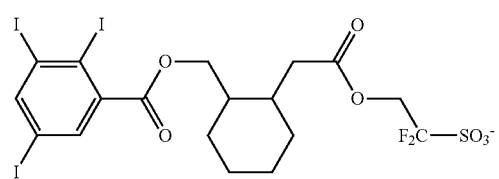
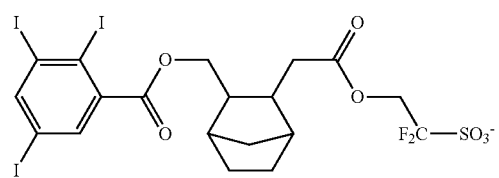
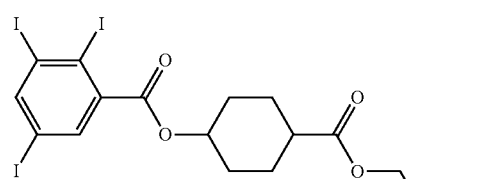
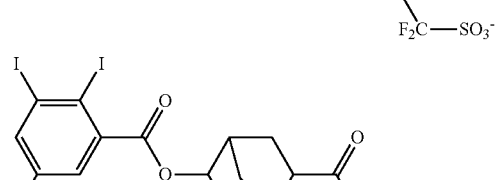
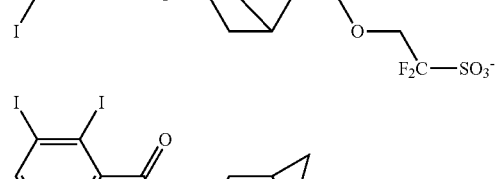
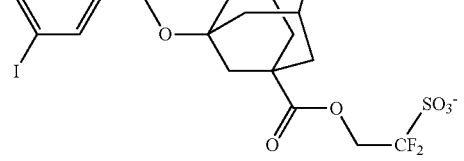
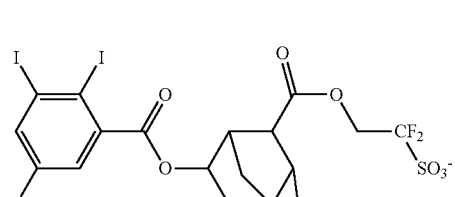
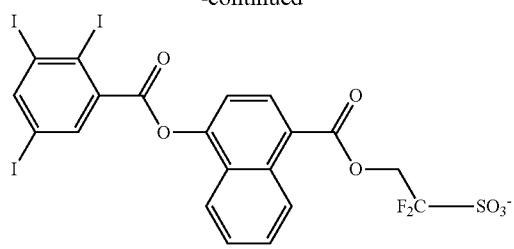
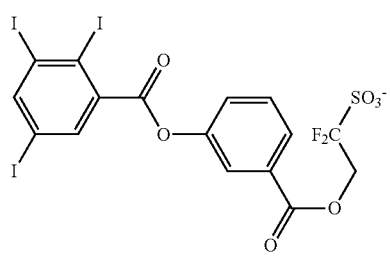
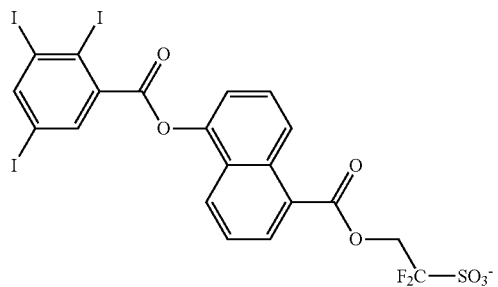
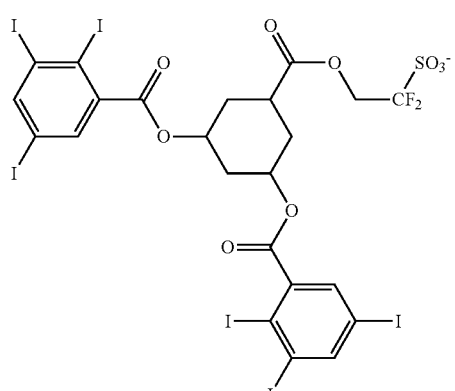
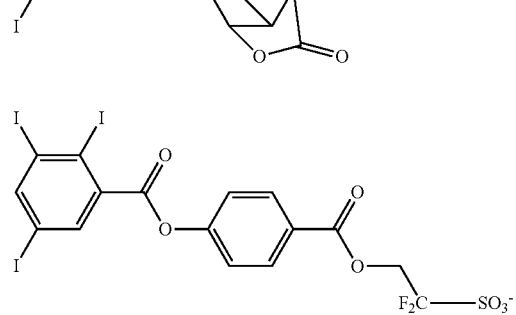
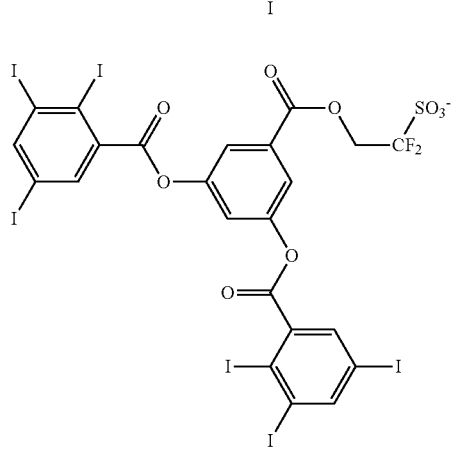

-continued
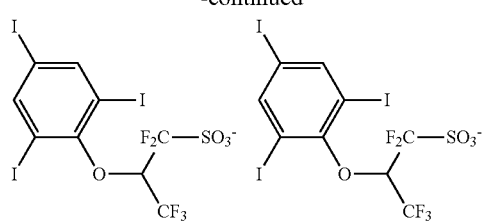
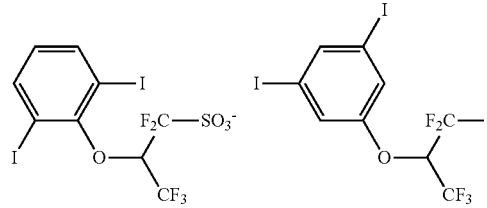
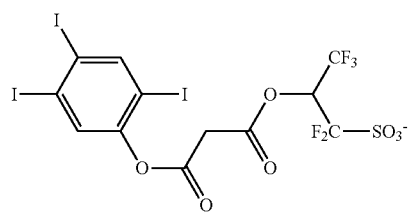
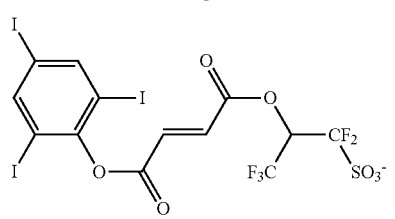
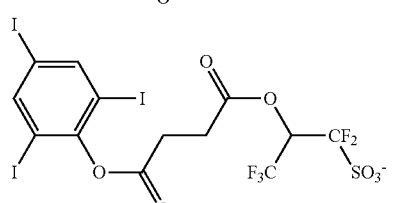
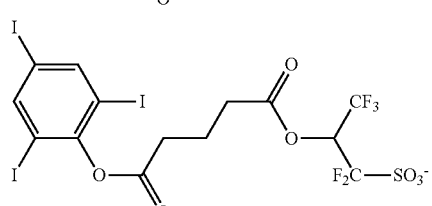
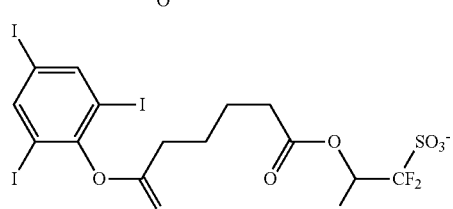
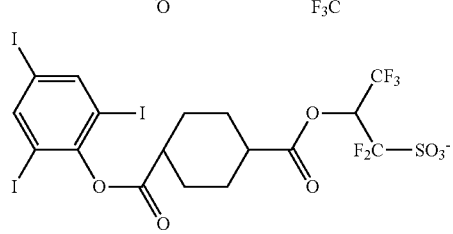
-continued
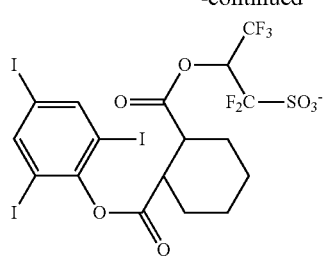
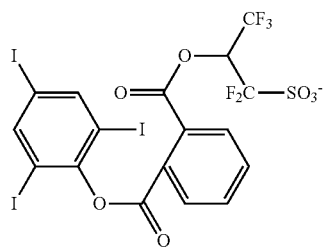
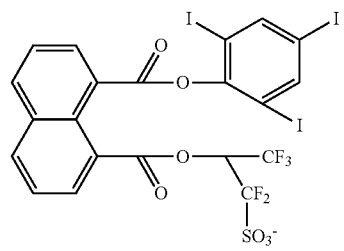
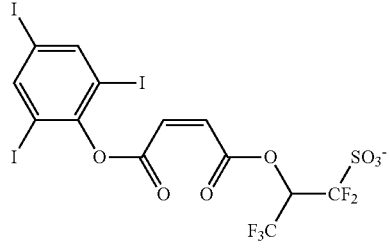
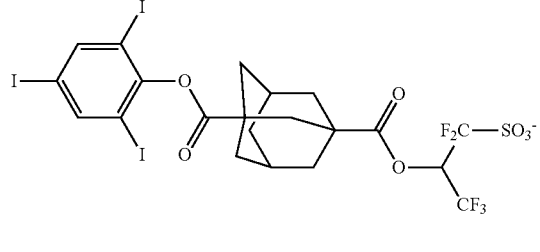
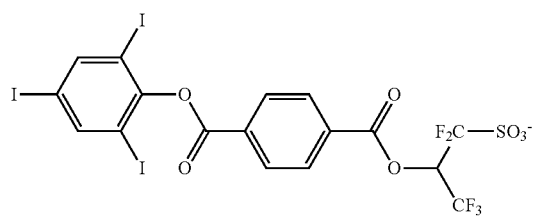

19
-continued
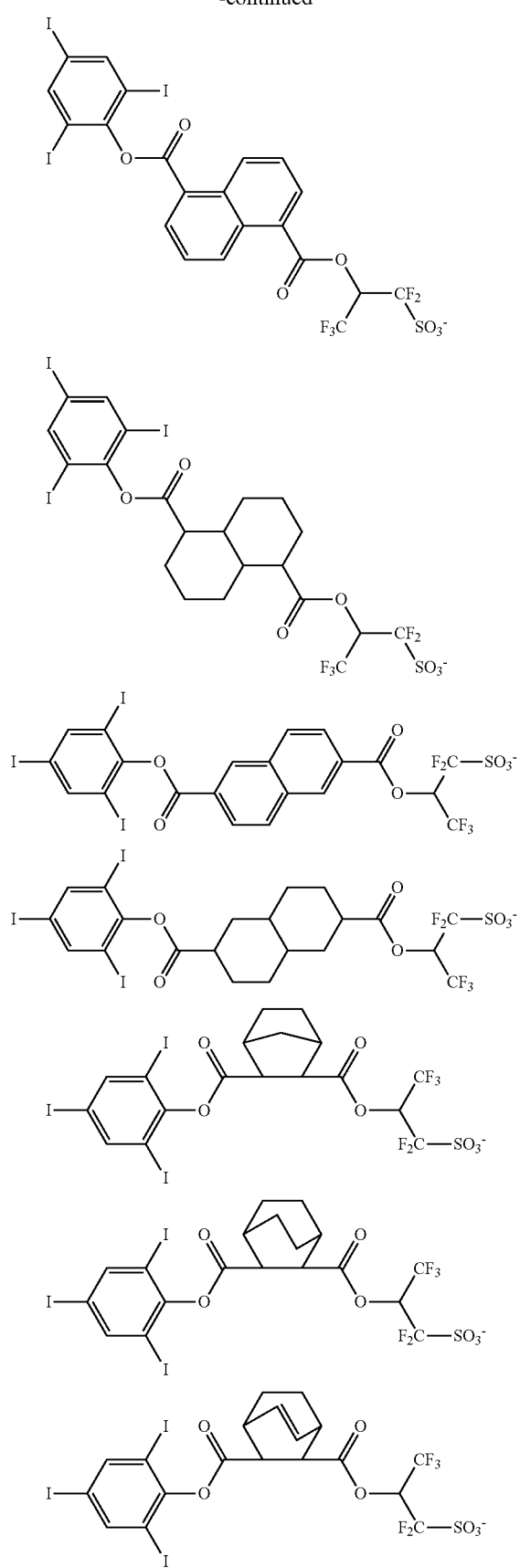
20
-continued
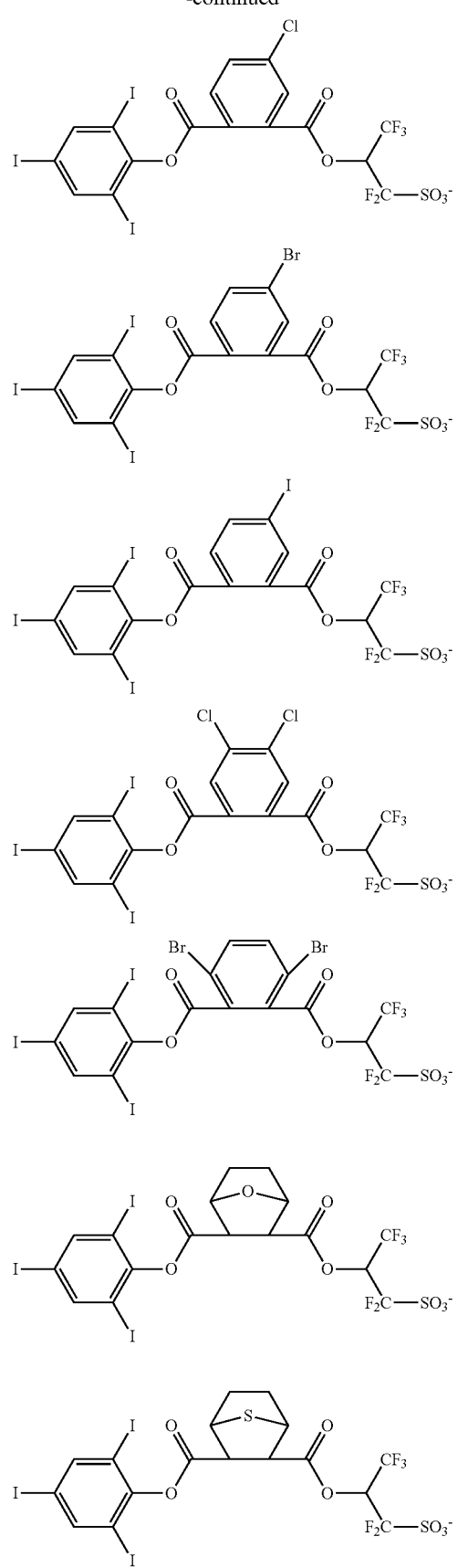

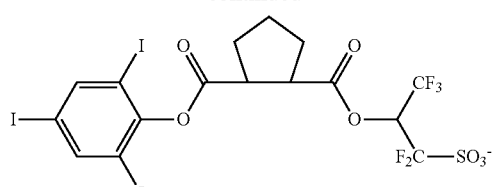
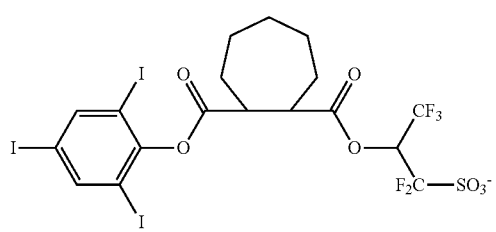
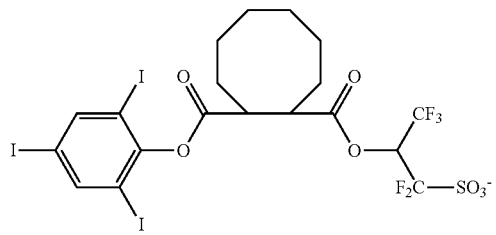
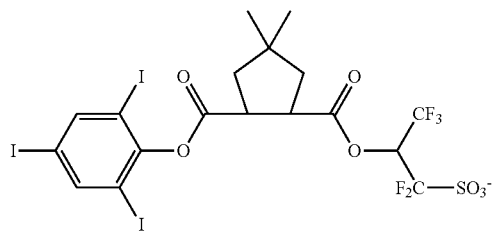
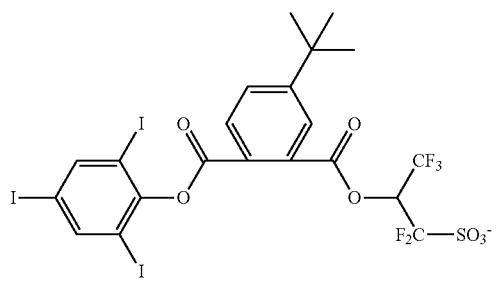
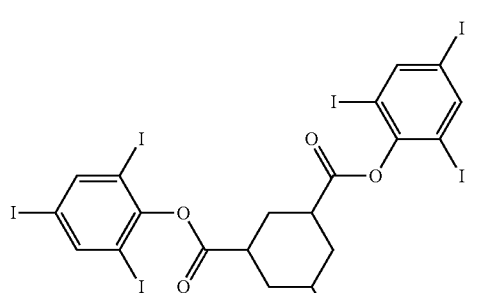
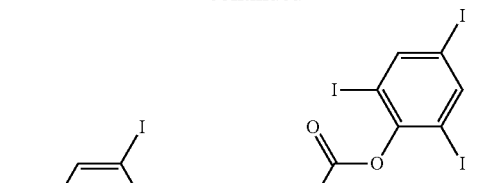
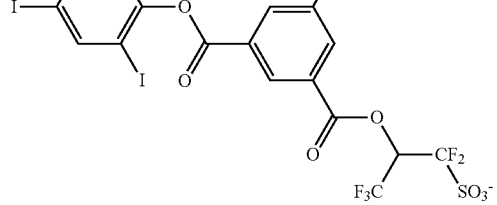
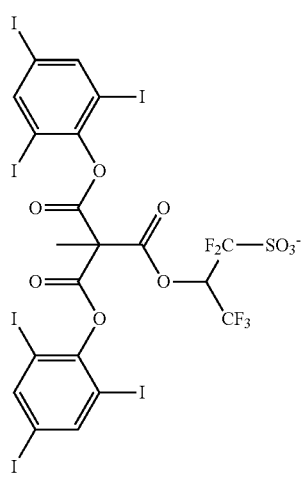
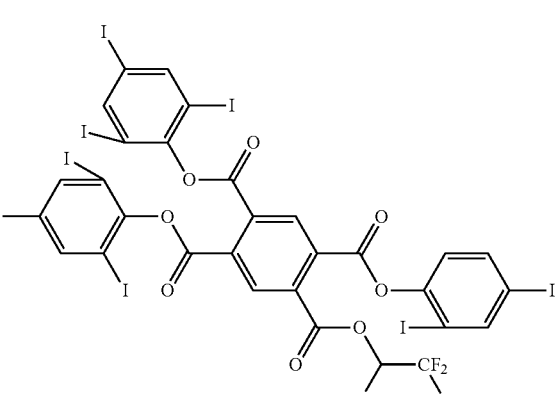
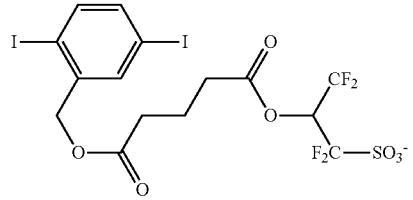

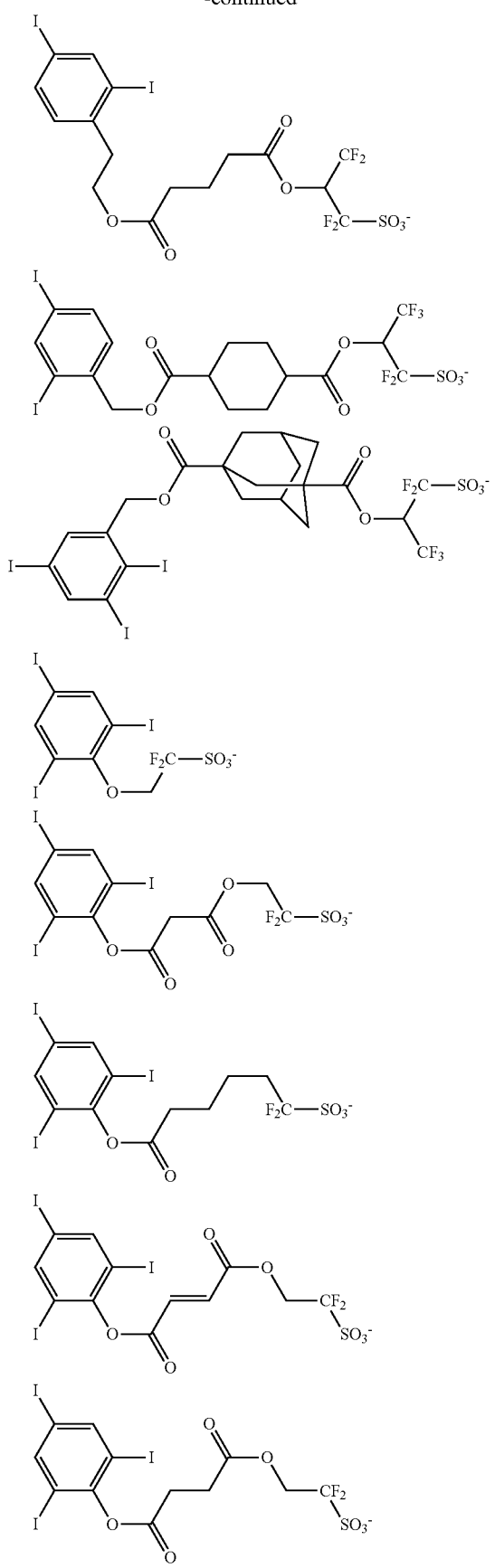
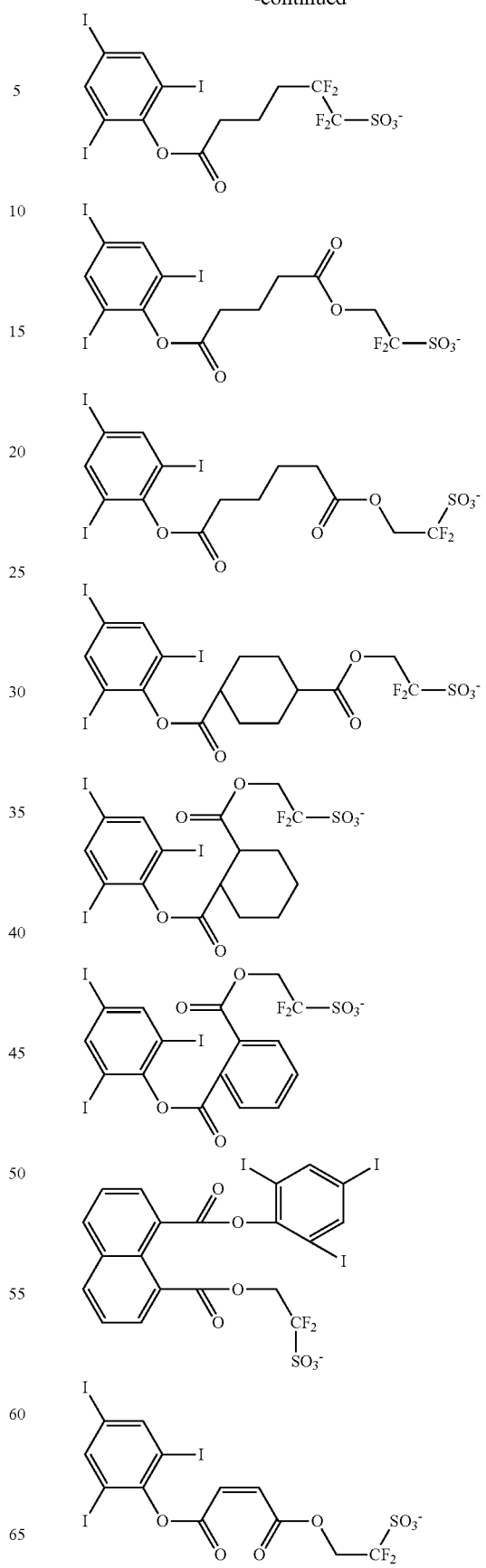

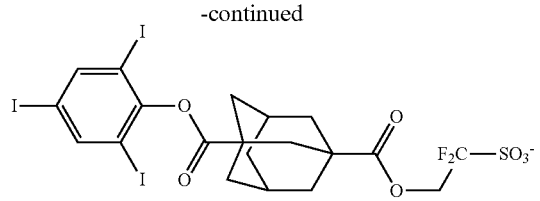
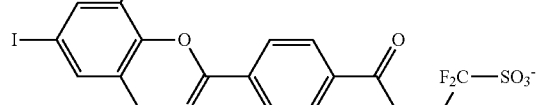
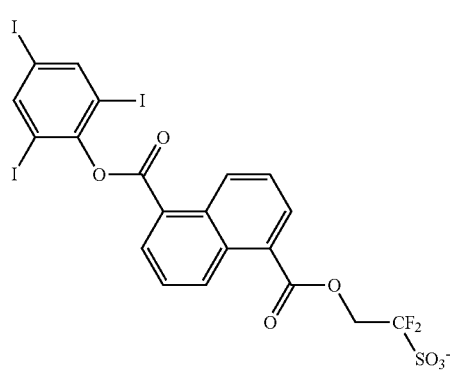
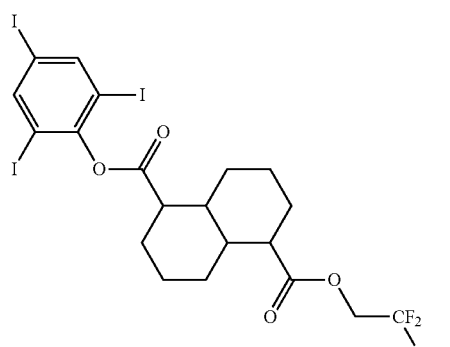
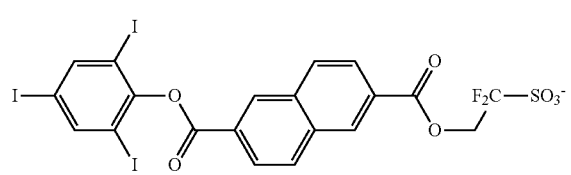
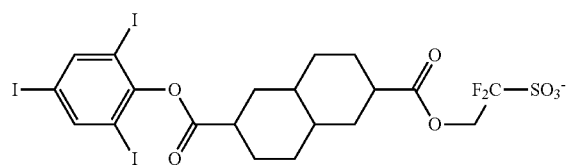
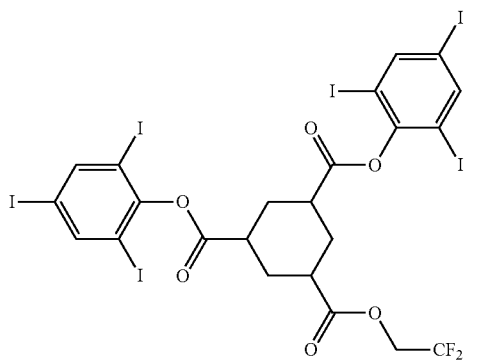
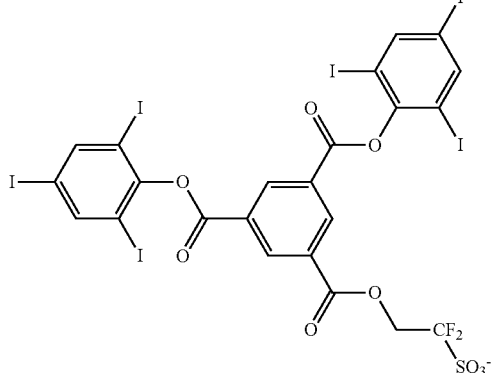
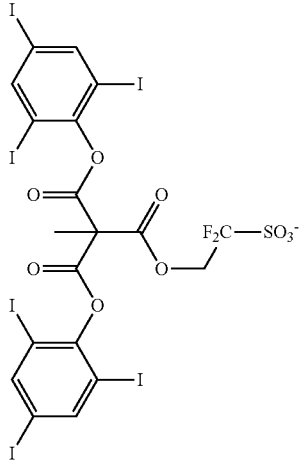
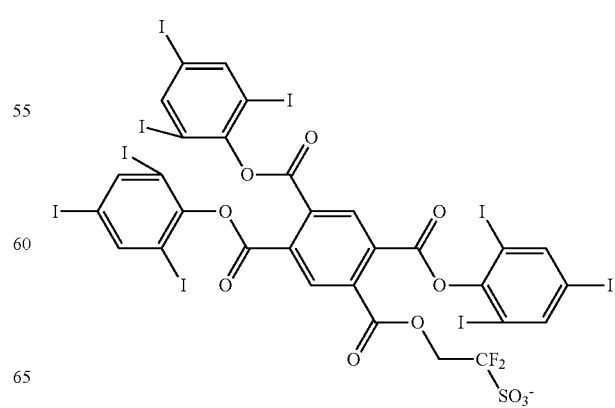

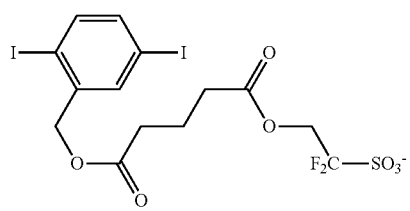
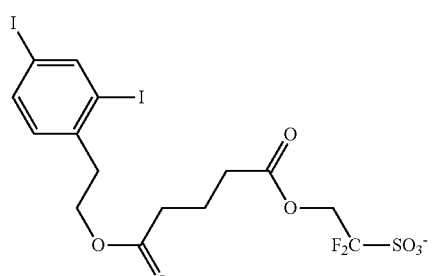
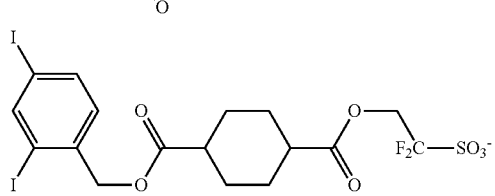
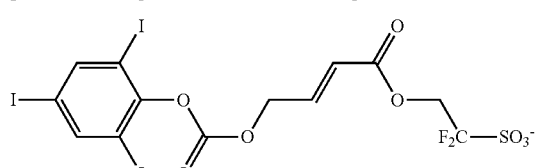
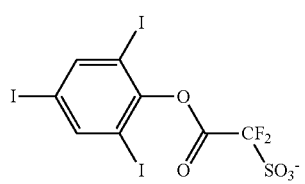
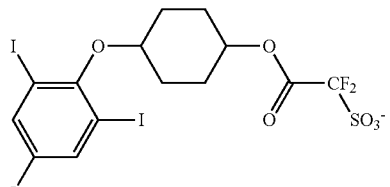
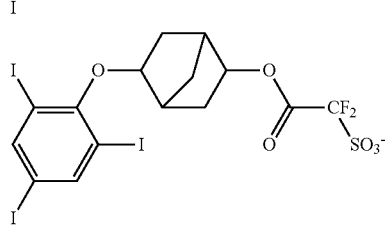
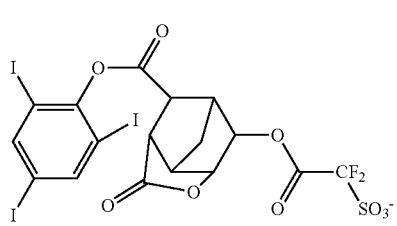
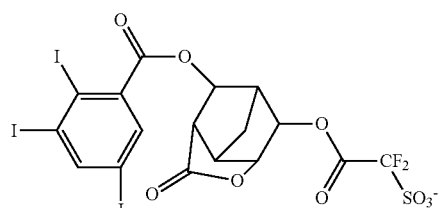
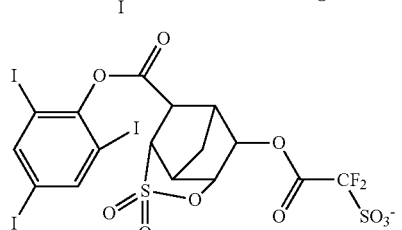
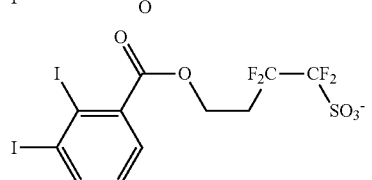
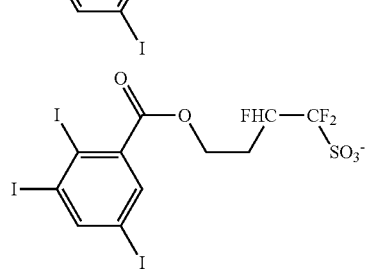
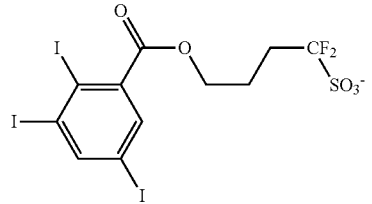
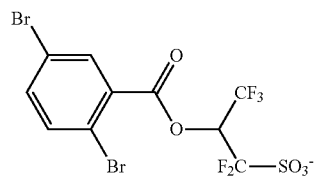
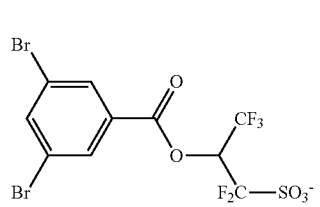
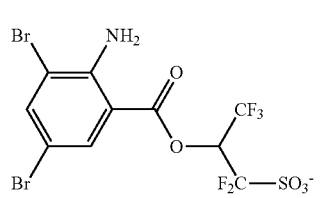

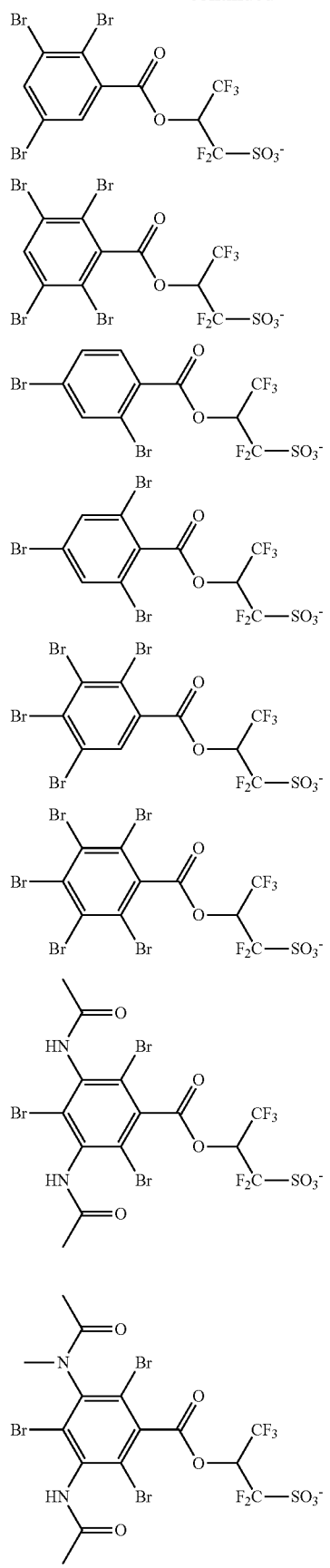
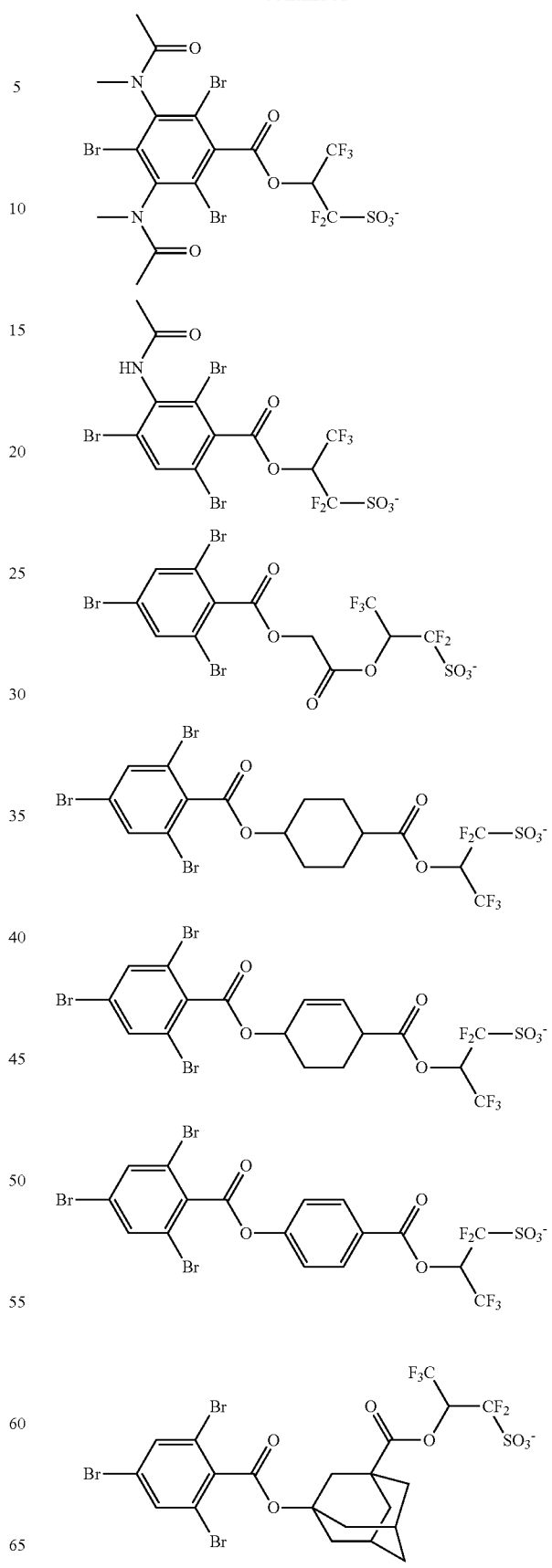

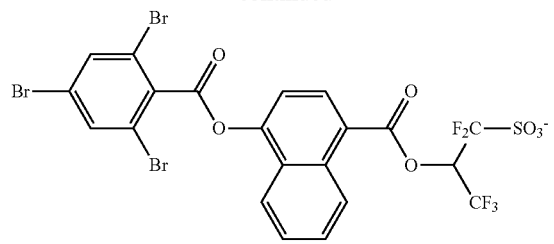
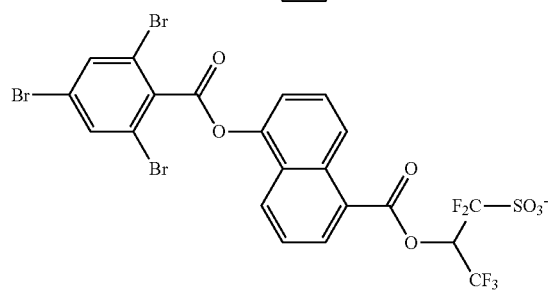
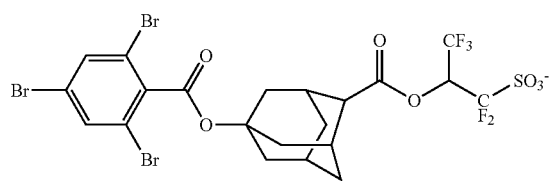
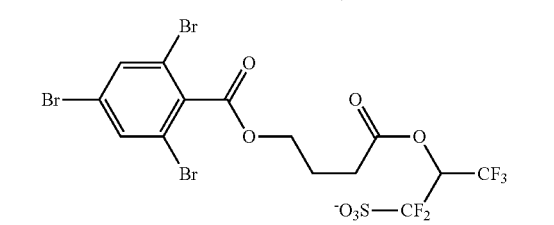
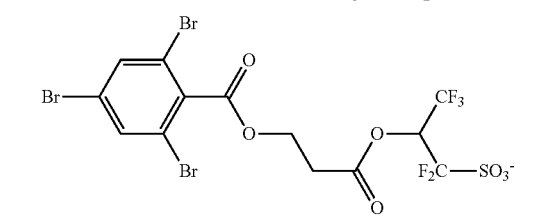
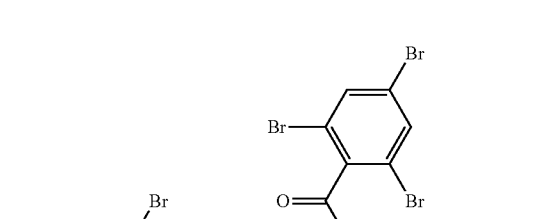
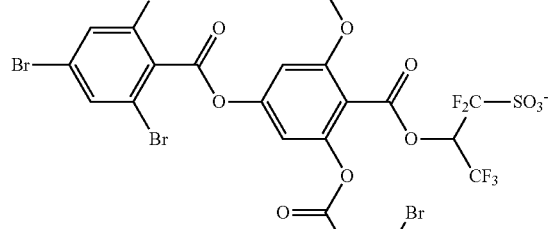
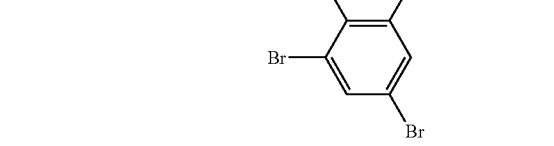
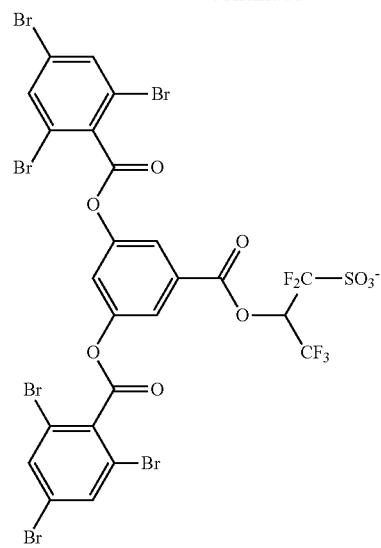
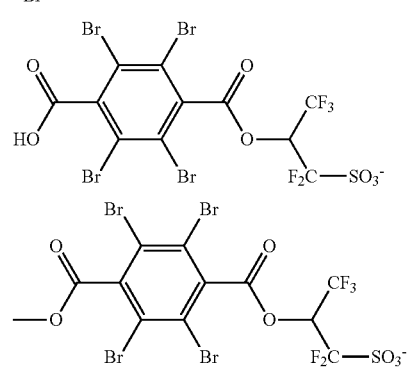
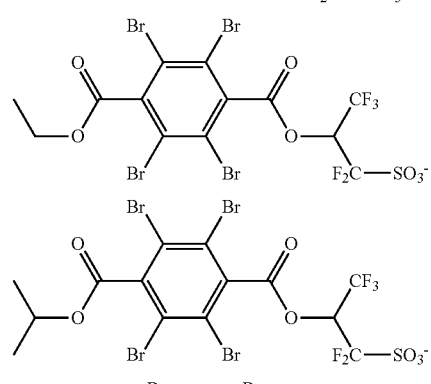
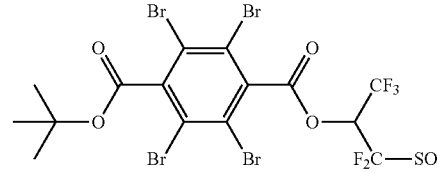
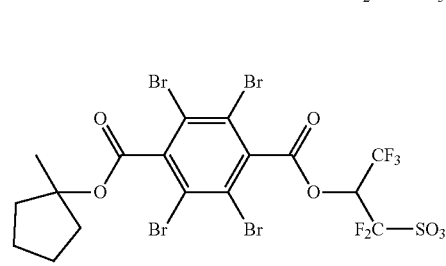

-continued
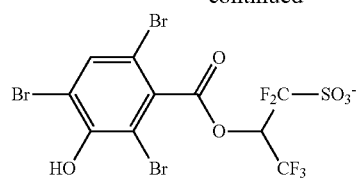
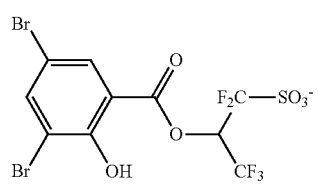
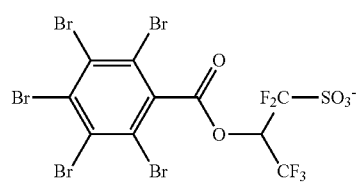
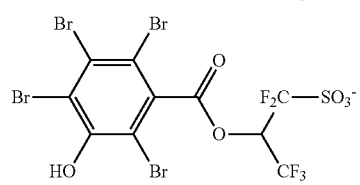
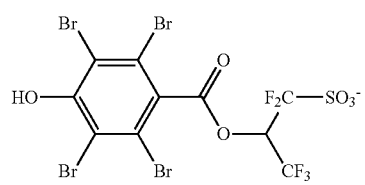
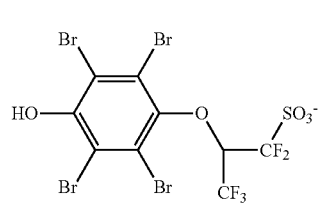
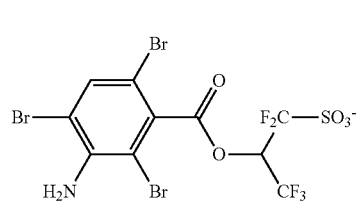
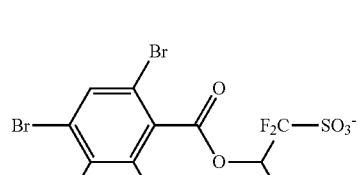
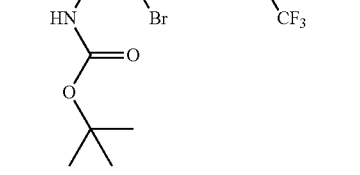
-continued
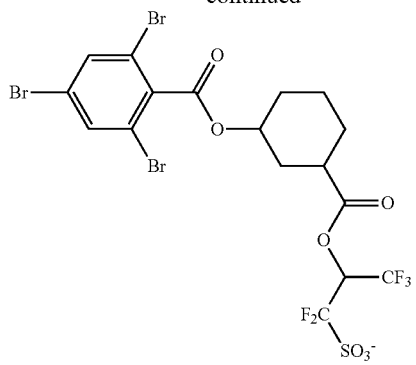
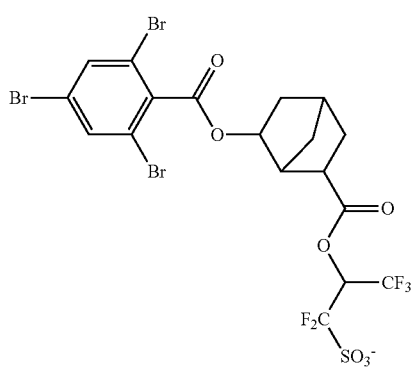
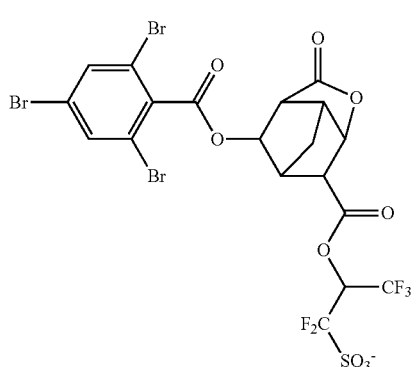
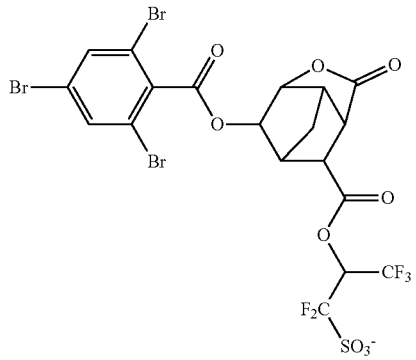

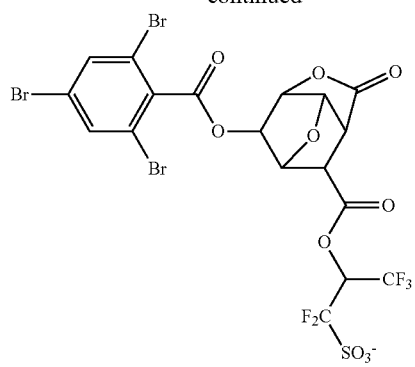
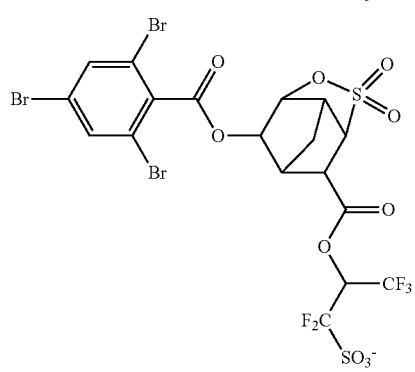
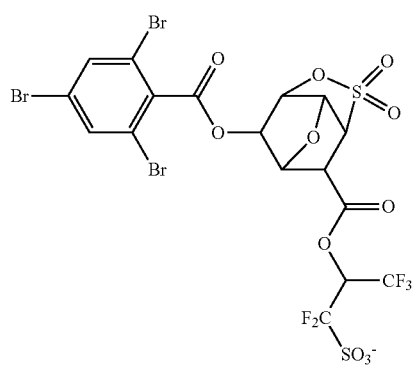
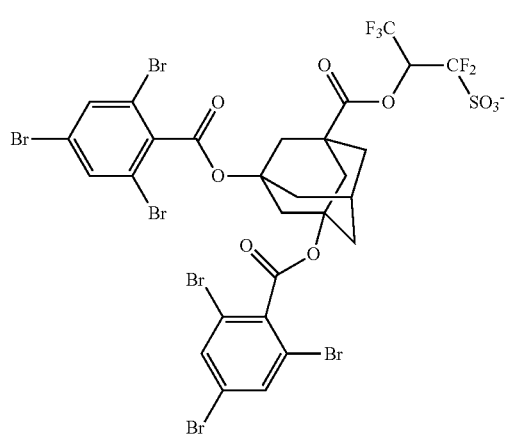
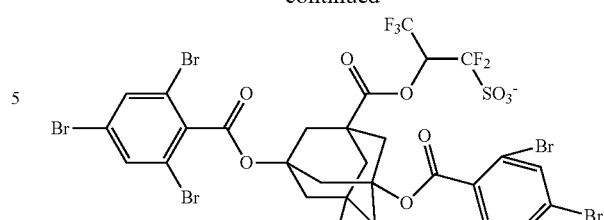
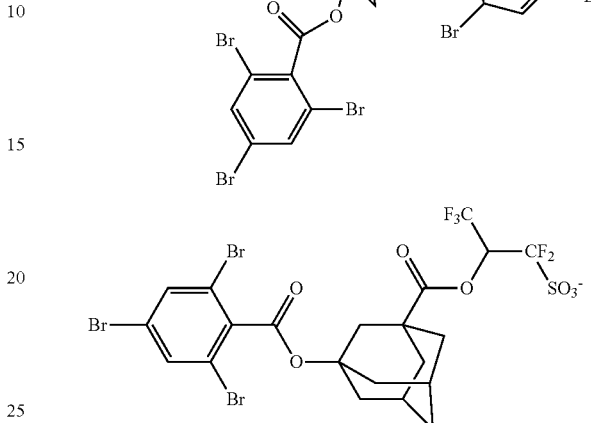
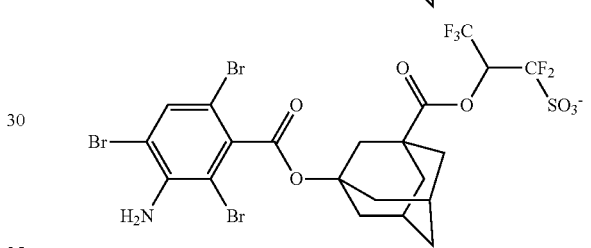
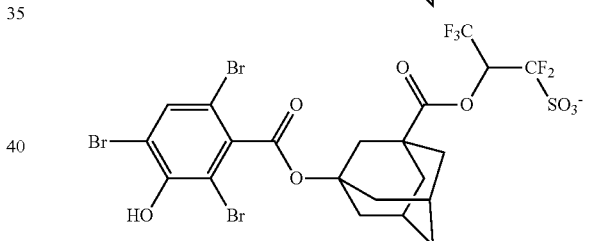
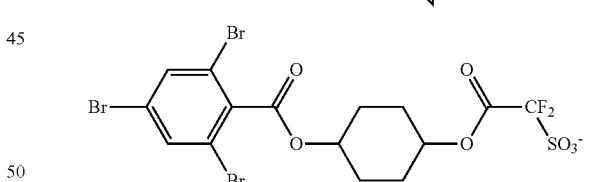
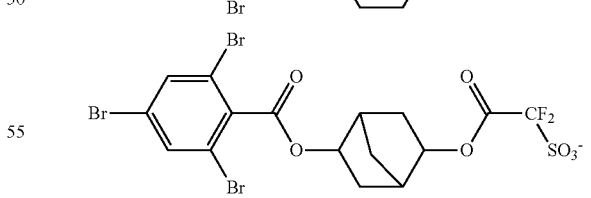
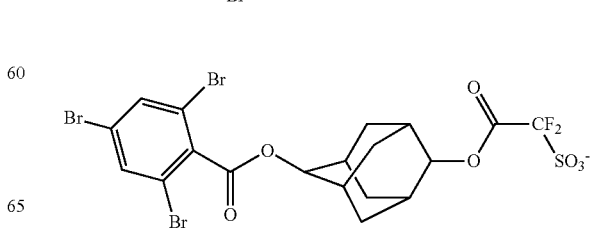

-continued
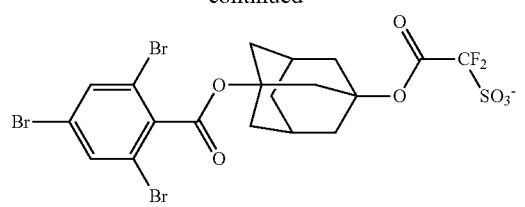
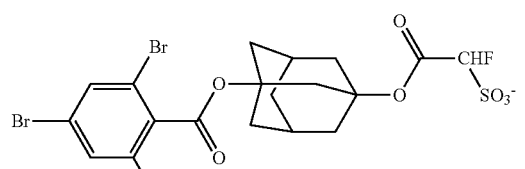
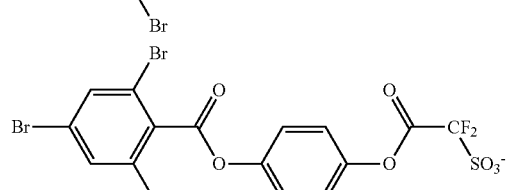
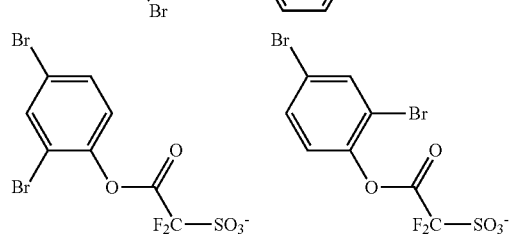
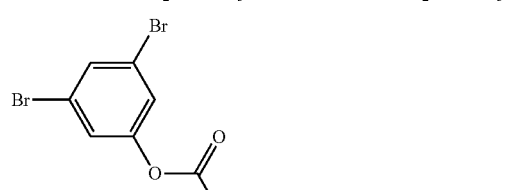
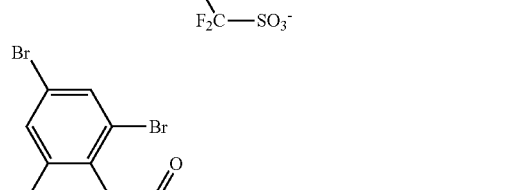
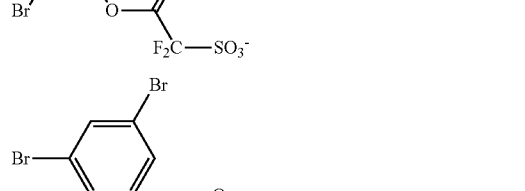
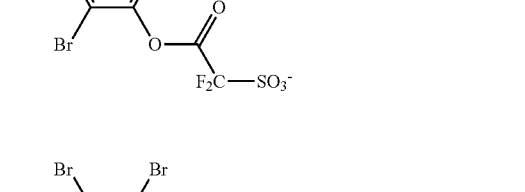
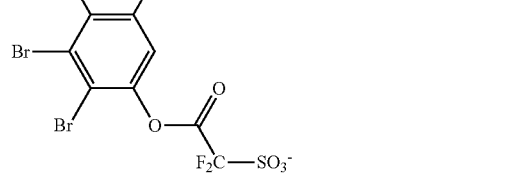
-continued
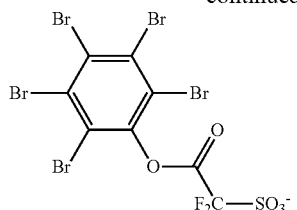
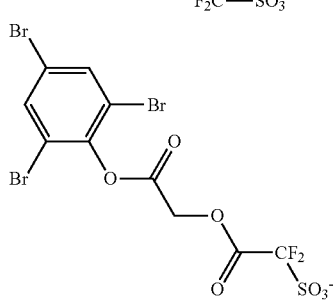
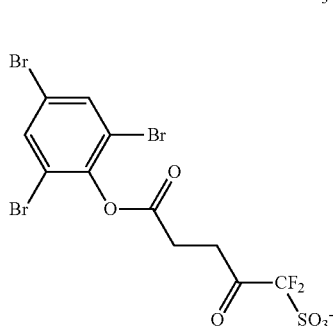
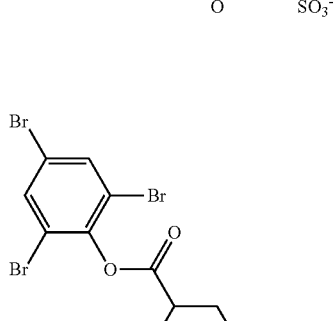
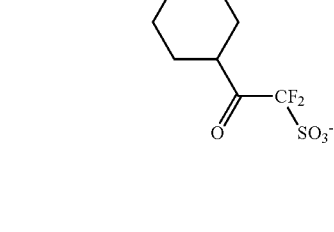
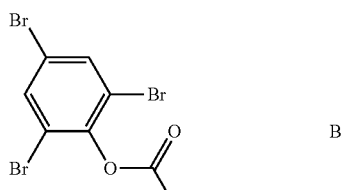
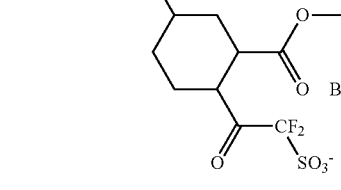

-continued
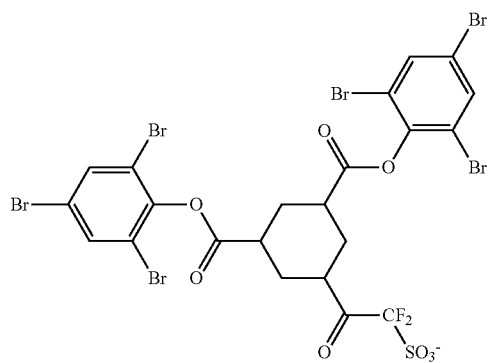
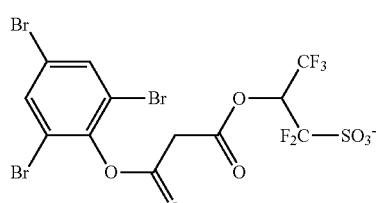
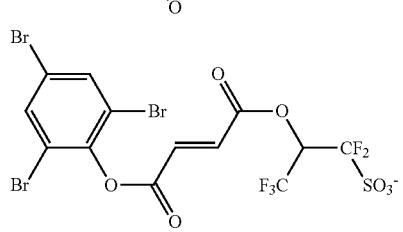
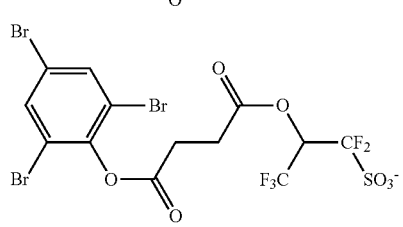
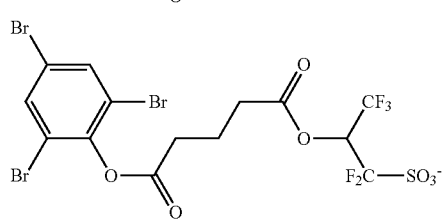
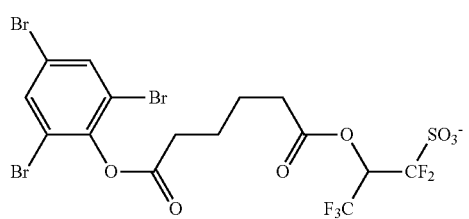
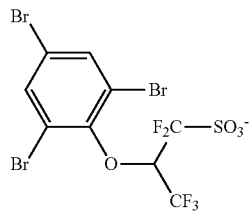
-continued
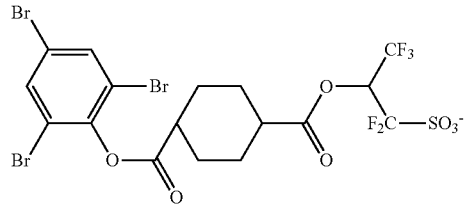
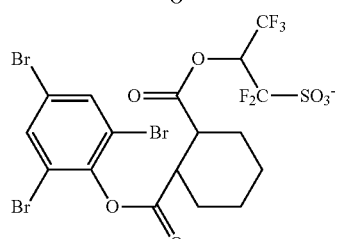
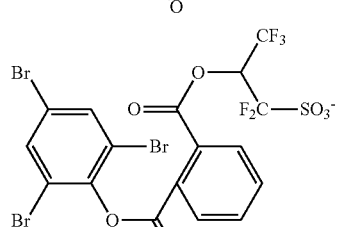
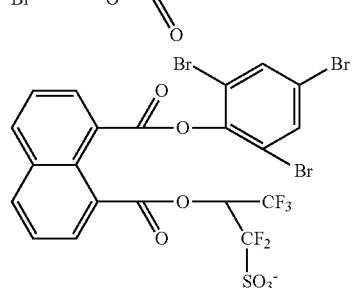
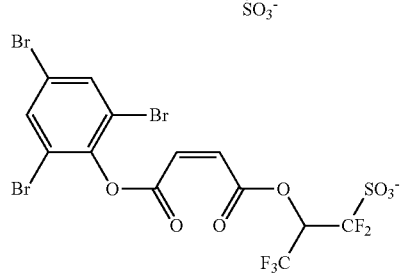
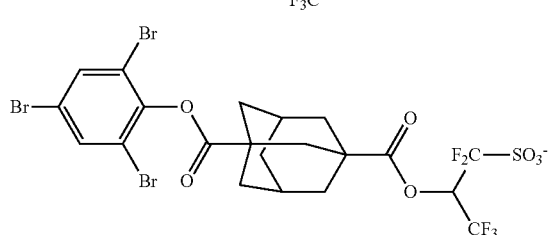
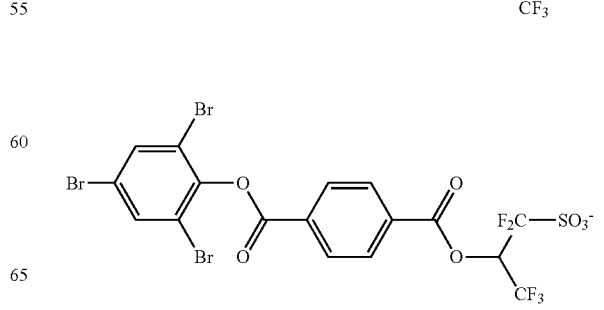

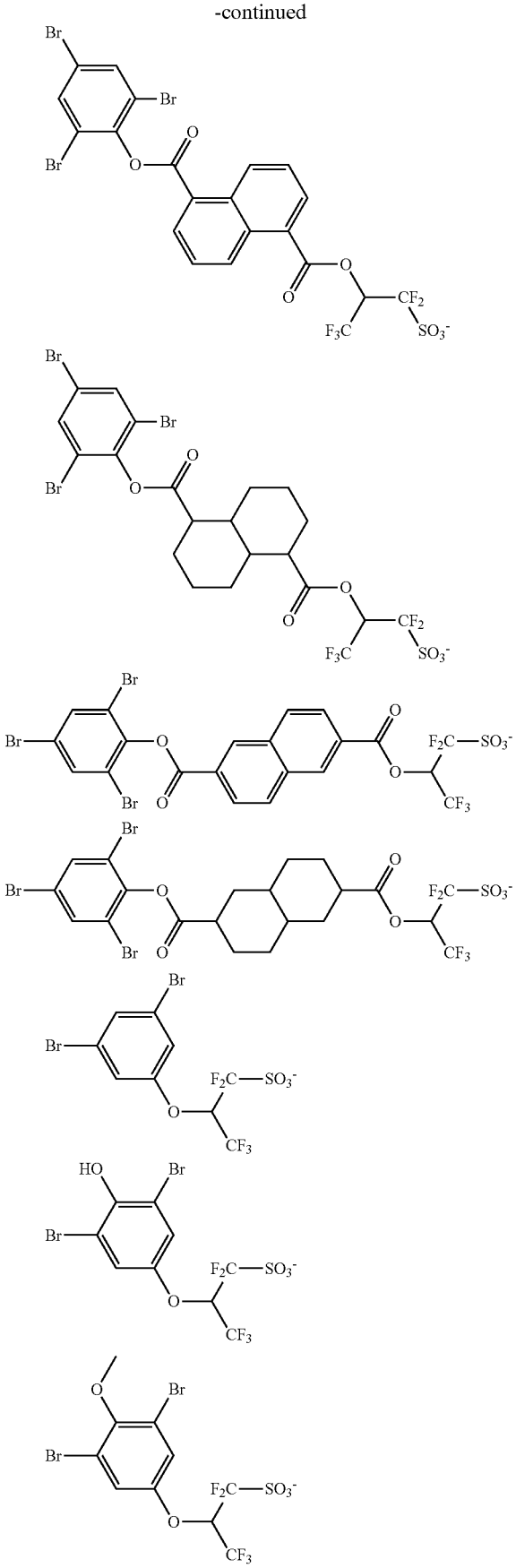
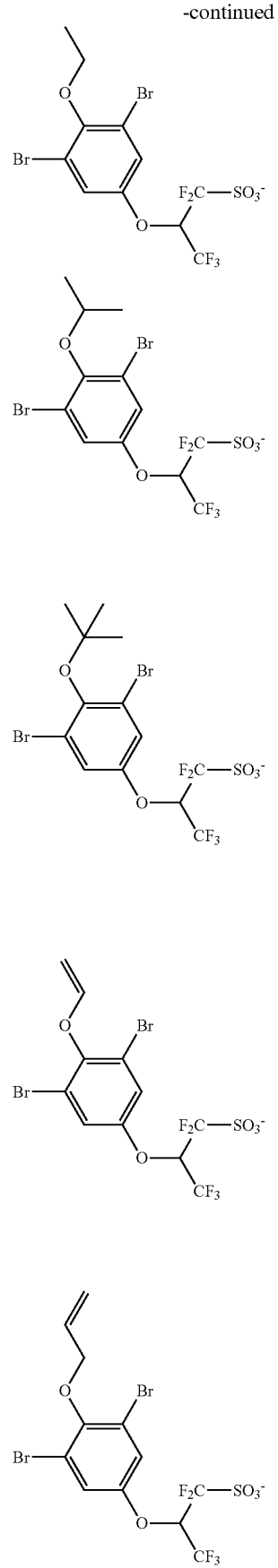

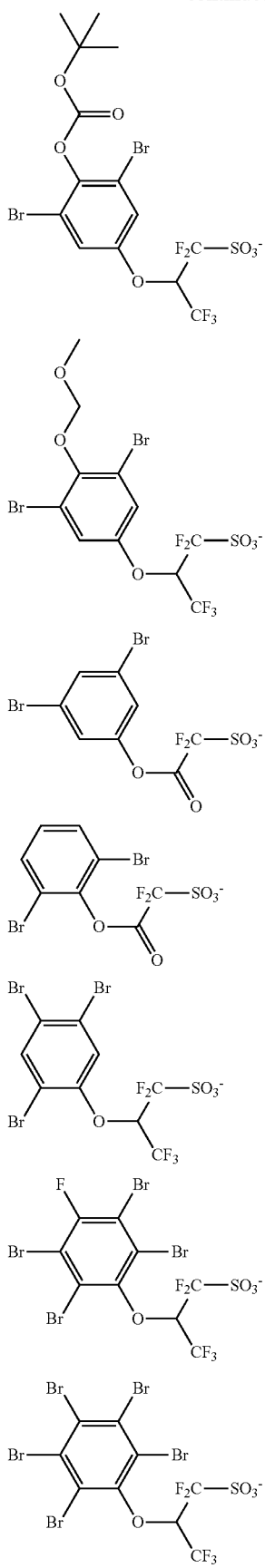
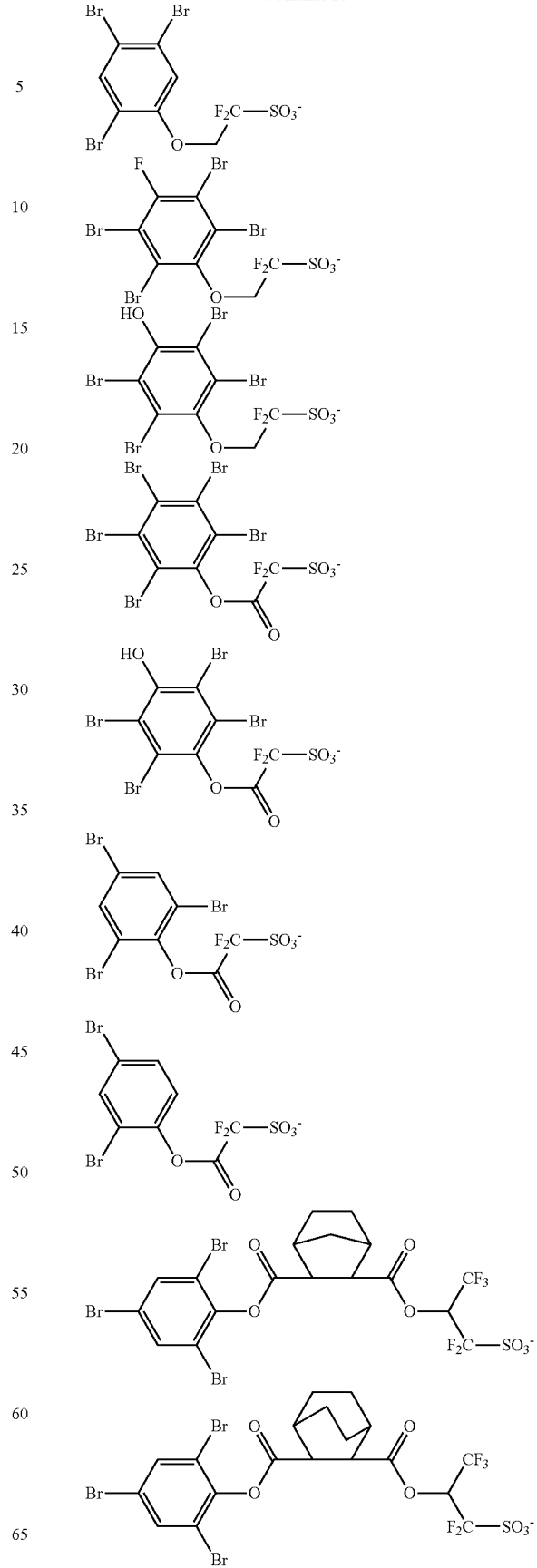

-continued
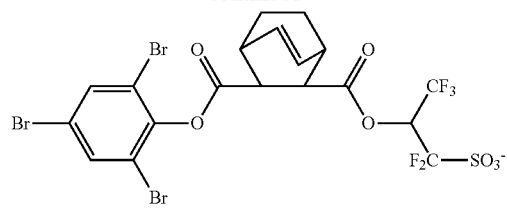
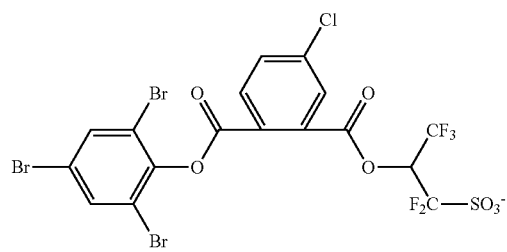
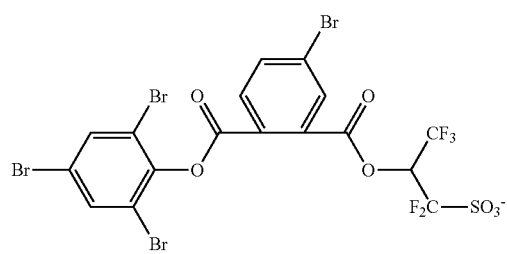
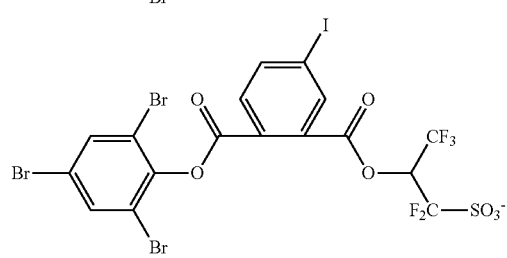
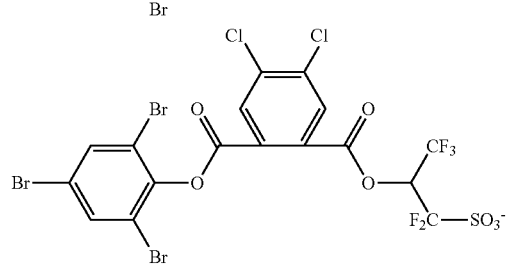
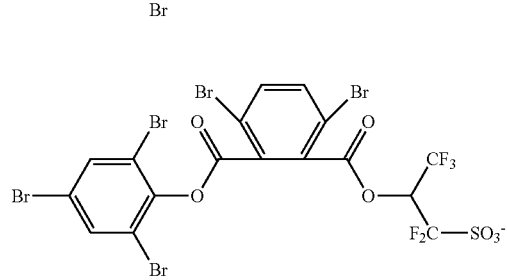
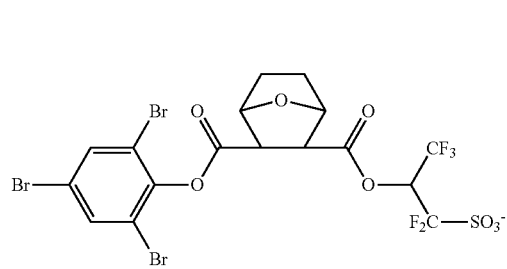
-continued
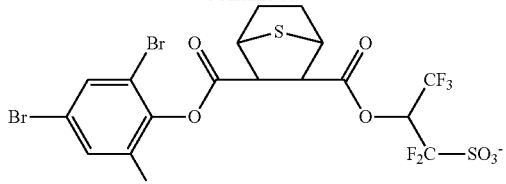
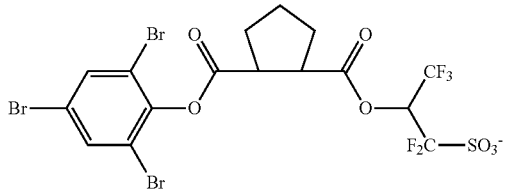
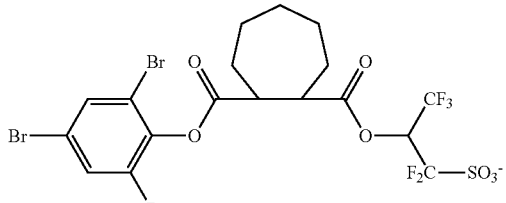
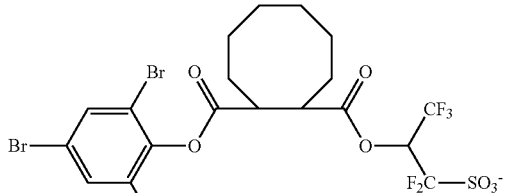
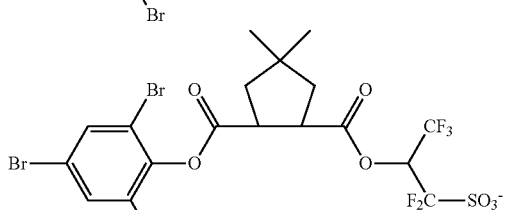
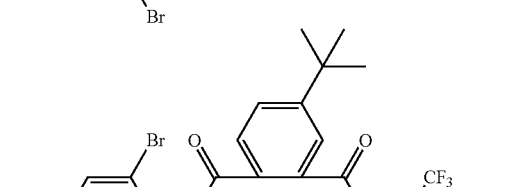
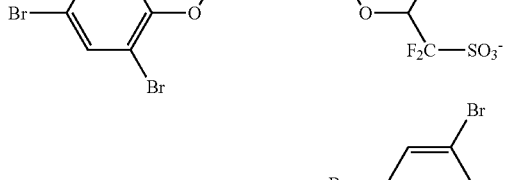
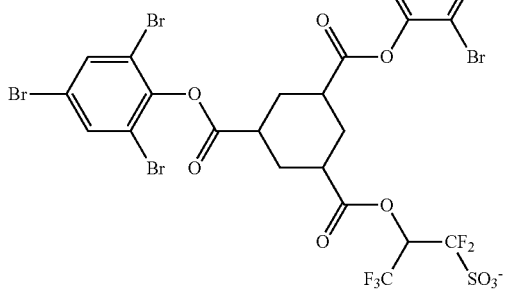

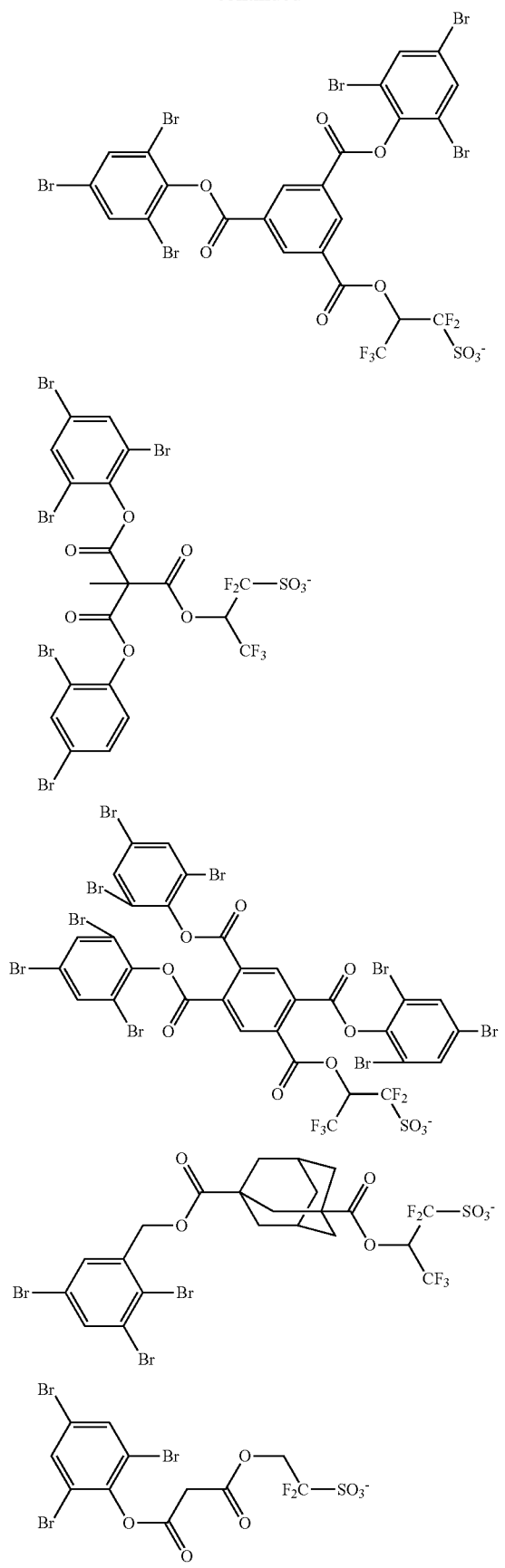
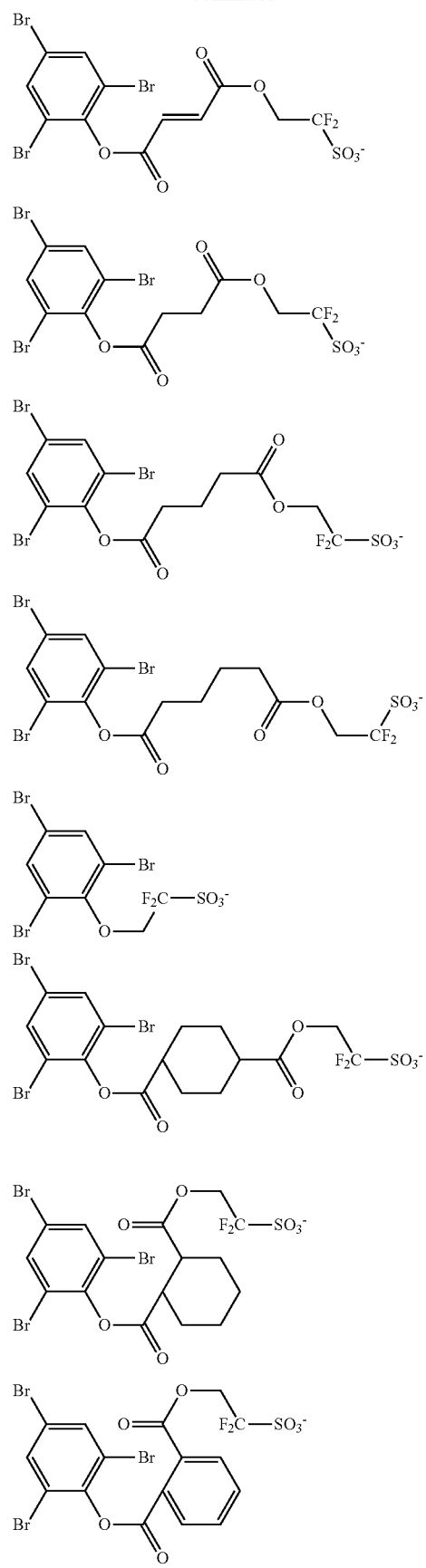

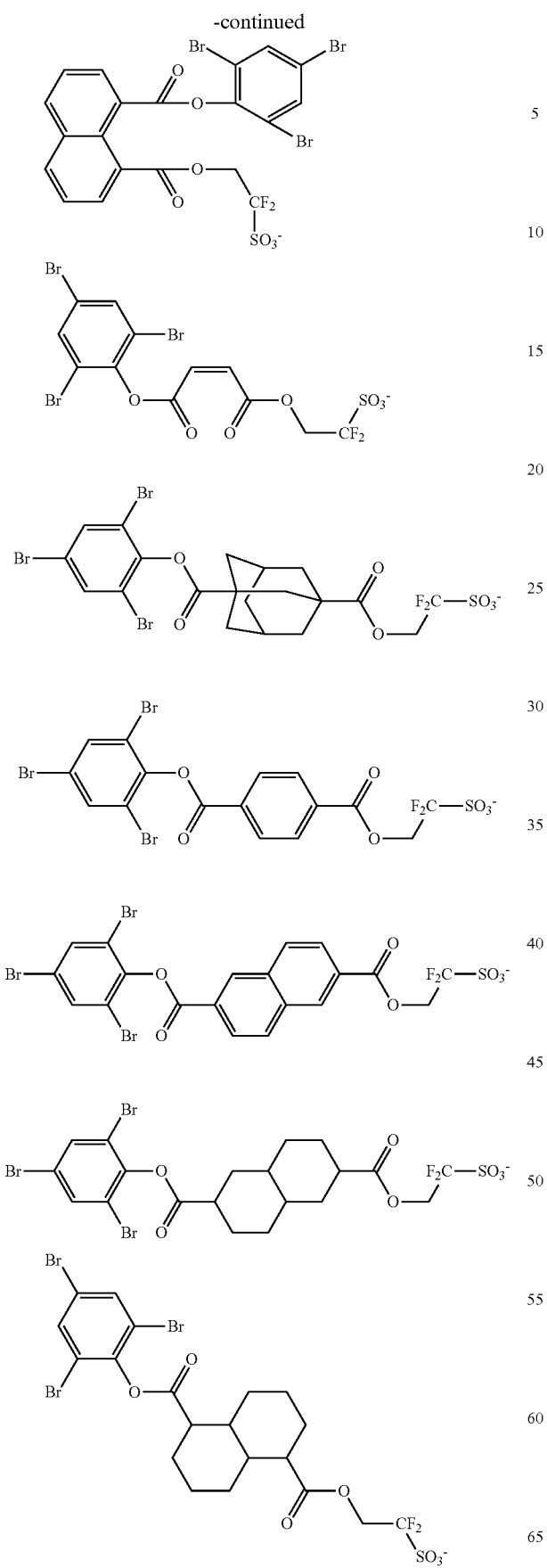
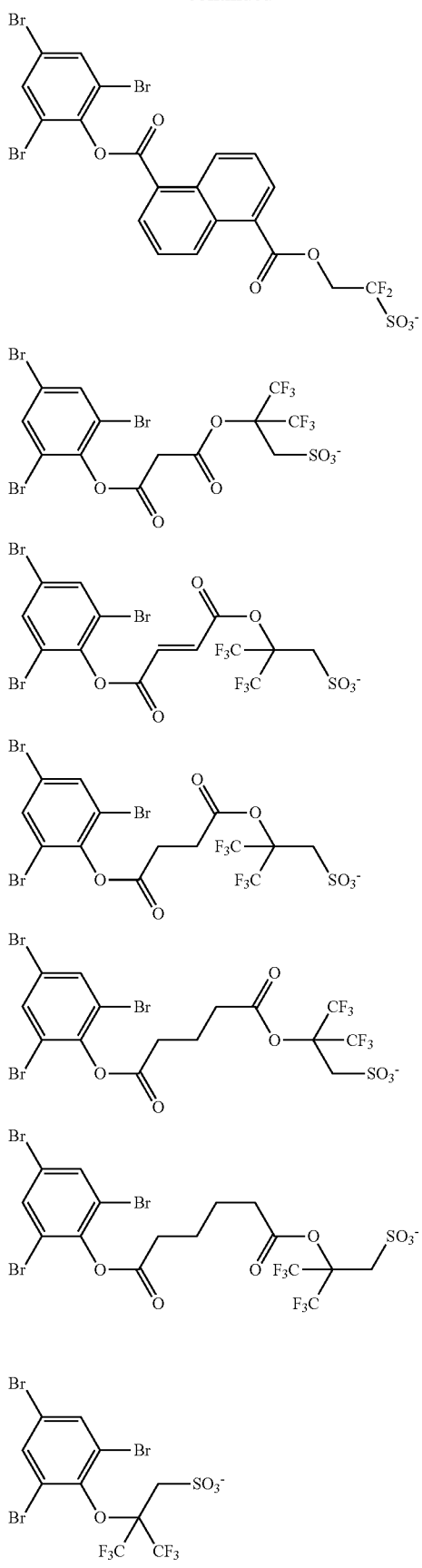

-continued
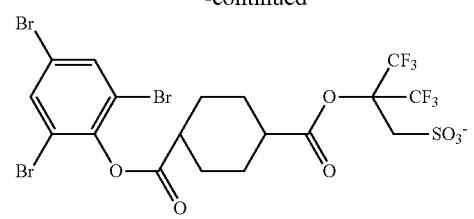
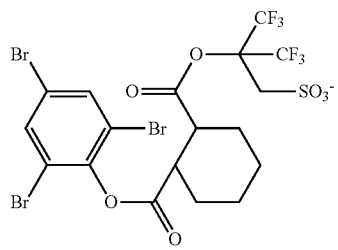
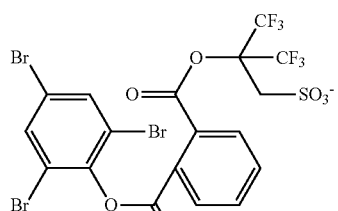
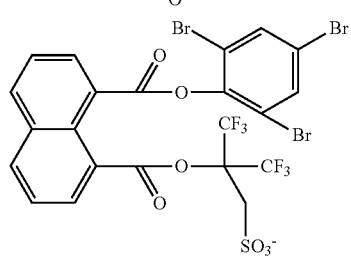
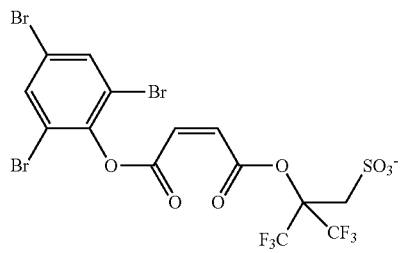
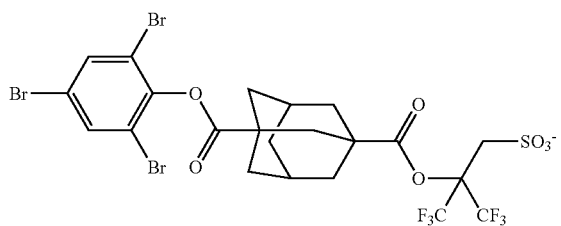
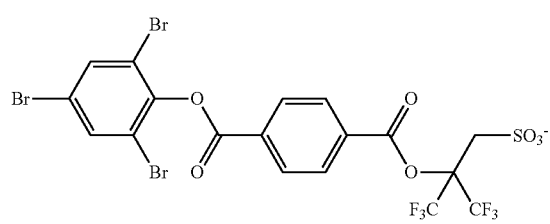
-continued
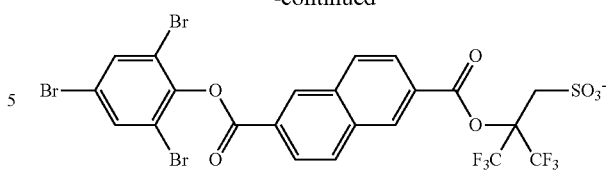
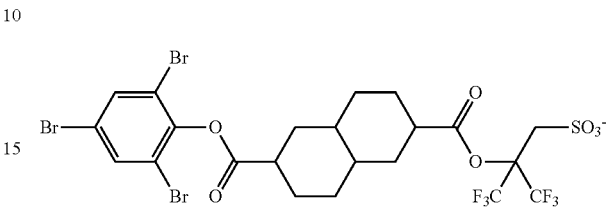
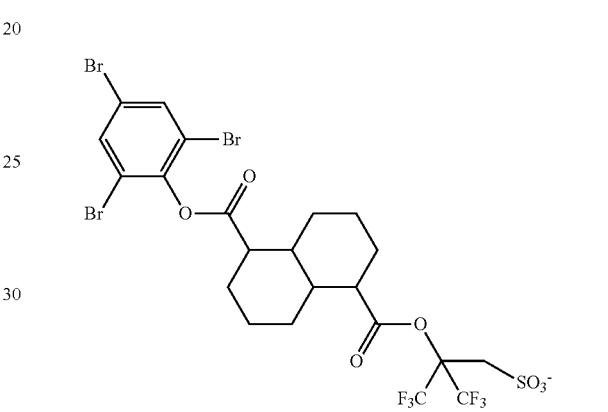
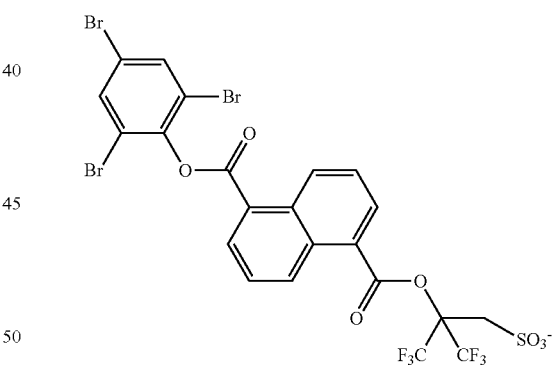
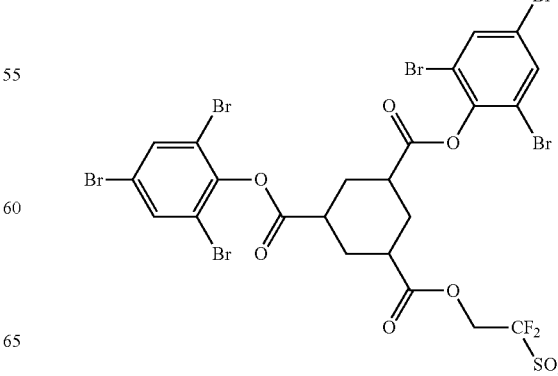

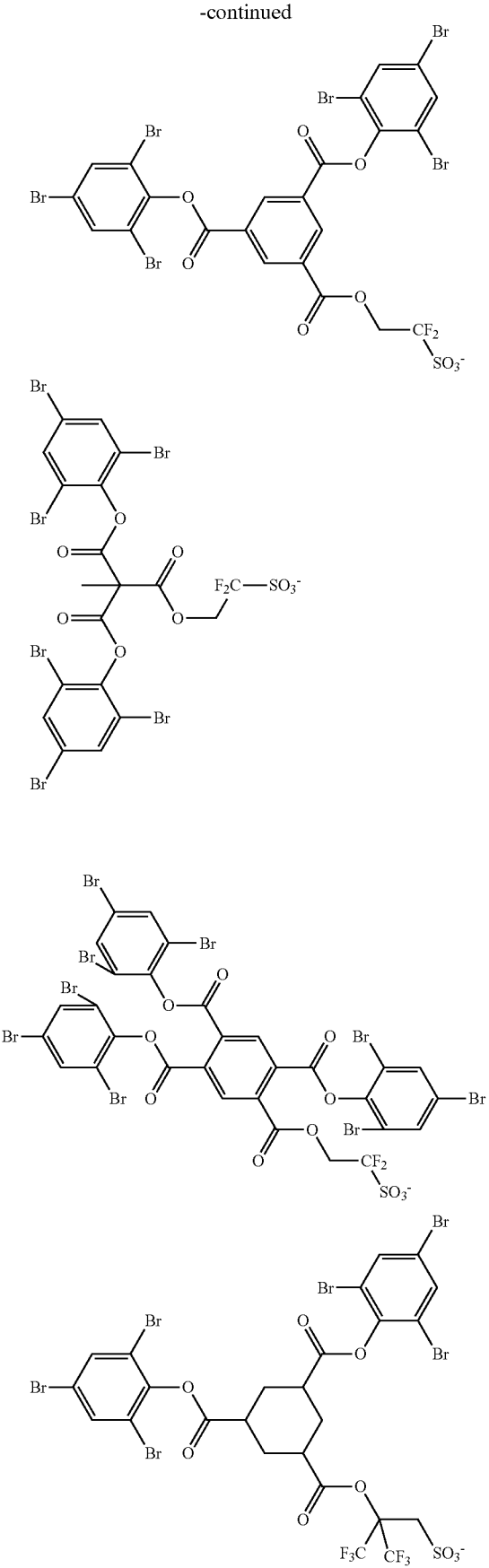
Of the sulfonic acid metal salts having formula (1), a barium salt having the following formula (2) is preferred in that because of its large atomic number and possession of more elections, the element emits more secondary elections upon exposure to EB or EUV and is thus more effective for providing the resist film with a higher sensitivity.
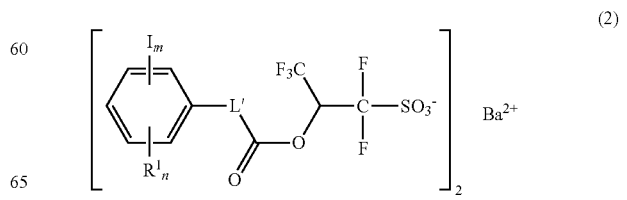

In formula (2), $R^1$, m and n are as defined and exemplified above. L' is a single bond, or a $C_1$-$C_{12}$ alkanediyl, $C_2$-$C_{12}$ alkenediyl or $C_6$-$C_{10}$ arylene group which may contain an ether bond or ester bond. The alkanediyl and alkenediyl groups may be straight, branched or cyclic.

In the resist composition, the sulfonic acid metal salt is preferably added in an amount of 0.01 to 100 parts, more preferably 0.1 to 50 parts by weight per 100 parts by weight of the base resin.

The sulfonic acid metal salt having formula (1) may be synthesized, for example, by neutralization reaction or salt exchange reaction of a hydroxide, halide, carbonate, sulfate, carboxylate or β-keto-ester salt of sodium, magnesium, potassium, calcium, rubidium, strontium, yttrium, cesium, barium or cerium with an ammonium salt of an α-fluorinated fluorosulfonic acid having a plurality of iodine or bromine atoms substituted thereon.

Base Resin

The base resin is defined as comprising recurring units having an acid labile group. The recurring units containing an acid labile group are preferably units having the formula (a1) or units having the formula (b2), which are simply referred to as units (a1) or (a2).

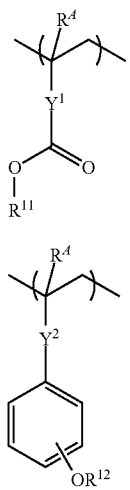

(a1)

(a2)

In formulae (a1) and (a2), $R^A$ is each independently hydrogen or methyl. $R^{11}$ and $R^{12}$ each are an acid labile group. $Y^1$ is a single bond, or a $C_1$-$C_{15}$ linking group having at least one of ester bond, lactone ring, phenylene moiety and naphthylene moiety. $Y^2$ is a single bond, ester bond or amide bond.

Examples of the monomer from which recurring units (a1) are derived are shown below, but not limited thereto. $R^A$ and $R^{11}$ are as defined above.

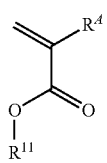 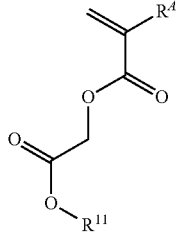 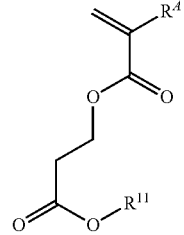

-continued

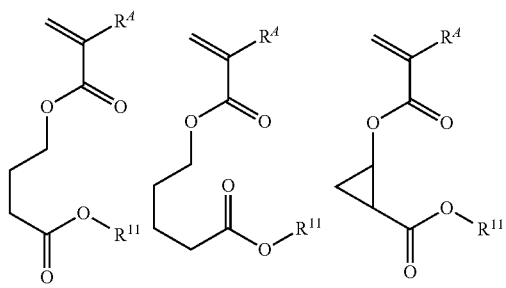

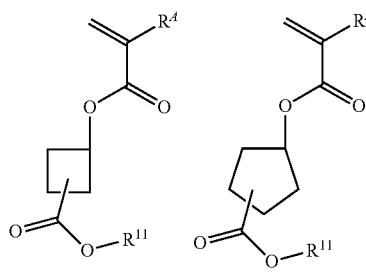

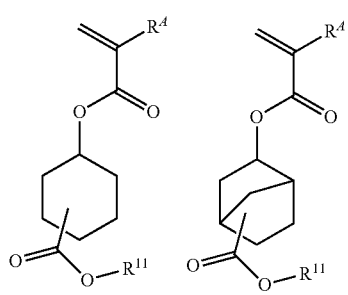

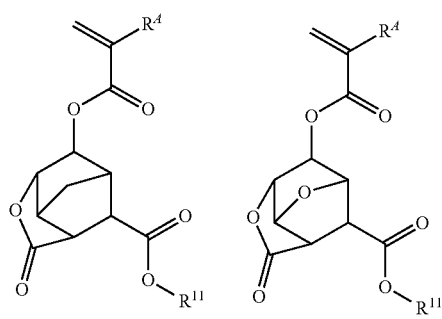

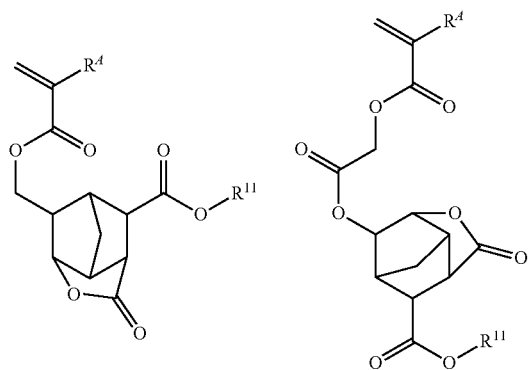

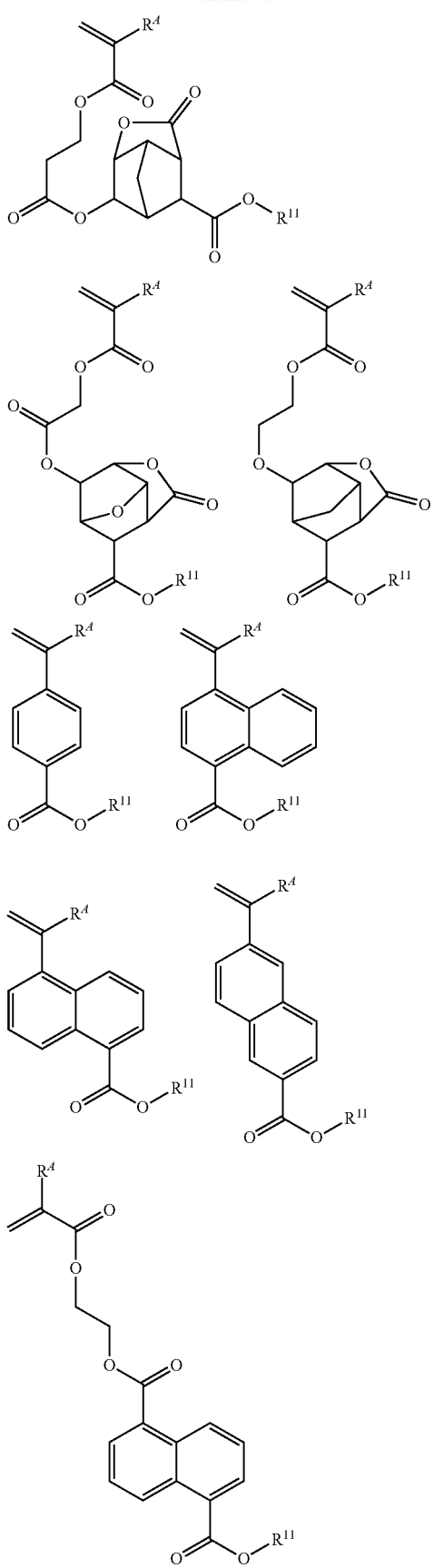
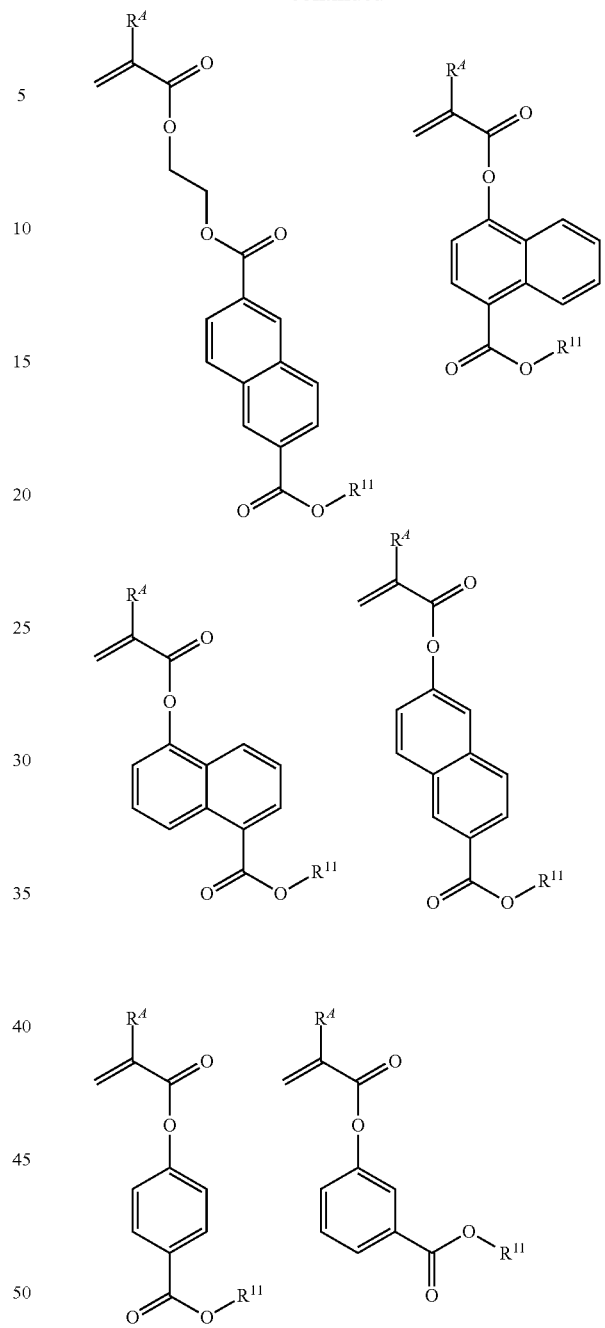
Examples of the monomer from which recurring units (a2) are derived are shown below, but not limited thereto. $R^A$ and $R^{12}$ are as defined above.
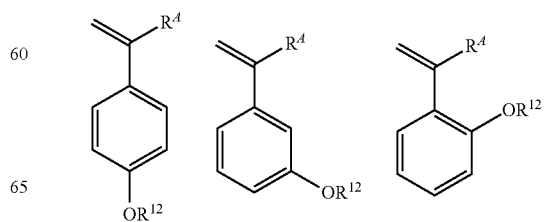

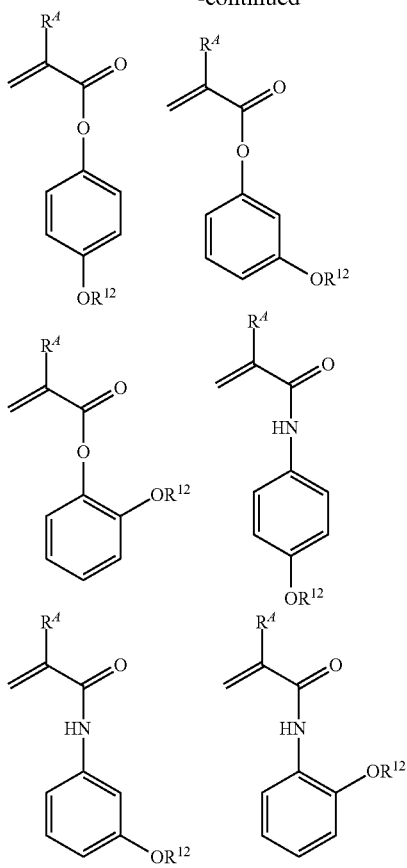

The acid labile groups represented by $R^{11}$ and $R^{12}$ in the recurring units (a1) and (a2) may be selected from a variety of such groups. Typical of the acid labile group are groups of the following formulae (AL-1) to (AL-3).

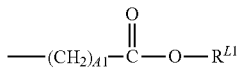    (A-1)

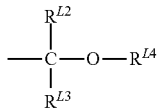    (A-2)

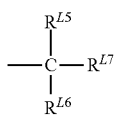    (A-3)

In formula (A-1), $R^{L1}$ is a $C_4$-$C_{20}$, preferably $C_4$-$C_{15}$, tertiary alkyl group which may contain a heteroatom, a trialkylsilyl group in which each alkyl moiety has 1 to 6 carbon atoms, a $C_4$-$C_{20}$ alkyl group containing a carbonyl moiety or ester bond, or a group of formula (A-3). A1 is an integer of 0 to 6.

The optionally heteroatom-containing tertiary alkyl group may be branched or cyclic, and examples thereof include t-butyl, t-pentyl, 1,1-diethylpropyl, 1-ethylcyclopentyl, 1-butylcyclopentyl, 1-ethylcyclohexyl, 1-butylcyclohexyl, 1-ethyl-2-cyclopentyl, 1-ethyl-2-cyclohexenyl, 2-methyl-2-adamantyl, 2-tetrahydropyranyl, and 2-tetrahydrofuranyl. Exemplary trialkylsilyl groups are trimethylsilyl, triethylsilyl, and dimethyl-t-butylsilyl. The alkyl group containing carbonyl or ester bond may be straight, branched or cyclic, and examples thereof include 3-oxocyclohexyl, 4-methyl-2-oxooxan-4-yl, and 5-methyl-2-oxooxolan-5-yl.

Examples of the acid labile group having formula (A-1) include t-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 2-tetrahydropyranyloxycarbonylmethyl, and 2-tetrahydrofuranyloxycarbonylmethyl groups.

Of the acid labile groups having formula (A-1), groups having the formulae (A-1)-1 to (A-1)-10 are also preferred.

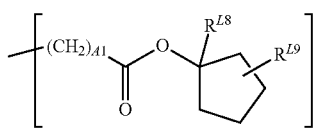    (A-1)-1

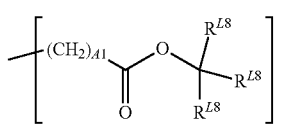    (A-1)-2

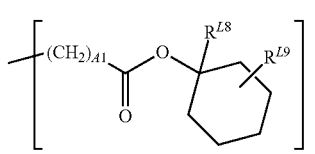    (A-1)-3

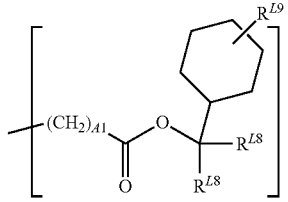    (A-1)-4

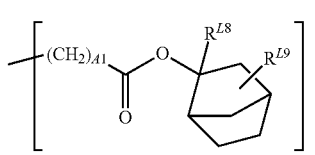    (A-1)-5

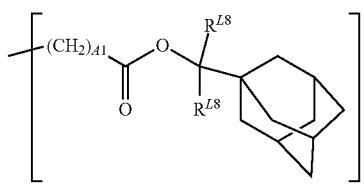    (A-1)-6

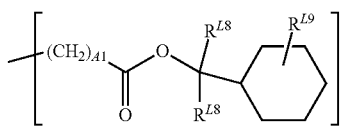    (A-1)-7

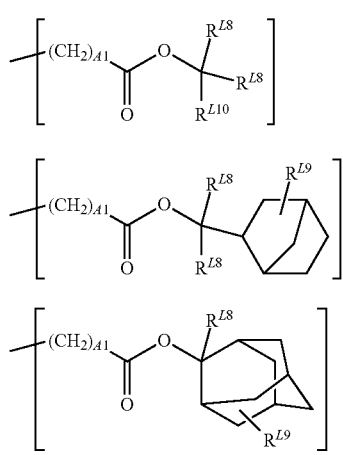

(A-1)-8

(A-1)-9

(A-1)-10

Herein A1 is as defined above. $R^{L8}$ is each independently a $C_1$-$C_{10}$ alkyl or $C_6$-$C_{20}$ aryl group, $R^{L9}$ is hydrogen or a $C_1$-$C_{10}$ alkyl group, $R^{L10}$ is each independently a $C_2$-$C_{10}$ alkyl or $C_6$-$C_{20}$ aryl group. The alkyl group may be straight, branched or cyclic.

In formula (A-2), $R^{L2}$ and $R^{L3}$ each are hydrogen or a $C_1$-$C_{18}$, preferably $C_1$-$C_{10}$, alkyl group. The alkyl group may be straight, branched or cyclic, and examples thereof include methyl, ethyl, propyl, isopropyl, n-butyl, s-butyl, t-butyl, cyclopentyl, cyclohexyl, 2-ethylhexyl, and n-octyl. $R^{L4}$ is a $C_1$-$C_{18}$, preferably $C_1$-$C_{10}$, monovalent hydrocarbon group which may contain a heteroatom such as oxygen. The monovalent hydrocarbon group may be straight, branched or cyclic. Examples of the monovalent hydrocarbon group include $C_1$-$C_{18}$ alkyl groups and substituted forms of such alkyl groups in which some hydrogen is replaced by hydroxyl, alkoxy, oxo, amino, alkylamino or the like. Examples of the substituted alkyl group are shown below.

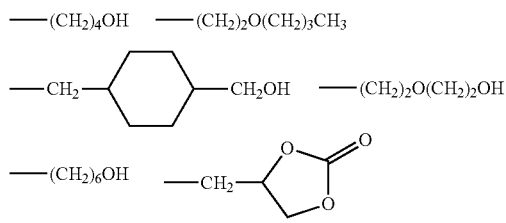

A pair of $R^{L2}$ and $R^{L3}$, $L^{L2}$ and $R^{L4}$, or $R^{L3}$ and $R^{L4}$ may bond together to form a ring with the carbon atom or the carbon and oxygen atoms to which they are attached. Each pair of $R^{L2}$ and $R^{L3}$, $L^{L2}$ and $R^{L4}$, or $R^{L3}$ and $R^{L4}$ is a straight or branched alkanediyl group of 1 to 18 carbon atoms, preferably 1 to 10 carbon atoms when they form a ring. The ring preferably has 3 to 10 carbon atoms, more preferably 4 to 10 carbon atoms.

Of the acid labile groups of formula (A-2), the straight and branched ones are exemplified by groups having the following formulae (A-2)-1 to (A-2)-69, but not limited thereto.

—$CH_2$—O—$CH_3$ (A-2)-1

—$CH_2$—O—$CH_2$—$CH_3$ (A-2)-2

—$CH_2$—O—$(CH_2)_2$—$CH_3$ (A-2)-3

—$CH_2$—O—$(CH_2)_3$—$CH_3$ (A-2)-4

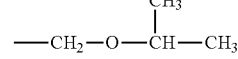 (A-2)-5

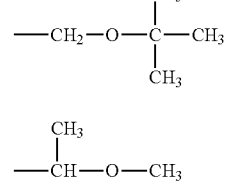 (A-2)-6

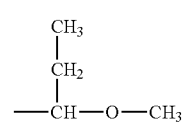 (A-2)-7

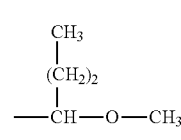 (A-2)-8

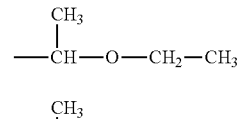 (A-2)-9

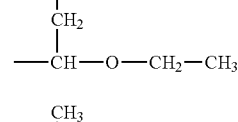 (A-2)-10

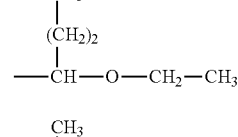 (A-2)-11

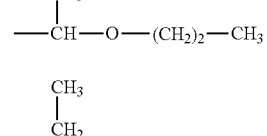 (A-2)-12

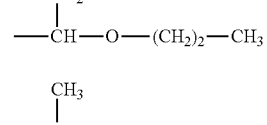 (A-2)-13

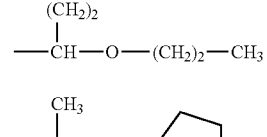 (A-2)-14

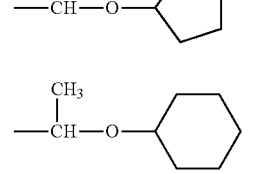 (A-2)-15

(A-2)-16

 (A-2)-17

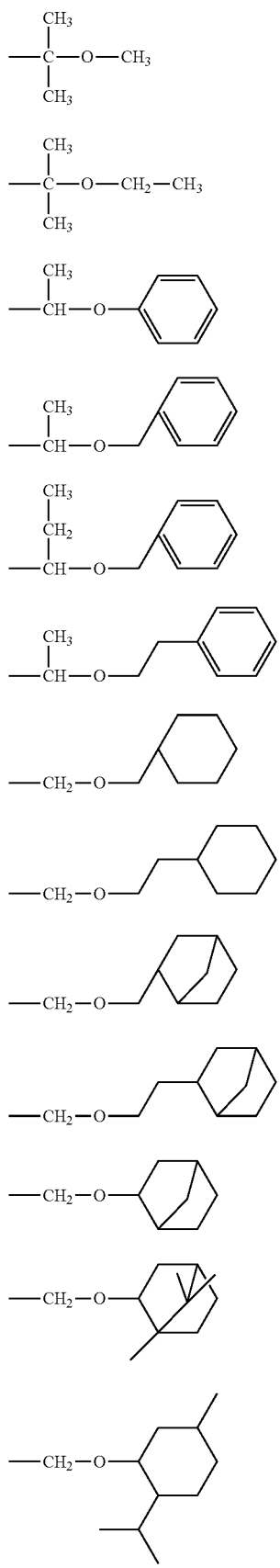
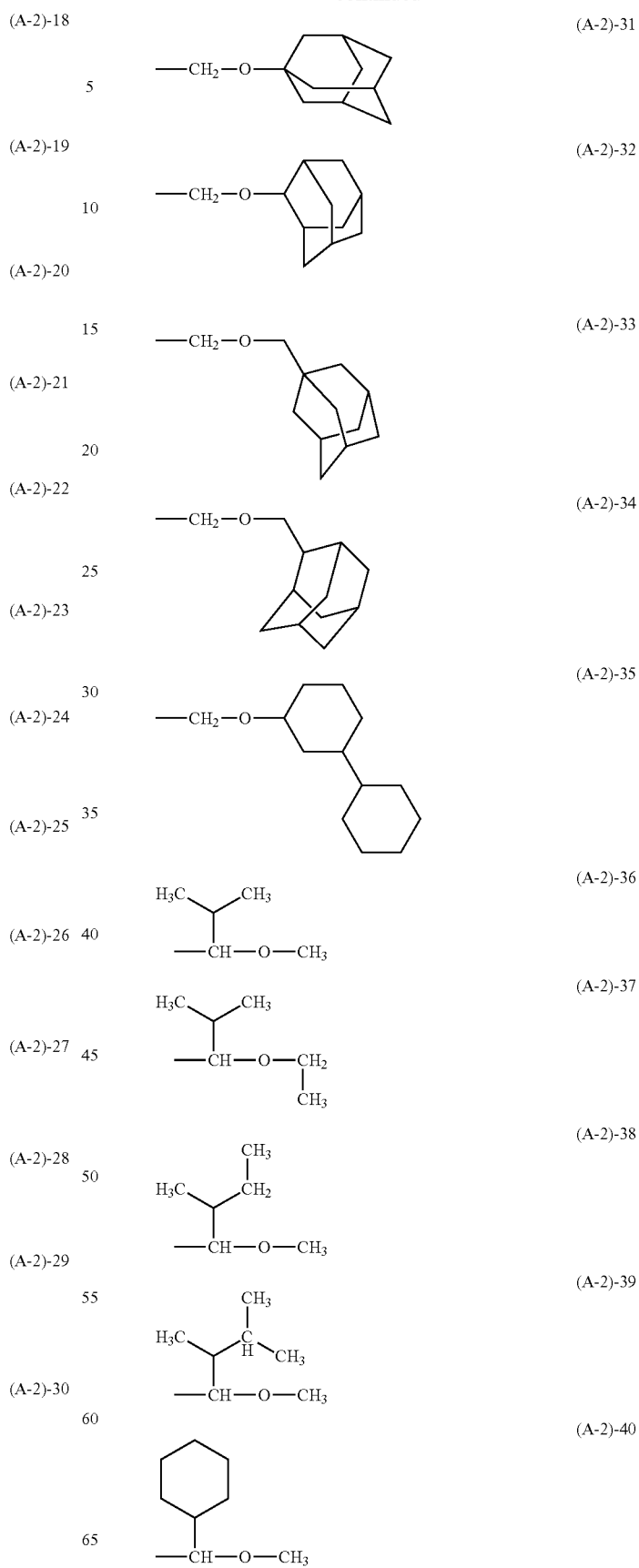

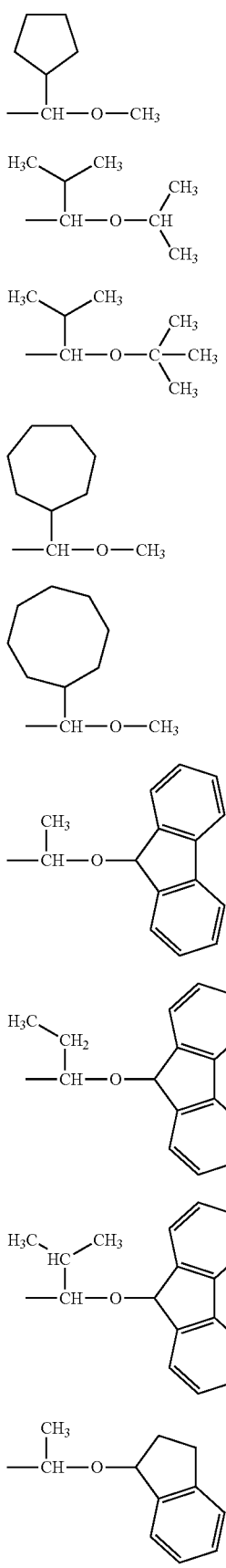
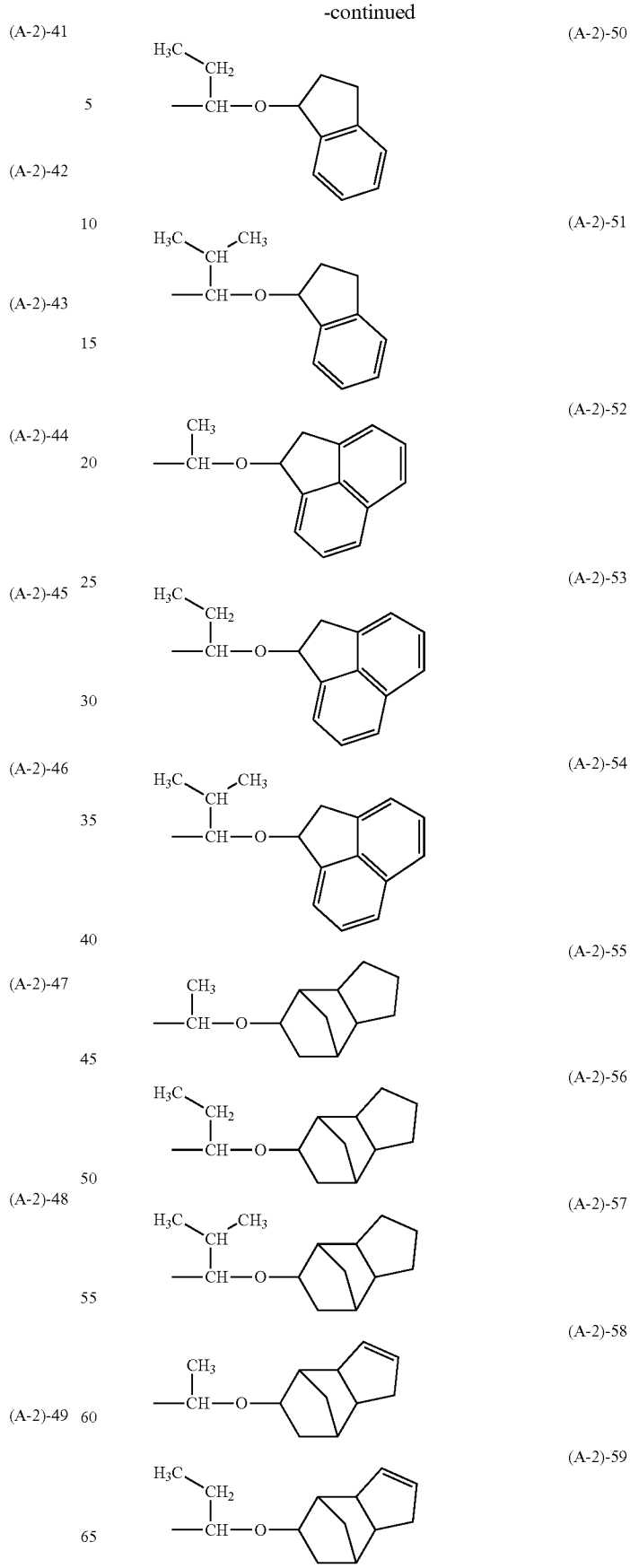

(A-2)-60 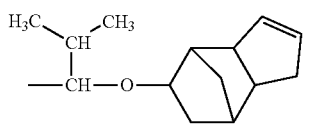

(A-2)-61 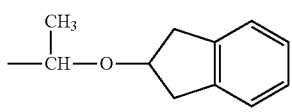

(A-2)-62 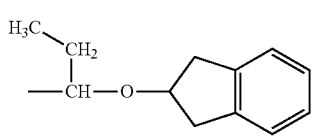

(A-2)-63 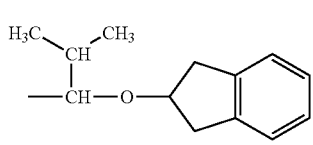

(A-2)-64 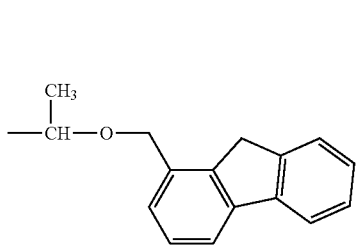

(A-2)-65 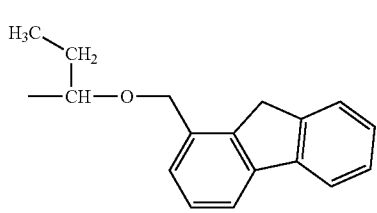

(A-2)-66 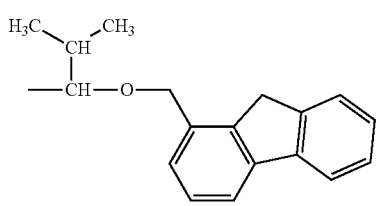

(A-2)-67 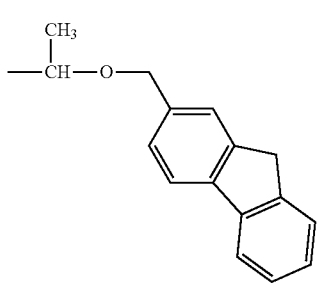

(A-2)-68 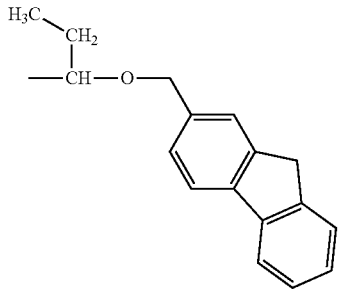

(A-2)-69 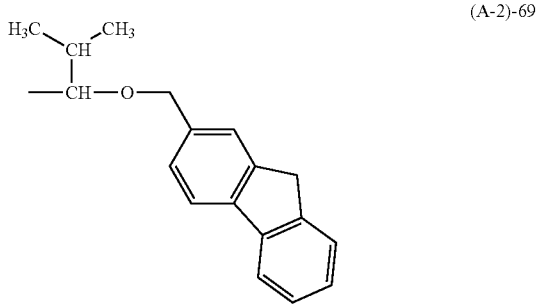

Of the acid labile groups of formula (A-2), the cyclic ones are, for example, tetrahydrofuran-2-yl, 2-methyltetrahydrofuran-2-yl, tetrahydropyran-2-yl, and 2-methyltetrahydropyran-2-yl.

Other examples of acid labile groups include those of the following formula (A-2a) or (A-2b) while the polymer may be crosslinked within the molecule or between molecules with these acid labile groups.

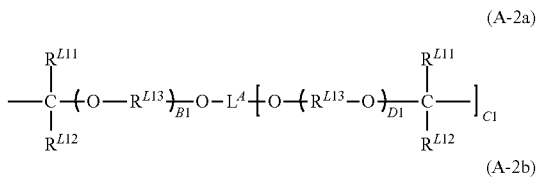

(A-2a)

(A-2b)

Herein $R^{L11}$ and $R^{L12}$ each are hydrogen or a $C_1$-$C_8$ alkyl group which may be straight, branched or cyclic. $R^{L11}$ and $R^{L12}$, taken together, may form a ring with the carbon atom to which they are attached, and a pair of $R^{L13}$ and $R^{L12}$ is a straight or branched $C_1$-$C_8$ alkanediyl group when they form a ring. $R^{L13}$ is independently a $C_1$-$C_{10}$ alkanediyl group which may be straight, branched or cyclic. Each of B1 and D1 is an integer of 0 to 10, preferably 0 to 5, and C1 is an integer of 1 to 7, preferably 1 to 3.

$L^A$ is a (C1+1)-valent aliphatic or alicyclic saturated hydrocarbon group, aromatic hydrocarbon group or heterocyclic group having 1 to 50 carbon atoms, in which at least one carbon may be substituted by a heteroatom-containing moiety or in which at least one carbon-bonded hydrogen atom may be substituted by a hydroxyl, carboxyl, acyl moiety or fluorine atom. Preferably, $L^A$ is a $C_1$-$C_{20}$ alkanediyl, alkanetriyl or alkanetetrayl group, or $C_6$-$C_{30}$ arylene group. The alkanediyl, alkanetriyl and alkanetetrayl groups may be straight, branched or cyclic. $L^B$ is —CO—O—, —NHCO—O— or —NHCONH—.

The crosslinking acetal groups of formulae (A-2a) and (A-2b) are exemplified by the following formulae (A-2)-70 through (A-2)-77.

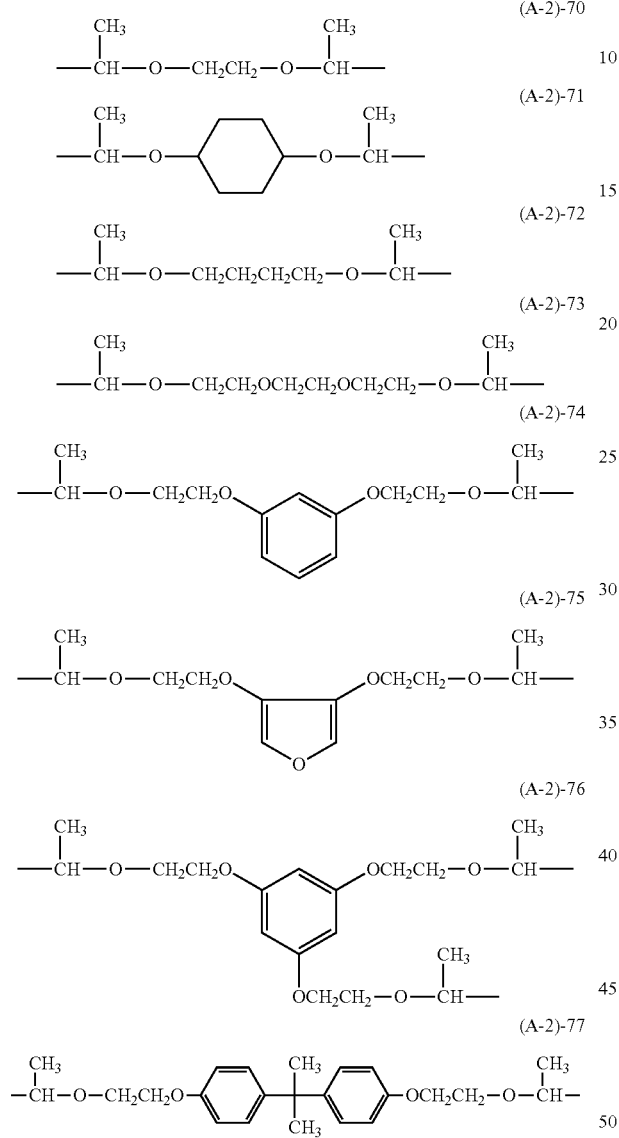

In formula (A-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon group may be straight, branched or cyclic. Examples include $C_1$-$C_{20}$ alkyl and $C_2$-$C_{20}$ alkenyl groups. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Exemplary tertiary alkyl groups of formula (A-3) include t-butyl, triethylcarbyl, 1-ethylnorbornyl, 1-methylcyclohexyl, 1-ethylcyclopentyl, 2-(2-methyl)adamantyl, 2-(2-ethyl)adamantyl, and t-pentyl.

Other exemplary tertiary alkyl groups include those of the following formulae (A-3)-1 to (A-3)-18.

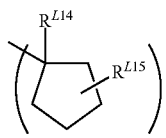
(A-3)-1

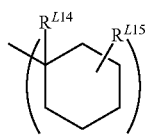
(A-3)-2

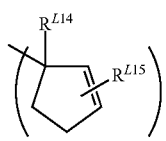
(A-3)-3

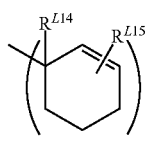
(A-3)-4

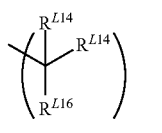
(A-3)-5

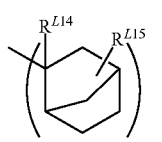
(A-3)-6

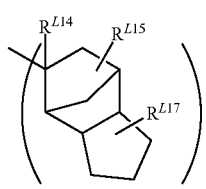
(A-3)-7

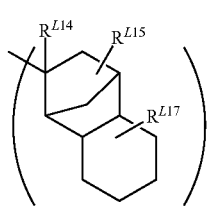
(A-3)-8

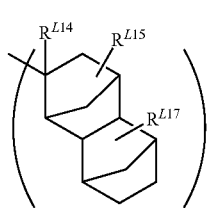
(A-3)-9

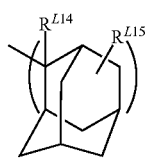
(A-3)-10

(A-3)-11 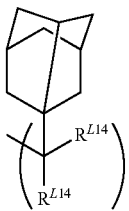

(A-3)-12

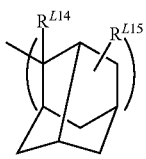 (A-3)-18

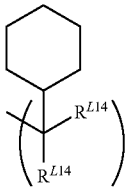
(A-3)-13

(A-3)-14

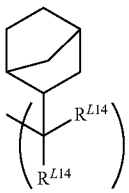

Herein $R^{L14}$ is each independently a $C_1$-$C_8$ alkyl group or $C_6$-$C_{20}$ aryl group, $R^{L15}$ and $R^{L17}$ are each independently hydrogen or a $C_1$-$C_{20}$ alkyl group, $R^{L16}$ is a $C_6$-$C_{20}$ aryl group. The alkyl group may be straight, branched or cyclic. Typical of the aryl group is phenyl.

Also useful are acid labile groups having the following formulae (A-3)-19 and (A-3)-20. The polymer may be crosslinked within the molecule or between molecules with these acid labile groups.

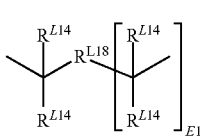 (A-3)-19

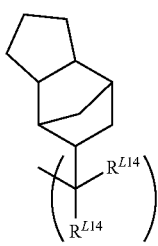

(A-3)-15

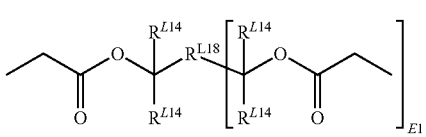 (A-3)-20

Herein $R^{L14}$ is as defined above, $R^{L18}$ is a (E1+1)-valent $C_1$-$C_{20}$ aliphatic hydrocarbon group or (E1+1)-valent $C_6$-$C_{20}$ aromatic hydrocarbon group, which may contain a heteroatom such as oxygen, sulfur or nitrogen. The aliphatic hydrocarbon group may be straight, branched or cyclic. E1 is an integer of 1 to 3.

Examples of the monomer from which recurring units having an acid labile group of formula (A-3) are derived include (meth)acrylates of exo-form structure having the formula (A-3)-21.

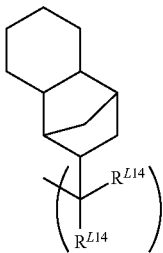

(A-3)-16

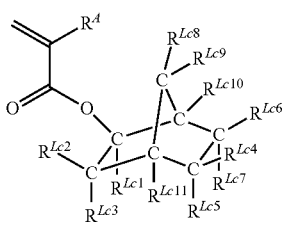 (A-3)-21

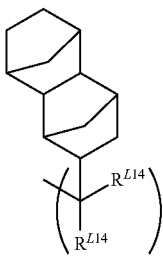

(A-3)-17

Herein $R^A$ is as defined above. $R^{Lc1}$ is a $C_1$-$C_8$ alkyl group or an optionally substituted $C_6$-$C_{20}$ aryl group. The alkyl group may be straight, branched or cyclic. $R^{Lc2}$ to $R^{Lc7}$, $R^{Lc10}$ and $R^{Lc11}$ are each independently hydrogen or a $C_1$-$C_{15}$ monovalent hydrocarbon group which may contain a heteroatom. Typical of the heteroatom is oxygen. Suitable monovalent hydrocarbon groups include $C_1$-$C_{15}$ alkyl group and $C_6$-$C_{15}$ aryl groups. $R^{Lc8}$ and $R^{Lc9}$ are hydrogen. Alternatively, a pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$

and $R^{Lc9}$, $R^{Lc9}$ and $R^{Lc10}$, taken together, may form a ring with the carbon atom to which they are attached, and a ring-forming participant is a $C_1$-$C_{15}$ divalent hydrocarbon group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

The monomers from which recurring units having formula (A-3)-21 are derived are exemplified in U.S. Pat. No. 6,448,420 (JP-A 2000-327633). Illustrative non-limiting examples of suitable monomers are given below. $R^A$ is as defined above.

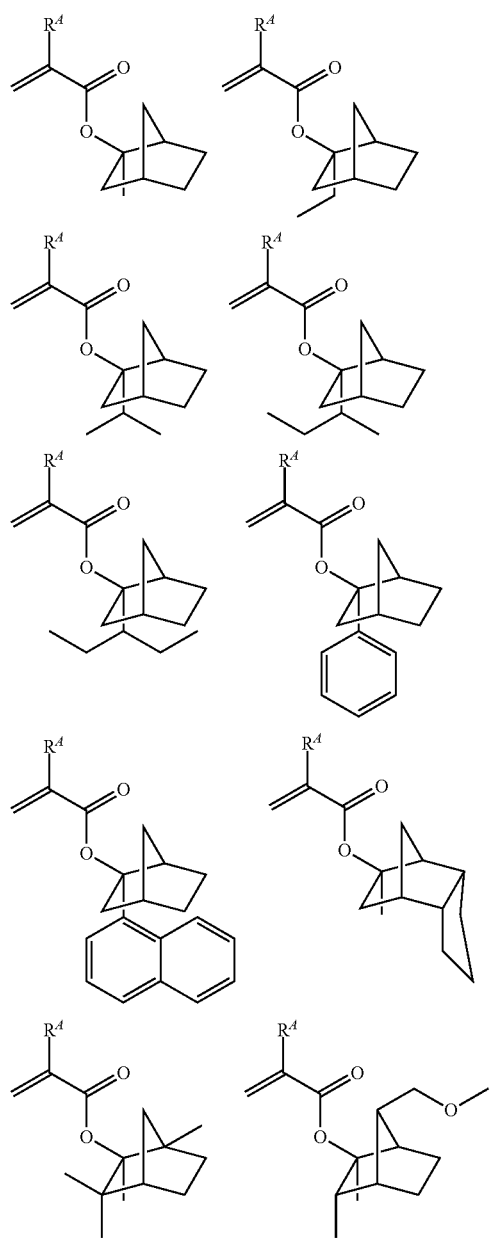

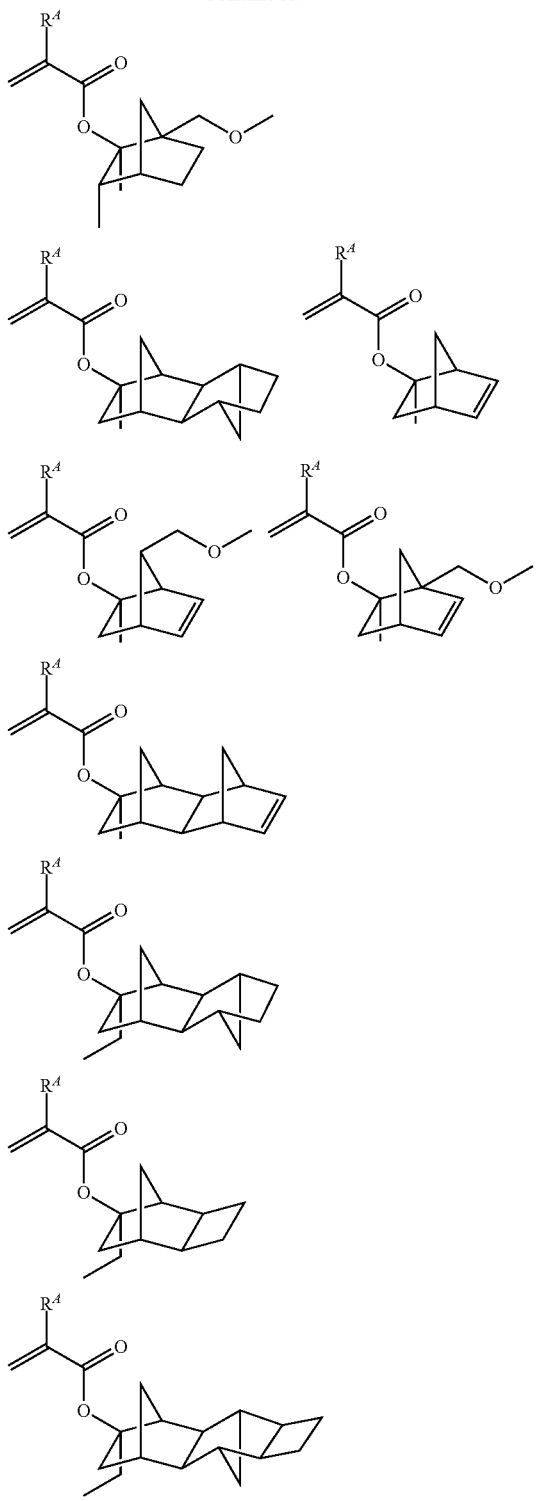

The monomers from which recurring units having an acid labile group of formula (A-3) are derived include (meth) acrylates having furandiyl, tehahydrofurandiyl or oxanorbornanediyl, represented by the formula (A-3)-22.

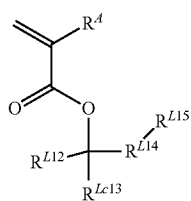
(A-3)-22

Herein $R^A$ is as defined above. $R^{Lc12}$ and $R^{Lc13}$ are each independently a $C_1$-$C_{10}$ monovalent hydrocarbon group, or $R^{Lc12}$ and $R^{Lc13}$, taken together, may form an aliphatic ring with the carbon atom to which they are attached. $R^{Lc14}$ is furandiyl, tetrahydrofurandiyl or oxanorbornanediyl. $R^{Lc15}$ is hydrogen or a $C_1$-$C_{10}$ monovalent hydrocarbon group which may contain a heteroatom. The monovalent hydrocarbon group may be straight, branched or cyclic, and examples thereof include $C_1$-$C_{10}$ alkyl groups.

Examples of the monomers from which recurring units having formula (A-3)-22 are derived are shown below, but not limited thereto. $R^A$ is as defined above.

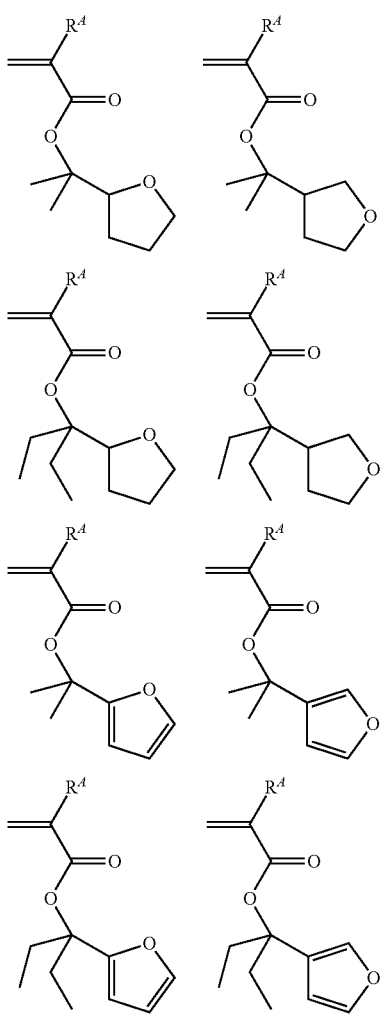

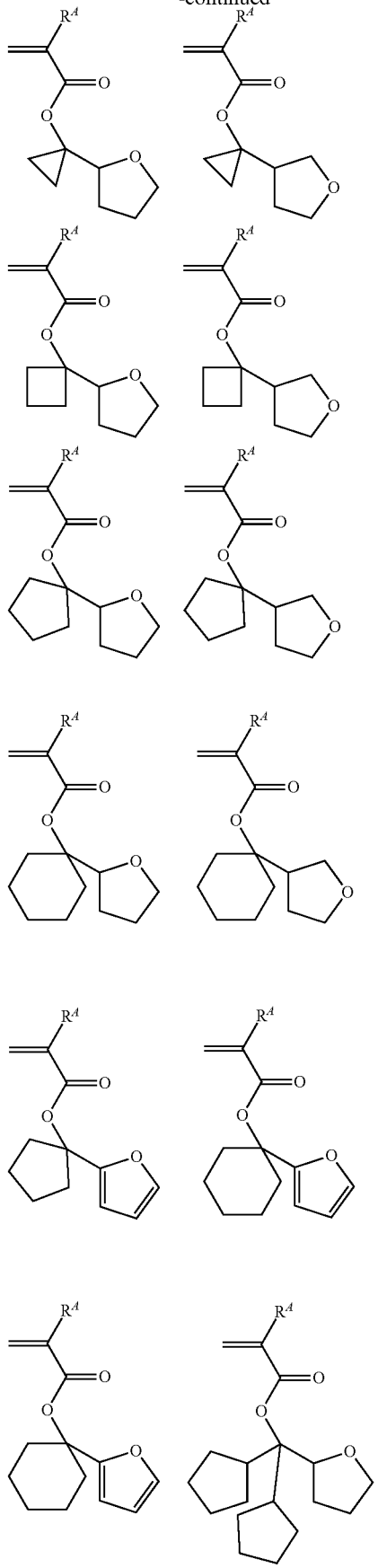

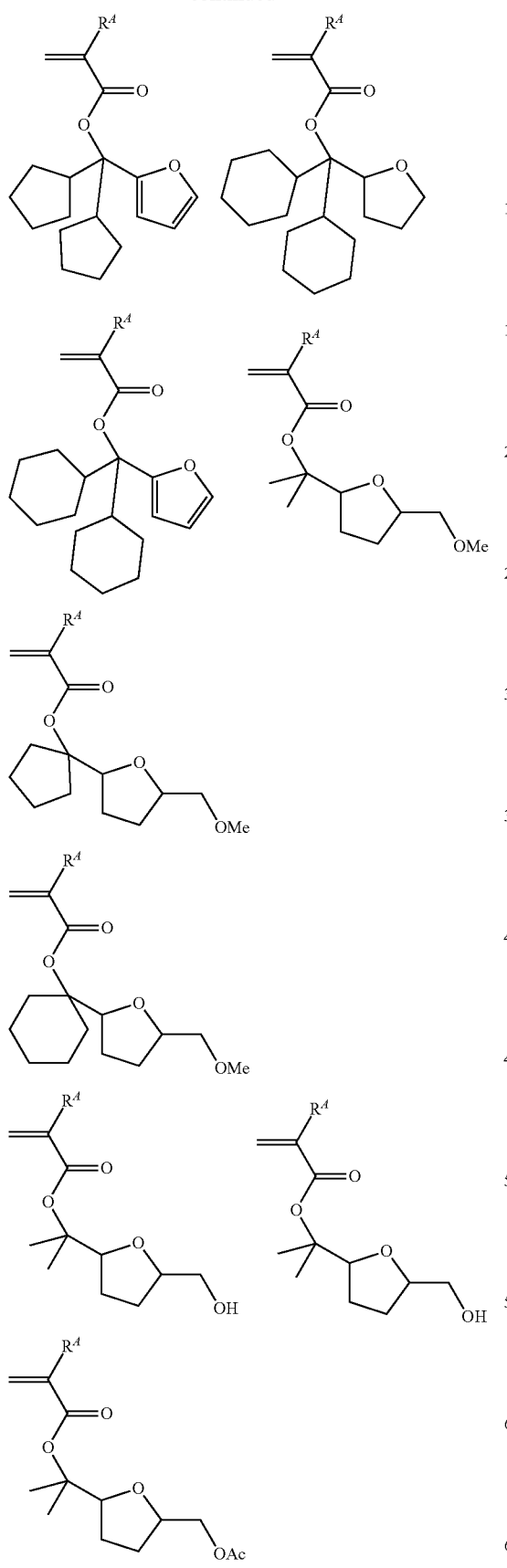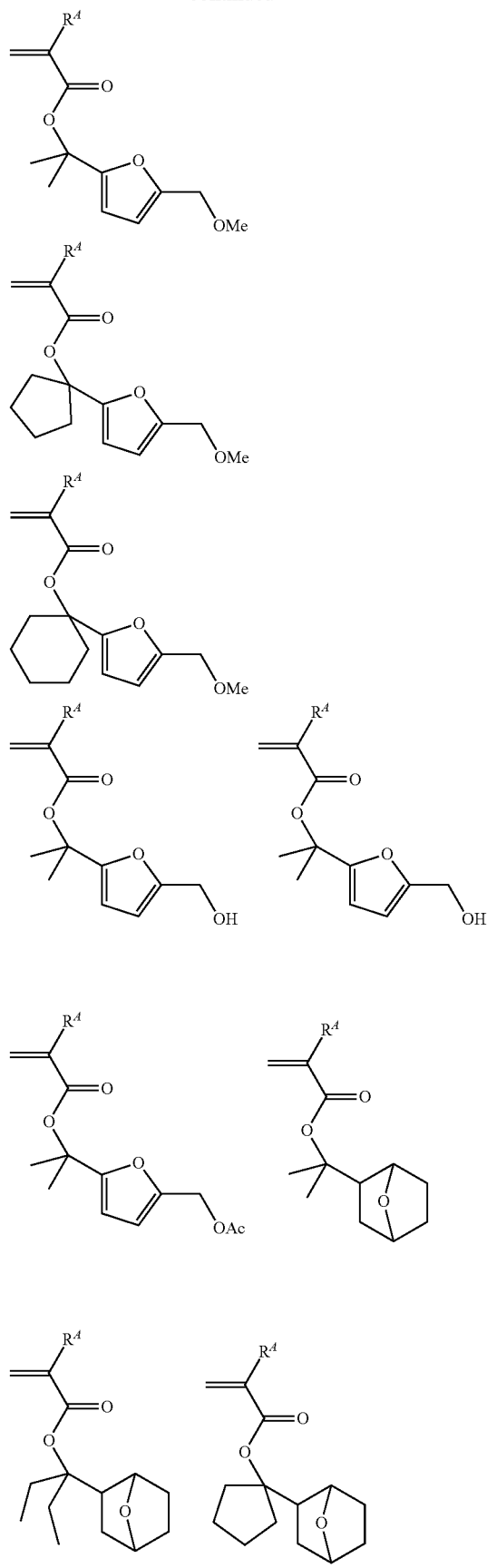

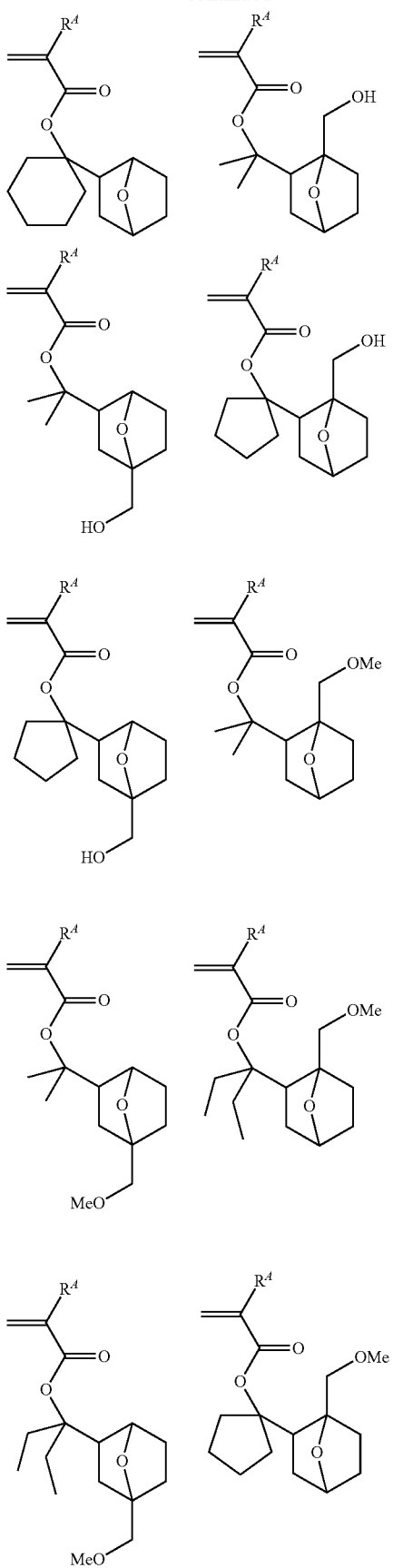
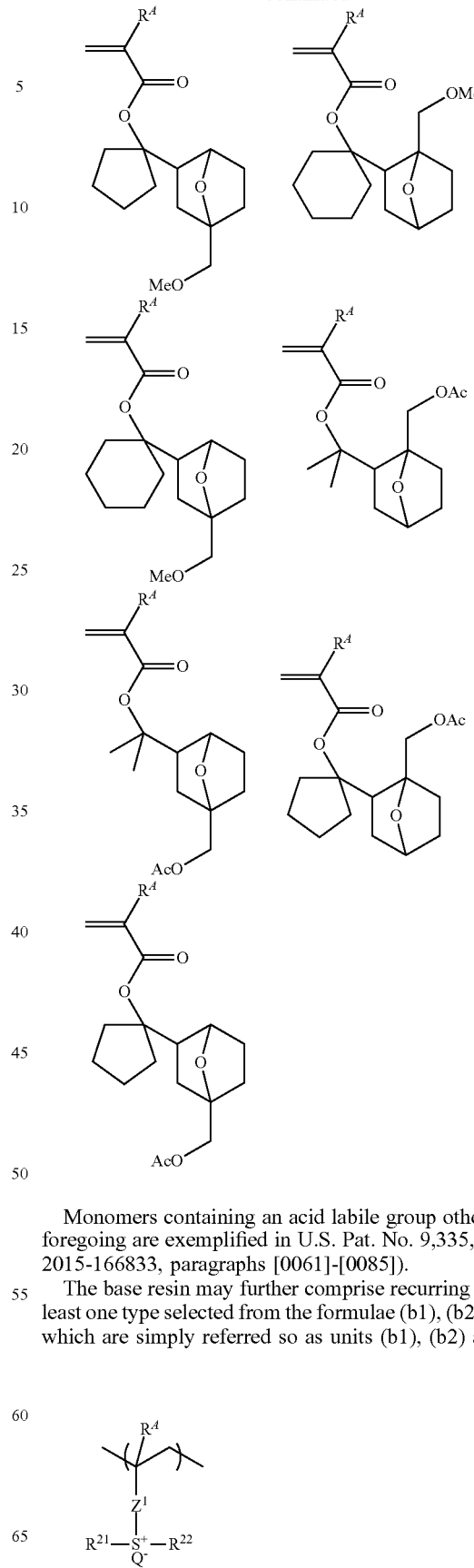
Monomers containing an acid labile group other than the foregoing are exemplified in U.S. Pat. No. 9,335,633 (JP-A 2015-166833, paragraphs [0061]-[0085]).
The base resin may further comprise recurring units of at least one type selected from the formulae (b1), (b2) and (b3), which are simply referred so as units (b1), (b2) and (b3).
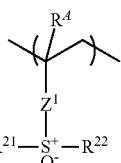
(b1)

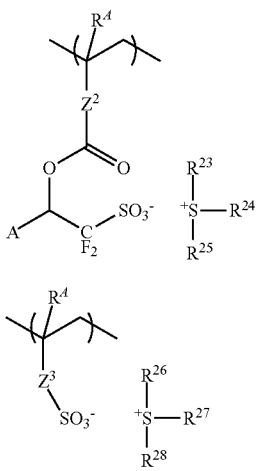

In formulae (b1) to (b3), $R^A$ is as defined above. $Z^1$ is a single bond, phenylene group, —O—$Z^{11}$—, —C(=O)—O—$Z^{11}$—, or —C(=O)—NH—$Z^{11}$—. $Z^2$ is a single bond, —C(=O)—O—$Z^{11}$—, or —C(=O)—NH—$Z^{11}$—. $Z^3$ is a single bond, methylene, ethylene, phenylene, fluorinated phenylene, —O—$Z^{11}$—, —C(=O)—O—$Z^{11}$—, or —C(=O)—NH—$Z^{11}$—; $Z^{11}$ is a $C_1$-$C_6$ alkanediyl group, phenylene group, or $C_2$-$C_{10}$ alkenediyl group, which may contain a carbonyl, ester bond, ether bond or hydroxyl moiety. The alkanediyl and alkenediyl groups may be straight, branched or cyclic.

In formulae (b1) to (b3), $R^{21}$ to $R^{28}$ are each independently a $C_1$-$C_{22}$ monovalent hydrocarbon group which may contain a heteroatom, a pair of $R^{21}$ and $R^{22}$ may bond together to form a ring with the sulfur atom to which they are attached, any two of $R^{23}$, $R^{24}$ and $R^{25}$ or any two of $R^{26}$, $R^{27}$ and $R^{28}$ may bond together to form a ring with the sulfur atom to which they are attached. A is hydrogen or trifluoromethyl.

The monovalent hydrocarbon group may be straight, branched or cyclic. Examples include $C_1$-$C_{20}$ alkyl, $C_2$-$C_{20}$ alkenyl, $C_2$-$C_{20}$ alkynyl, $C_6$-$C_{20}$ aryl, and $C_7$-$C_{20}$ aralkyl groups. In the foregoing groups, at least one (one or more or even all) hydrogen may be substituted by hydroxyl, carboxyl, halogen, cyano, amide, nitro, mercapto, sultone, sulfone moiety or sulfonium salt-containing moiety, or at least one carbon may be substituted by an ether bond, ester bond, carbonyl moiety, carbonate moiety or sulfonic acid ester bond.

The recurring units (b1) to (b3) function as an acid generator. The binding of the acid generator to the polymer backbone is effective for shortening the distance of acid diffusion and reducing LWR.

The inclusion of recurring units (b1), (b2) or (b3) in the base resin is effective for increasing the sensitivity of the resist film by the mechanism that the metal in the salt emits secondary electrons during exposure, which induce decomposition of the acid generator in unit (b1), (b2) or (b3). Although a sensitivity increase can be achieved by elevating the PEB temperature or prolonging the PEB time, the acid diffusion distance is increased in either case, resulting in exaggerated LWR. In contrast, the addition of the sulfonic acid metal salt having formula (1) ensures a high sensitivity and low LWR because of suppressed acid diffusion and a high efficiency of acid generation.

In formula (b1), $Q^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α- and β-positions as represented by the formula (K-2).

In formula (K-1), $R^{51}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2), $R^{52}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl and alkenyl groups may be straight, branched or cyclic.

Examples of the monomer from which recurring units (b1) are derived are shown below, but not limited thereto. $R^A$ and $Q^-$ are as defined above.

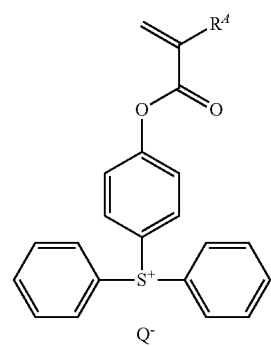

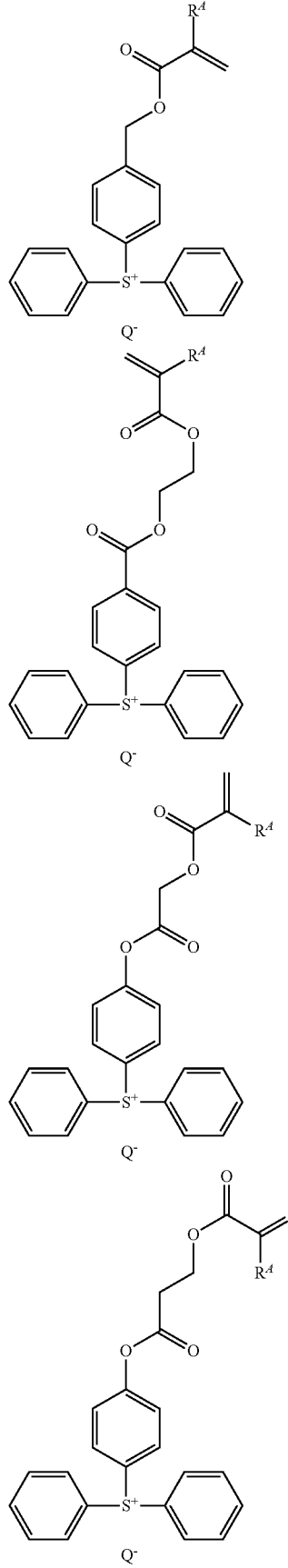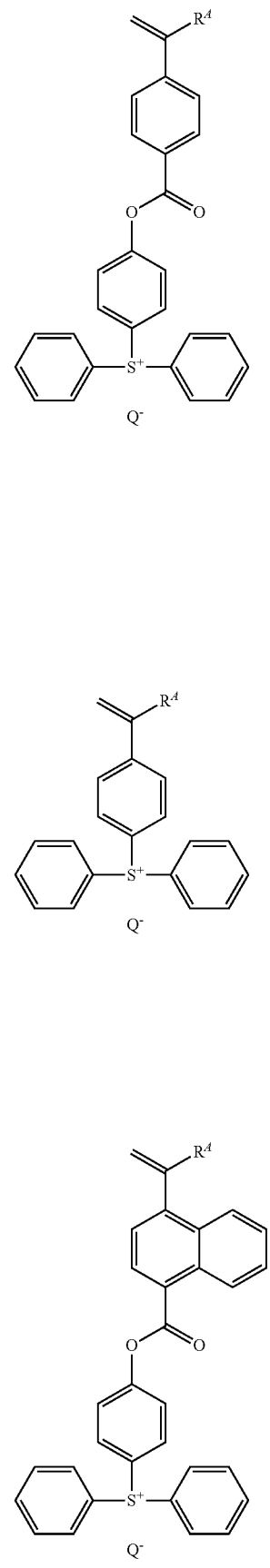

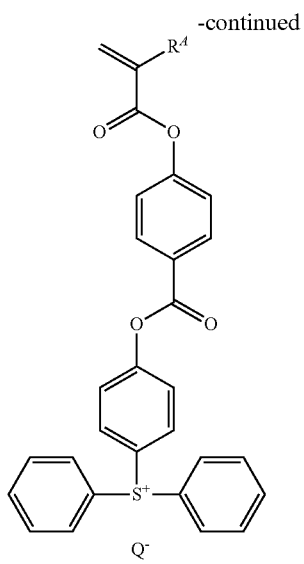
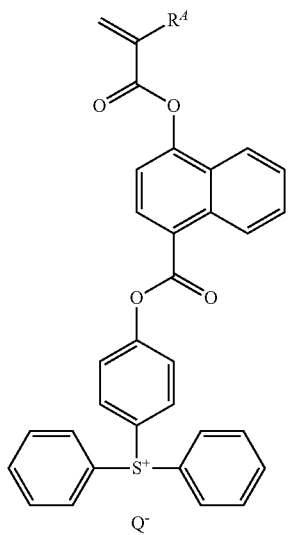
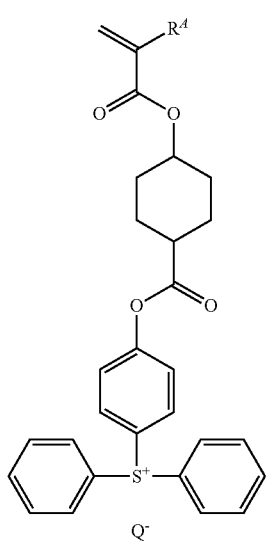
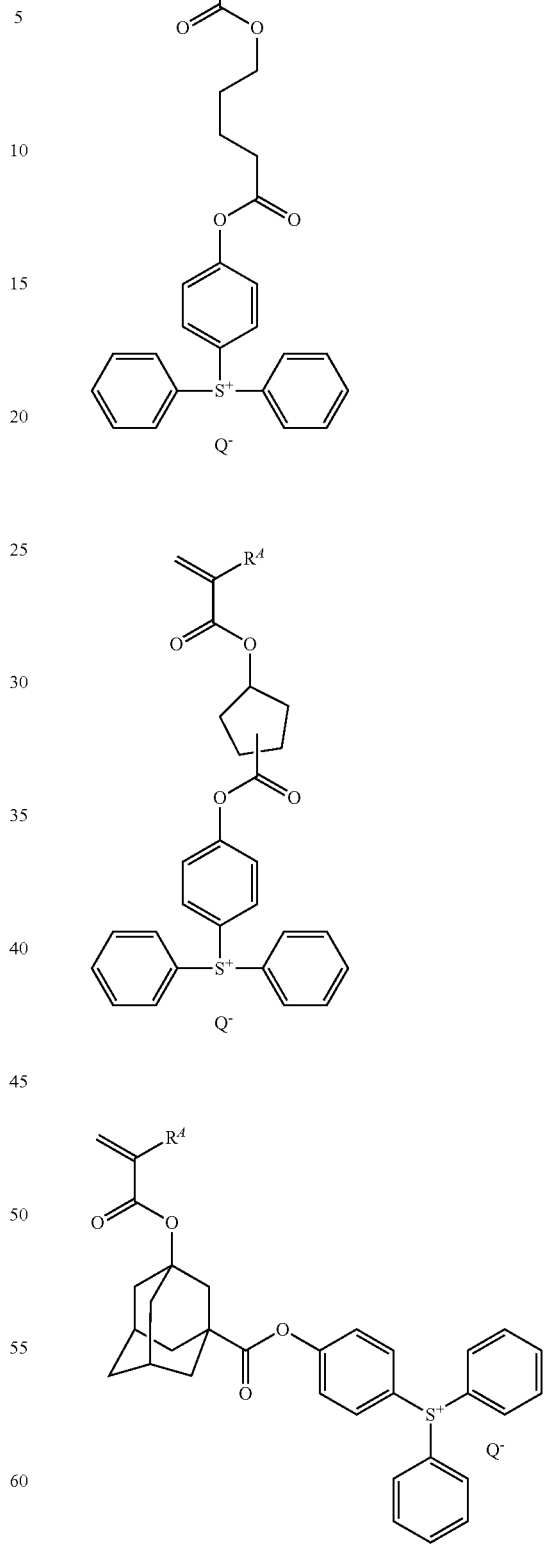
Examples of the monomer from which recurring units (b2) are derived are shown below, but not limited thereto. $R^A$ is as defined above.

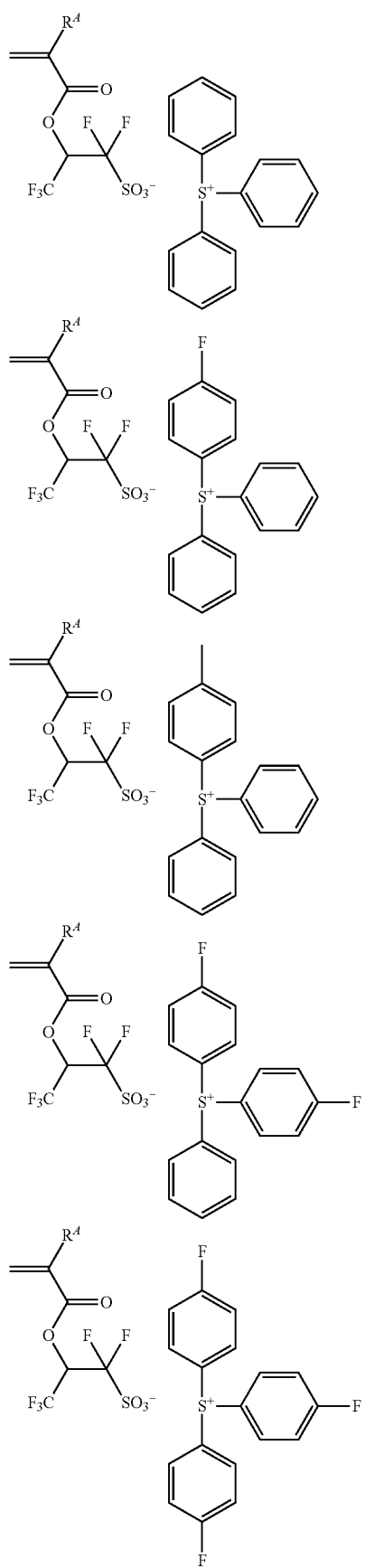
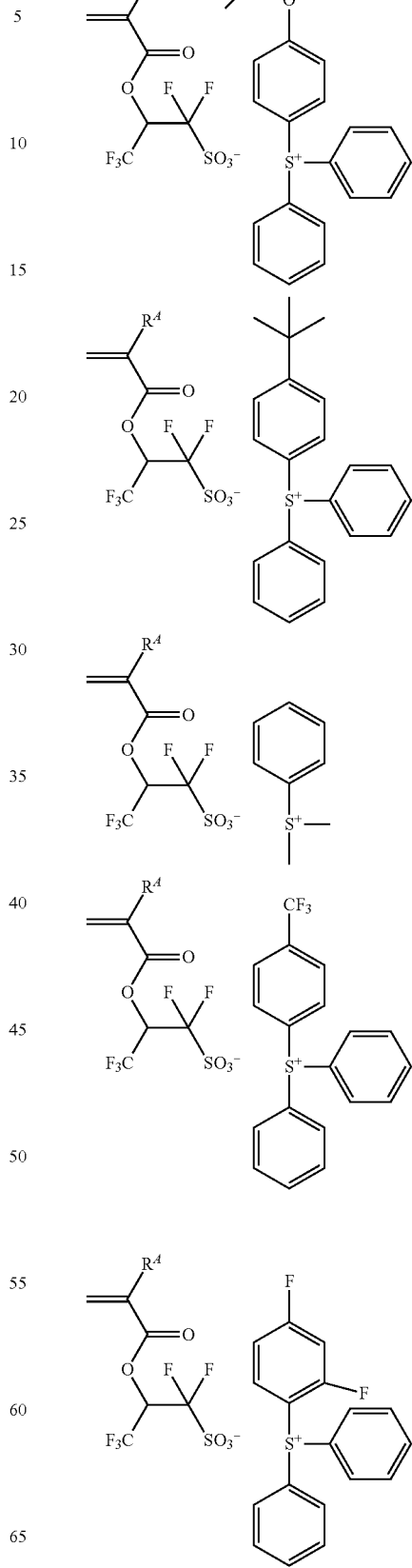

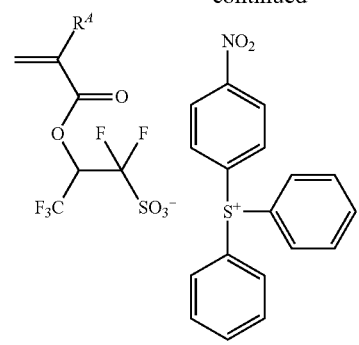
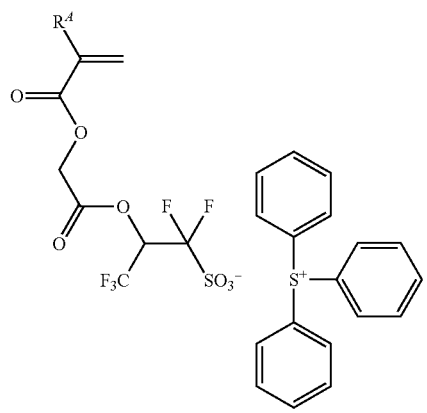
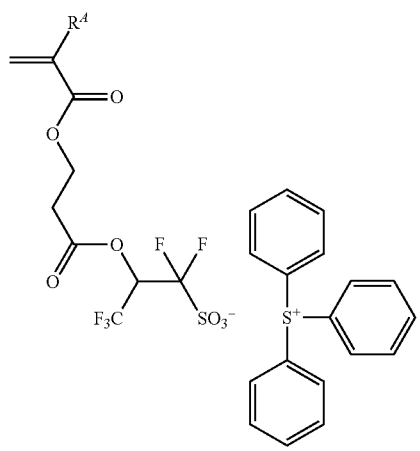
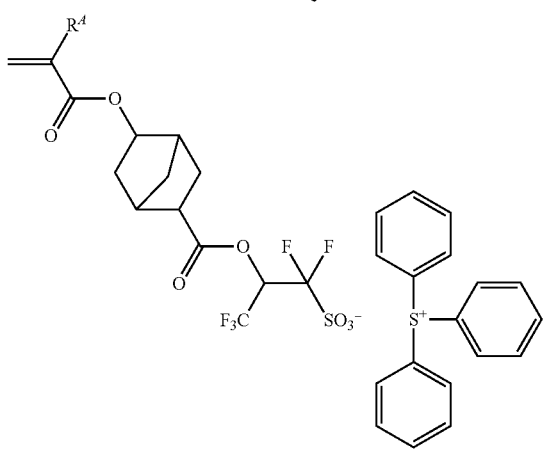
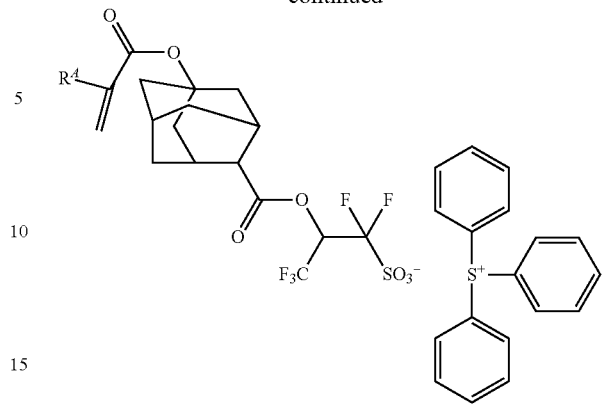
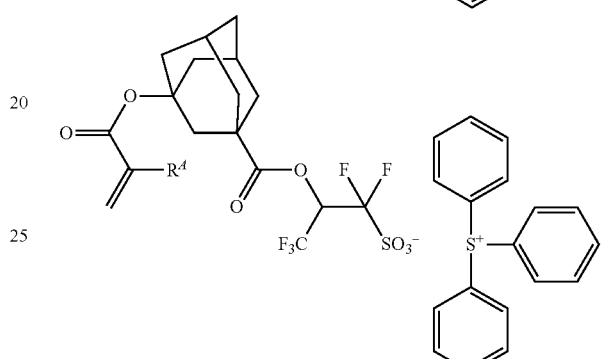
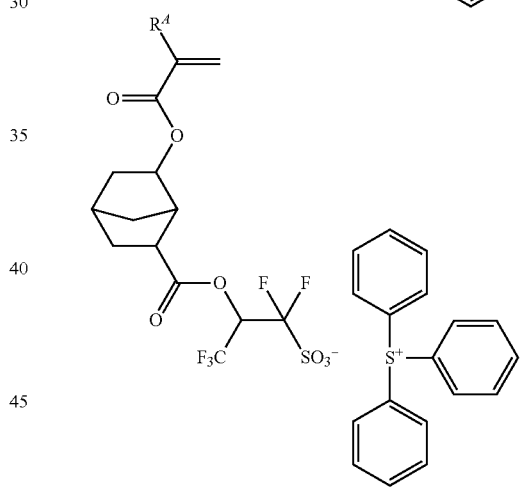
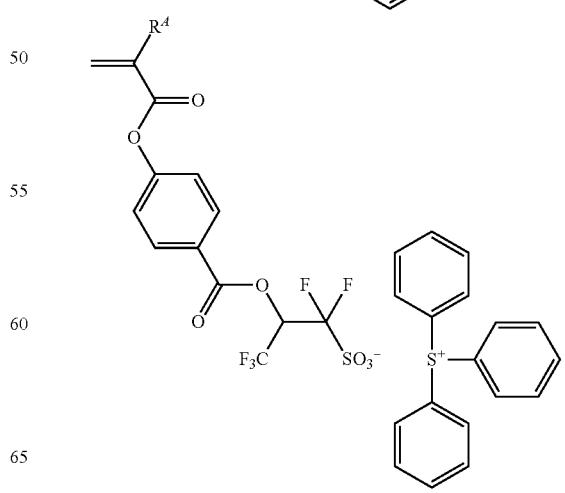

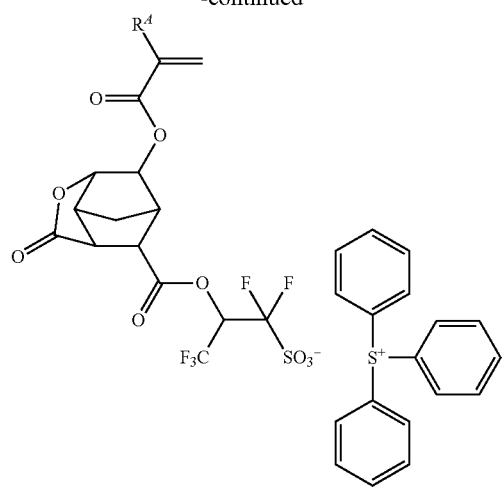
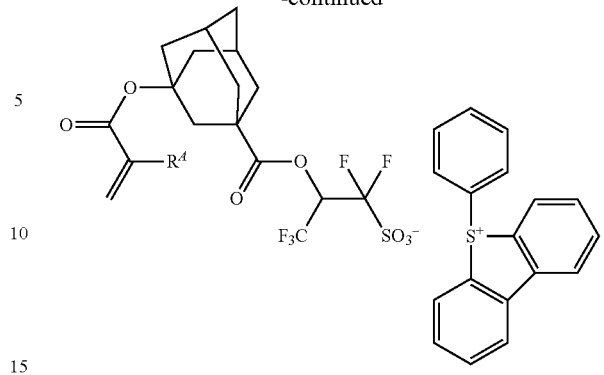
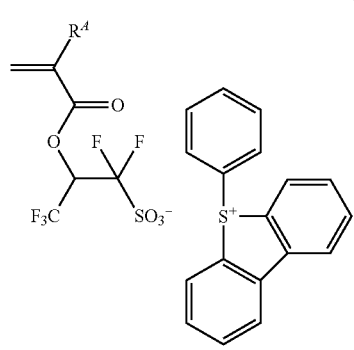
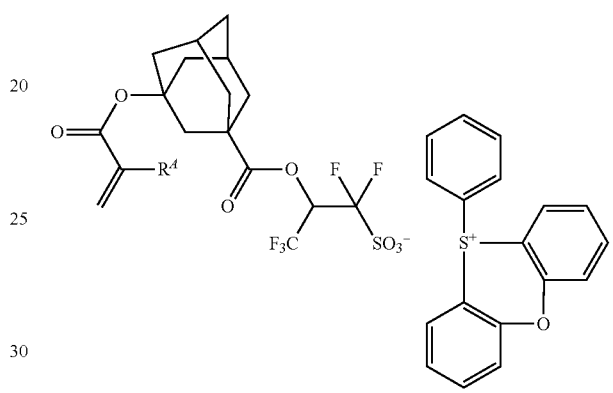
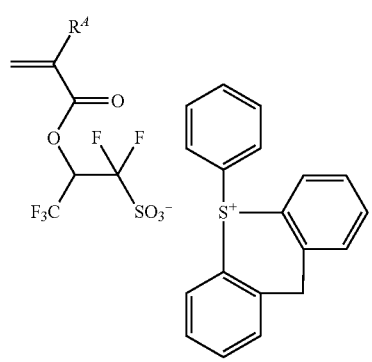
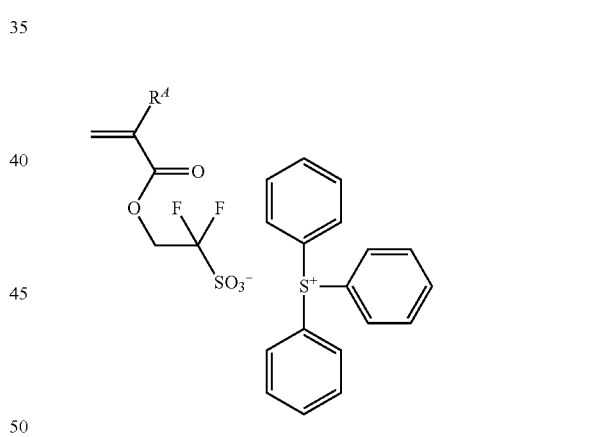
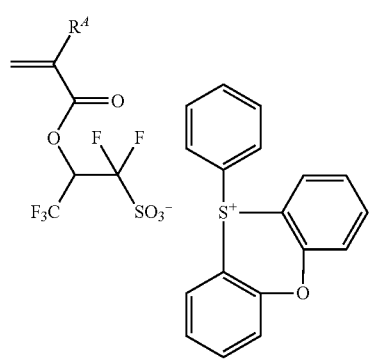
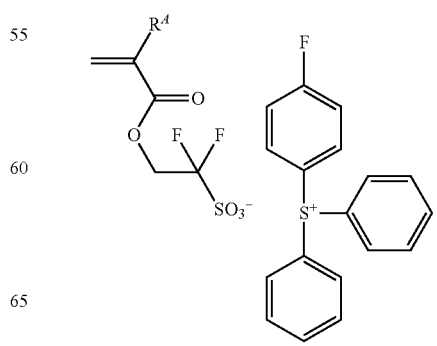

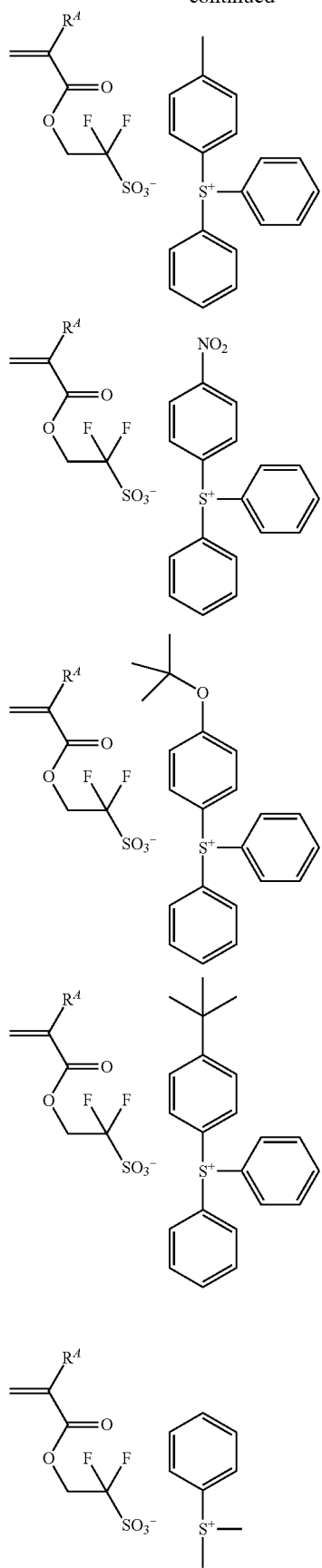

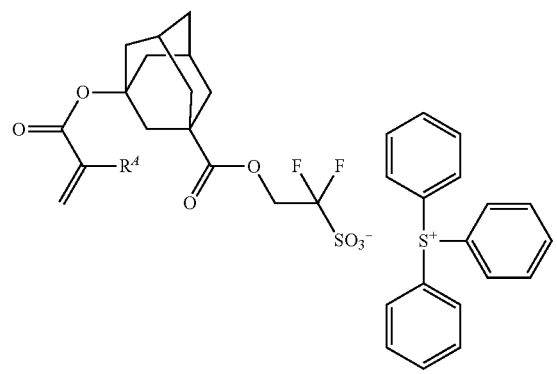
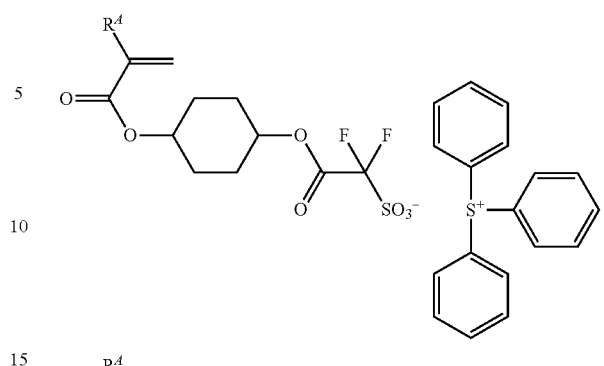
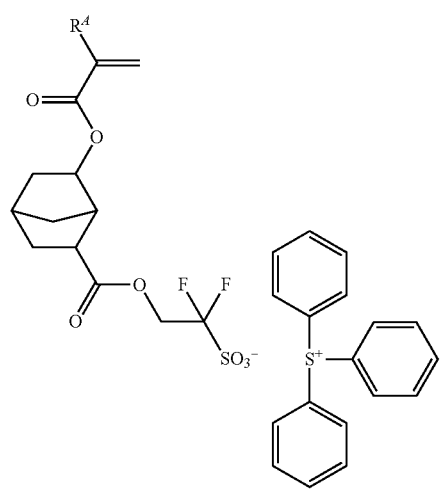
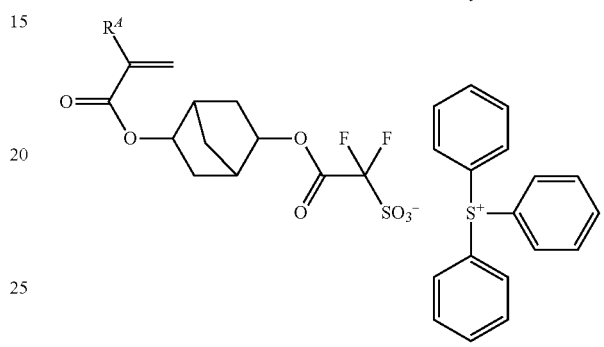
Examples of the monomer from which recurring units (b3) are derived are shown below, but not limited thereto. $R^A$ is as defined above.
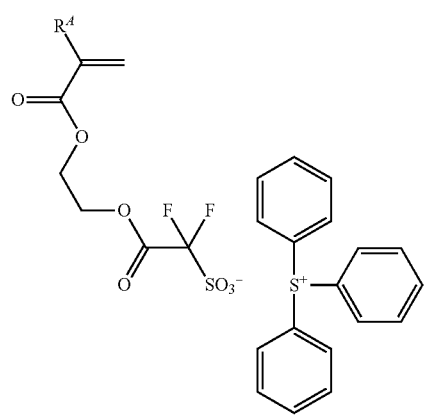
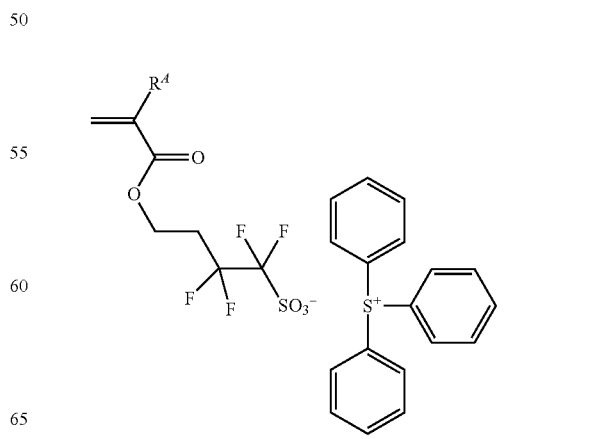

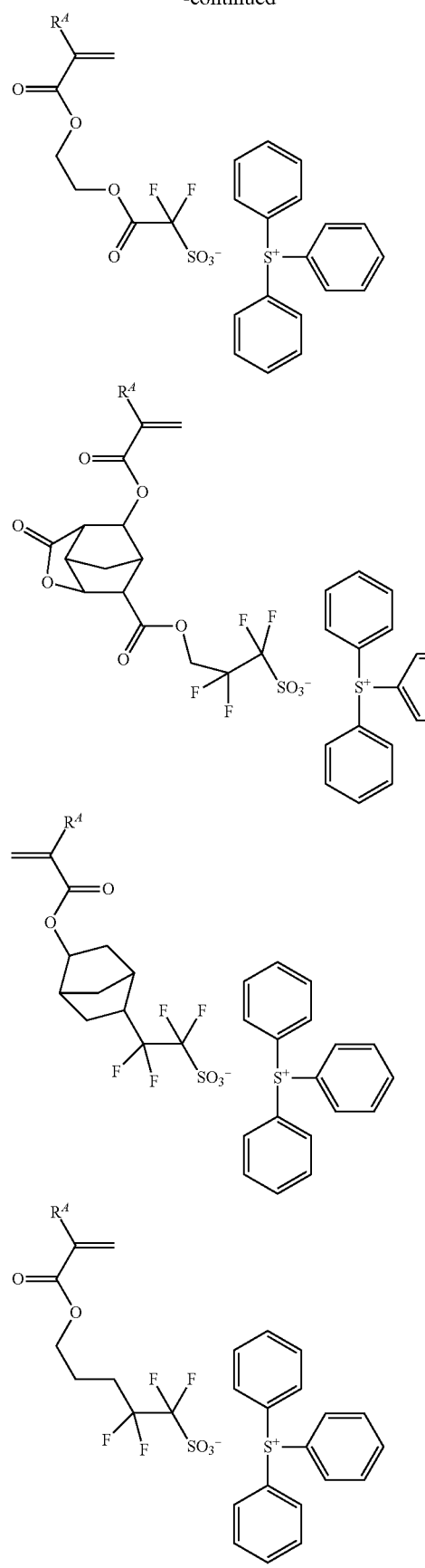
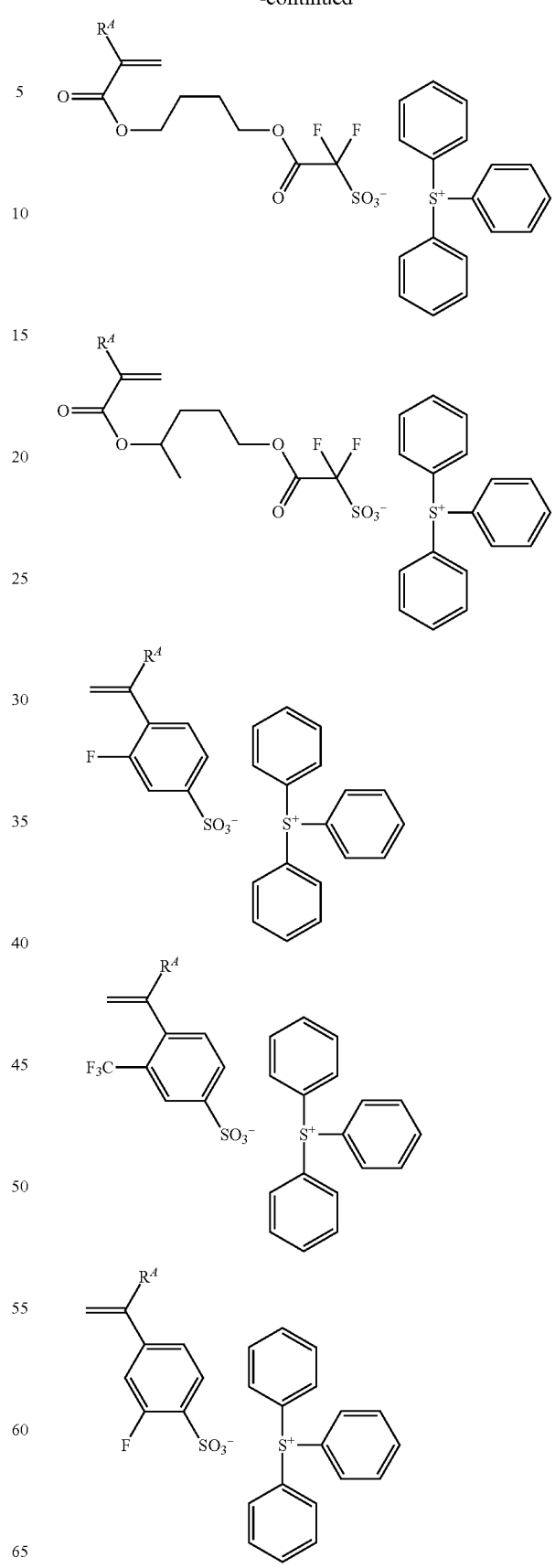

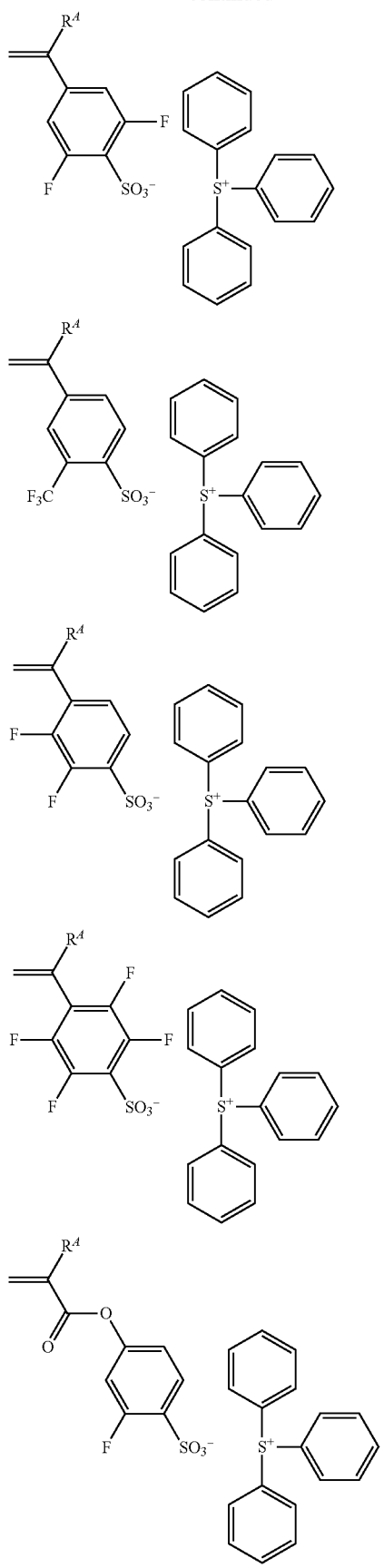
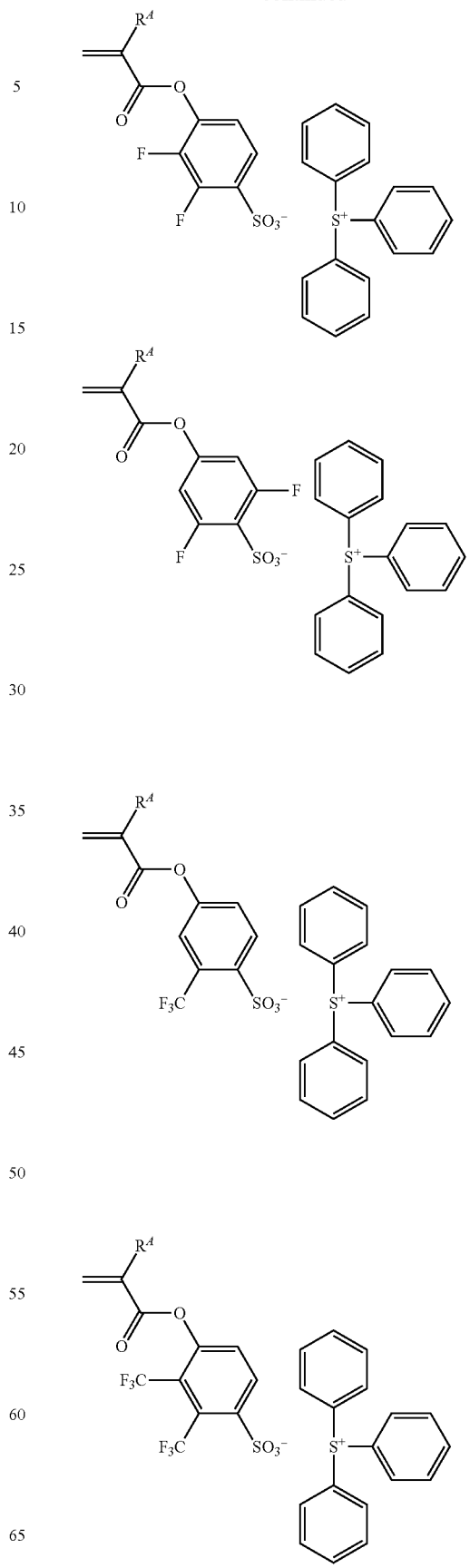

101
-continued
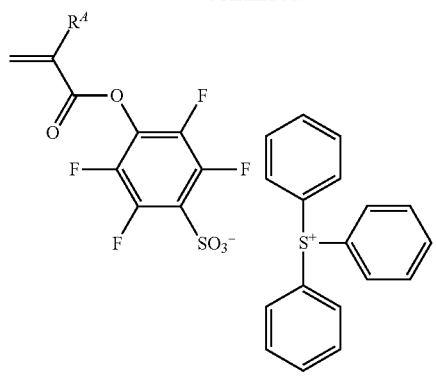
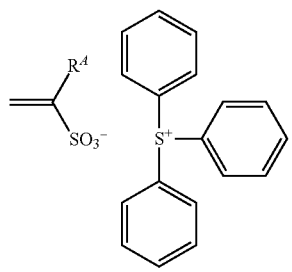
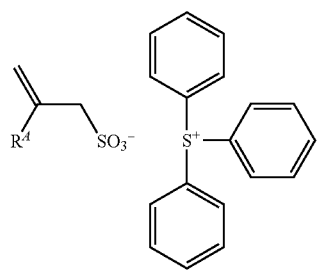
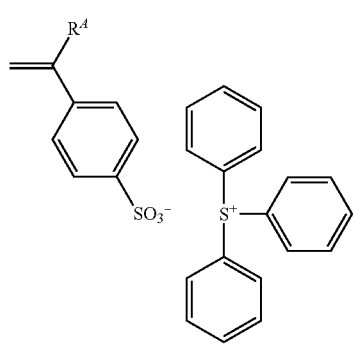
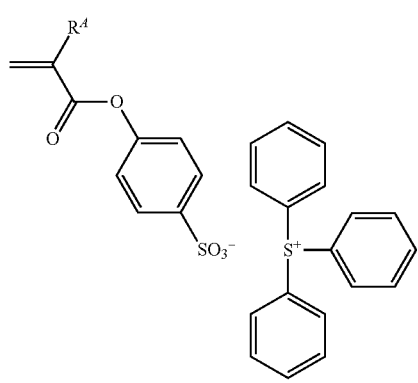
102
-continued
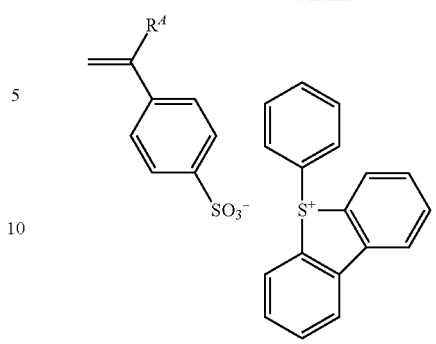
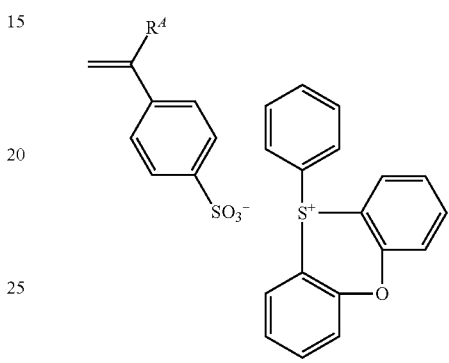
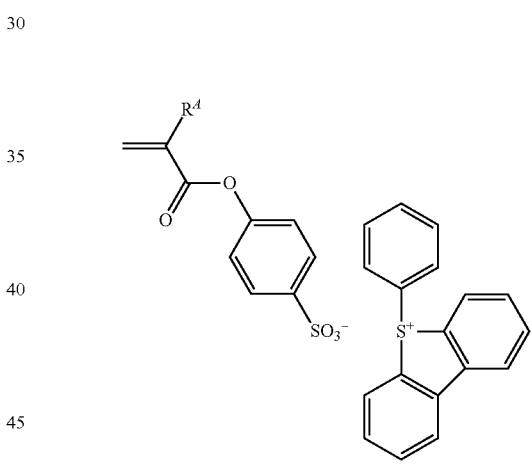
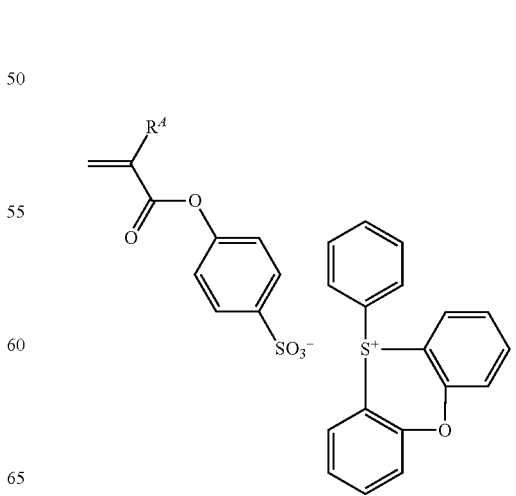

-continued
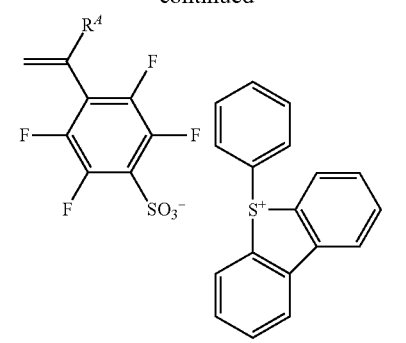
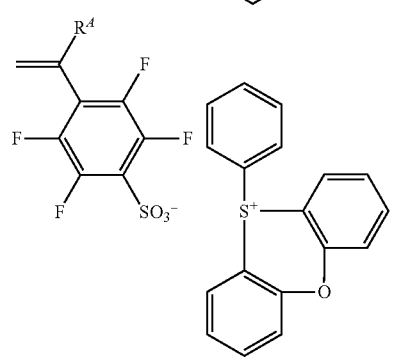
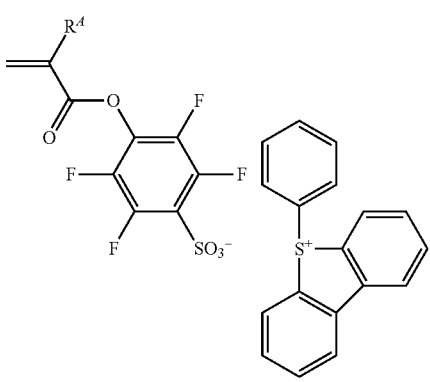
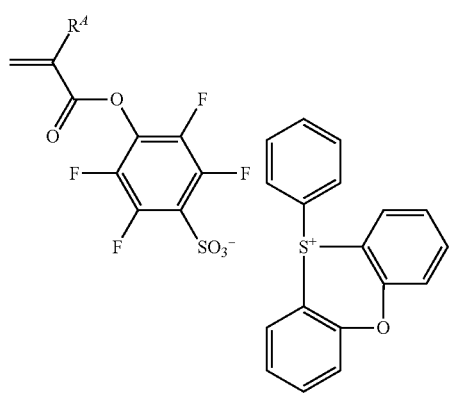
-continued
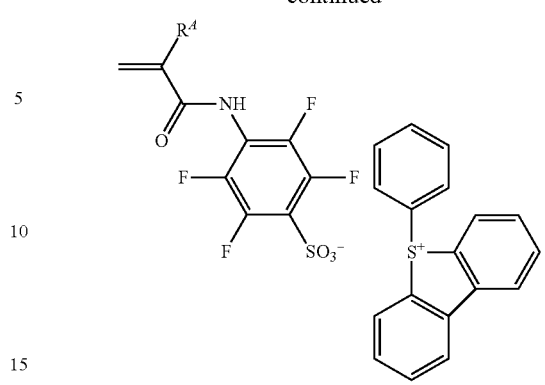
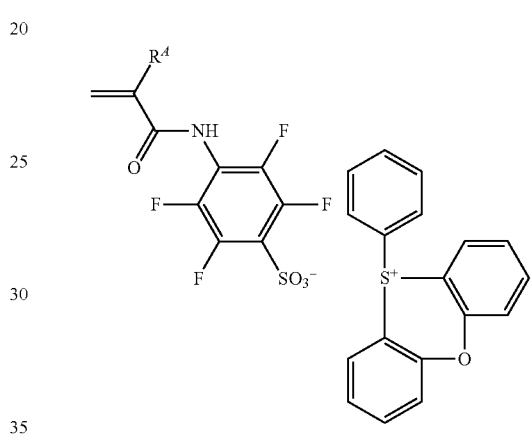
Of the recurring units (b1), (b2) and (b3), units (b2) are most preferred.
In the base resin, recurring units (c) having a phenolic hydroxyl group as the adhesive group may be further incorporated.
Examples of the monomer from which recurring units (c) are derived are shown below, but not limited thereto. $R^A$ is as defined above.
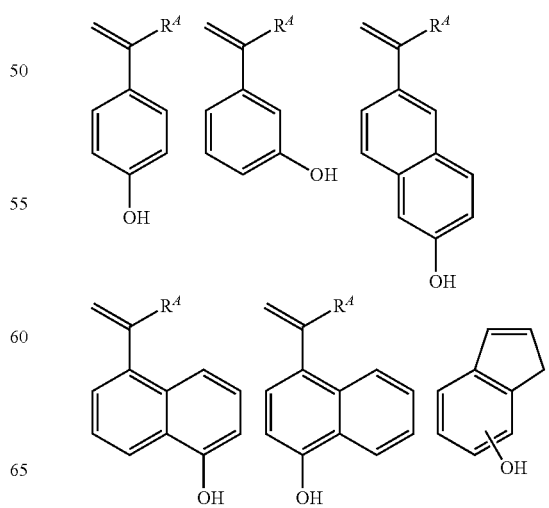

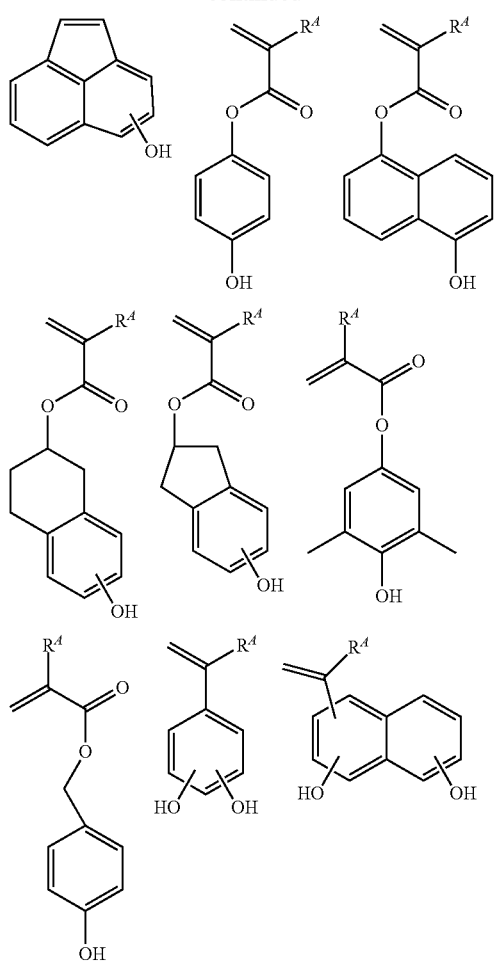
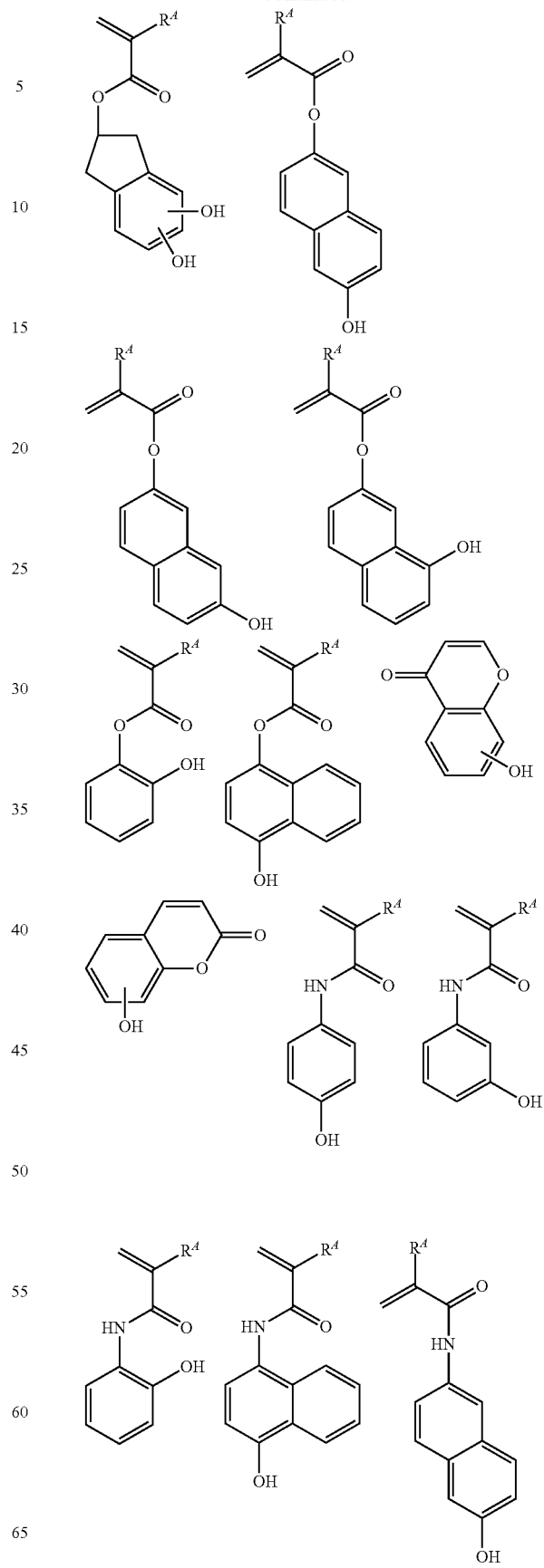

107
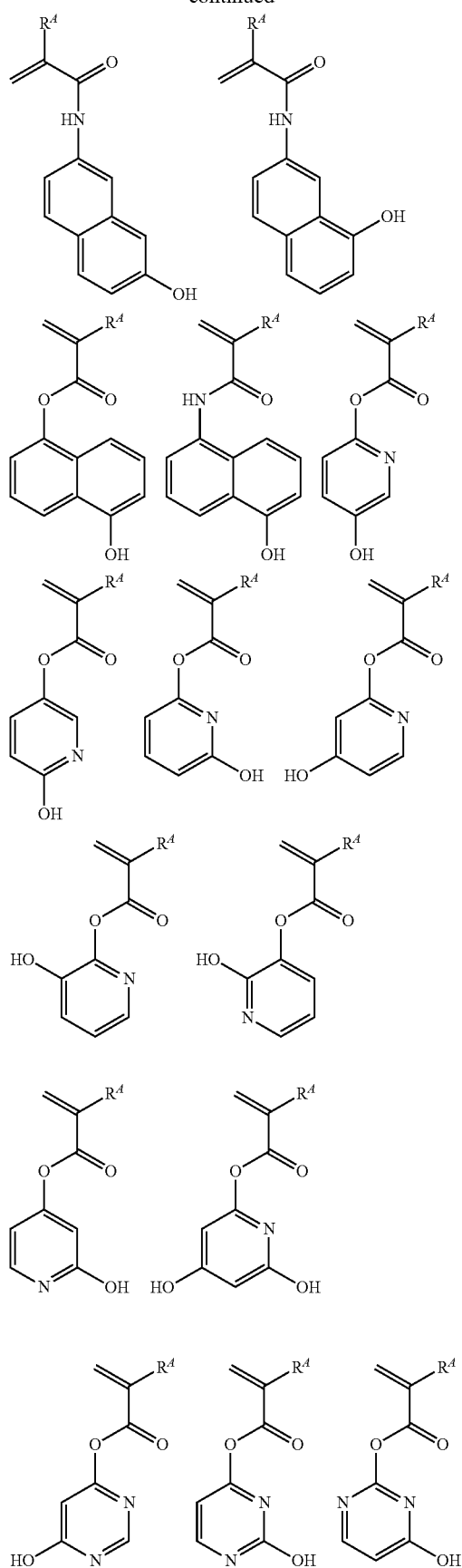
-continued
108
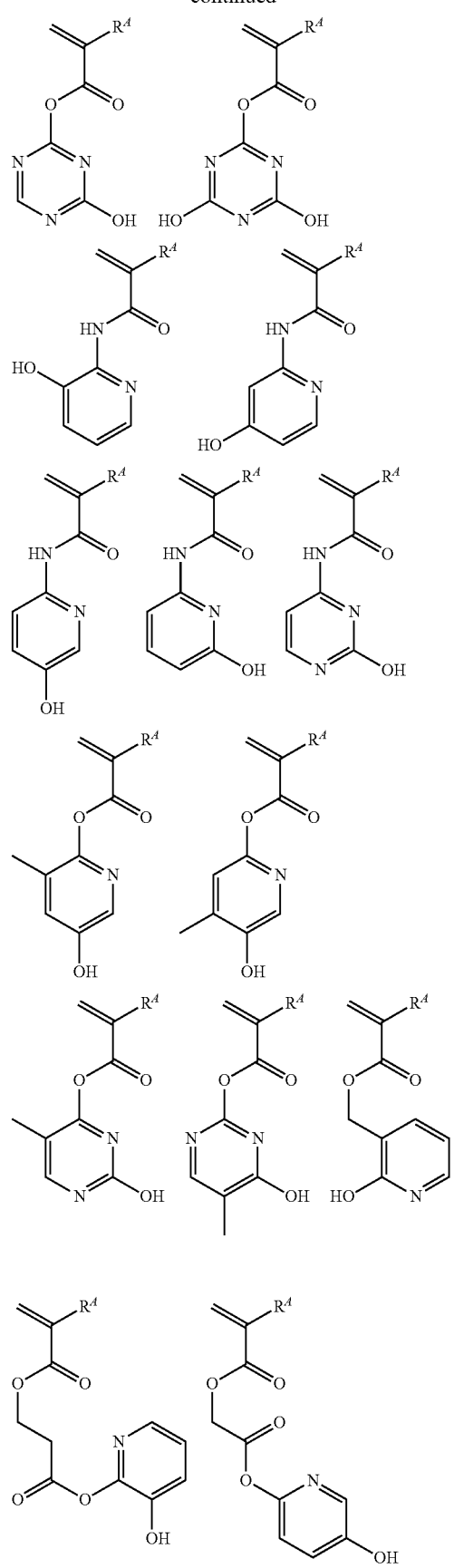
-continued

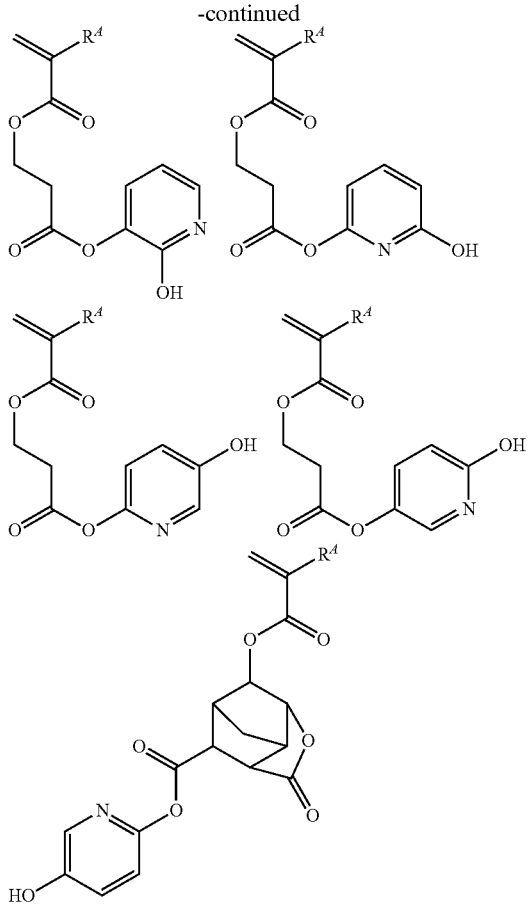
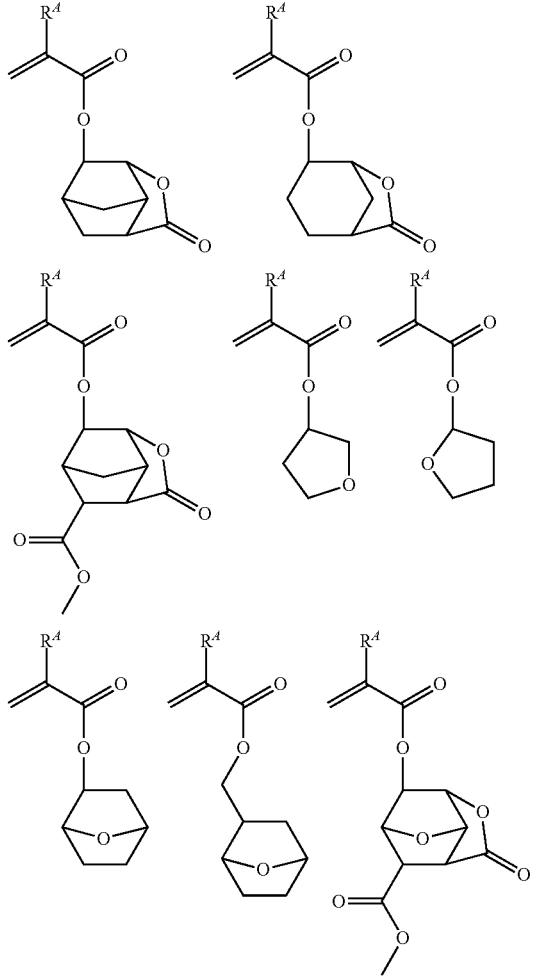

Recurring units (d) having another adhesive group may also be incorporated in the base resin. Examples of the other adhesive group include hydroxyl (other than the phenolic hydroxyl), carboxyl, lactone ring, carbonate, thiocarbonate, carbonyl, cyclic acetal, ether bond, ester bond, sulfonic acid ester bond, cyano, amide, —O—C(=O)—S—, and —O—C(=O)—NH—.

Examples of the monomer from which reclining units (d) are derived are shown below, but not limited thereto. $R^A$ is as defined above.

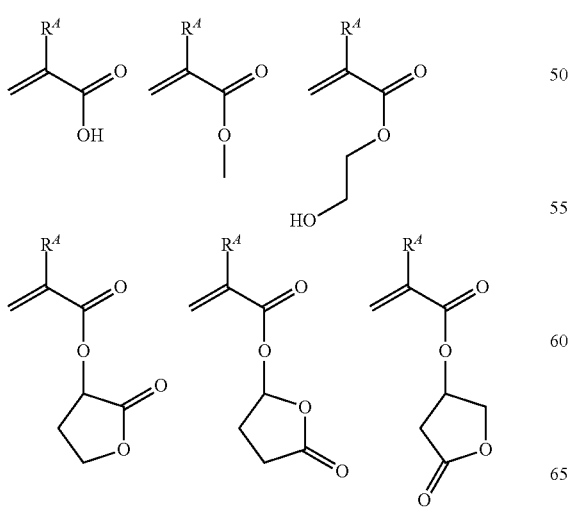
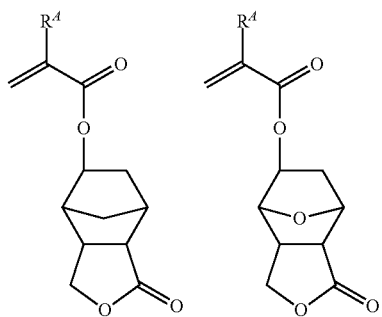

111
-continued
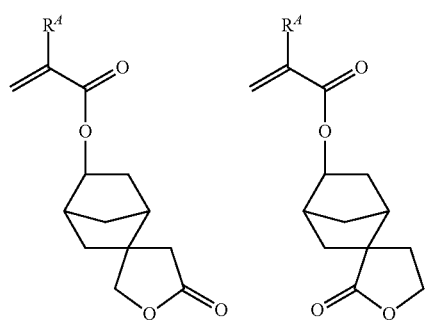
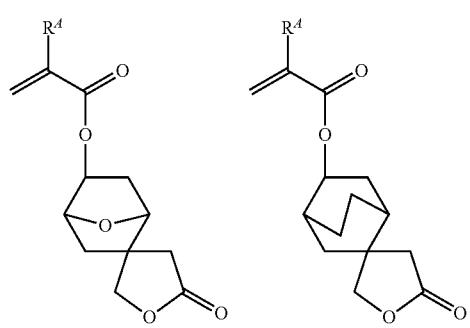
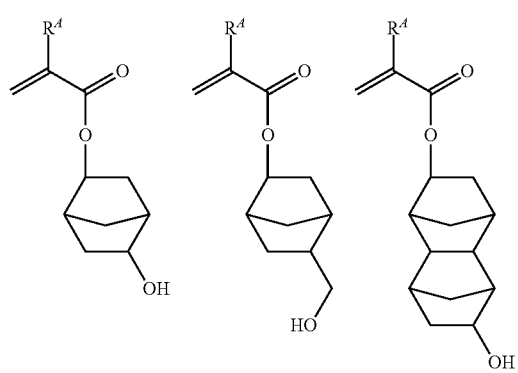
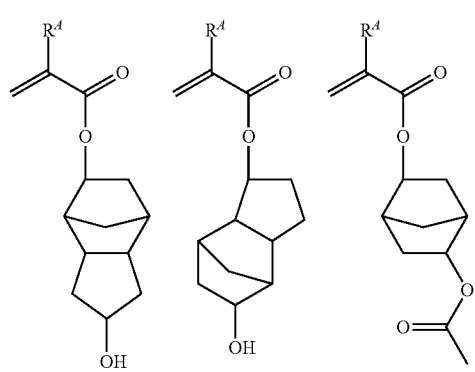
112
-continued
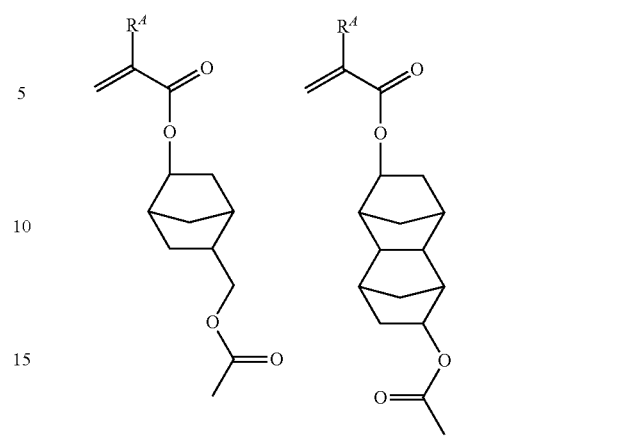
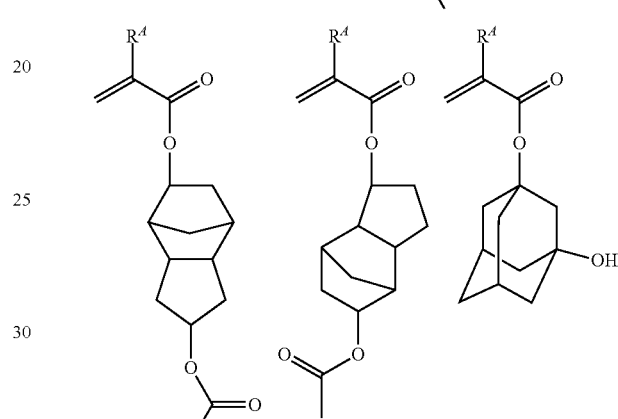
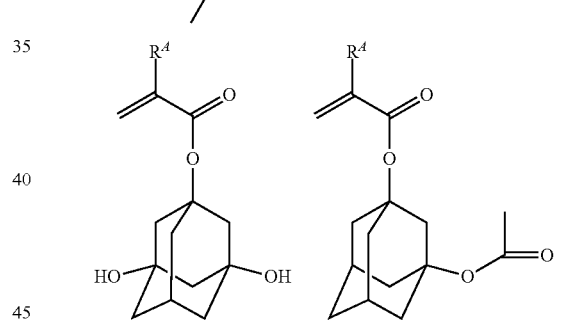
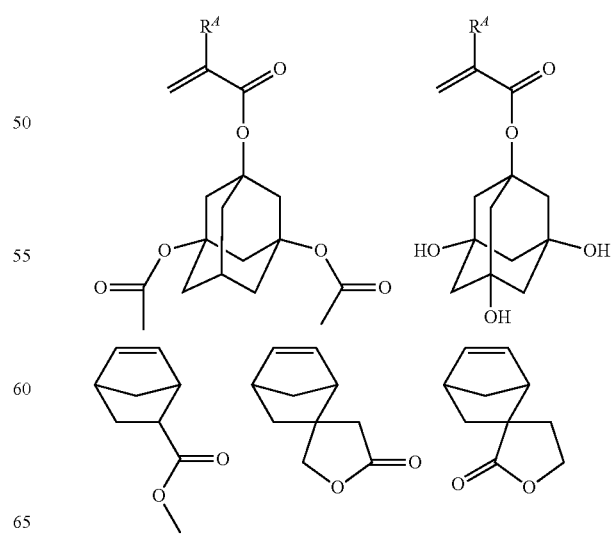

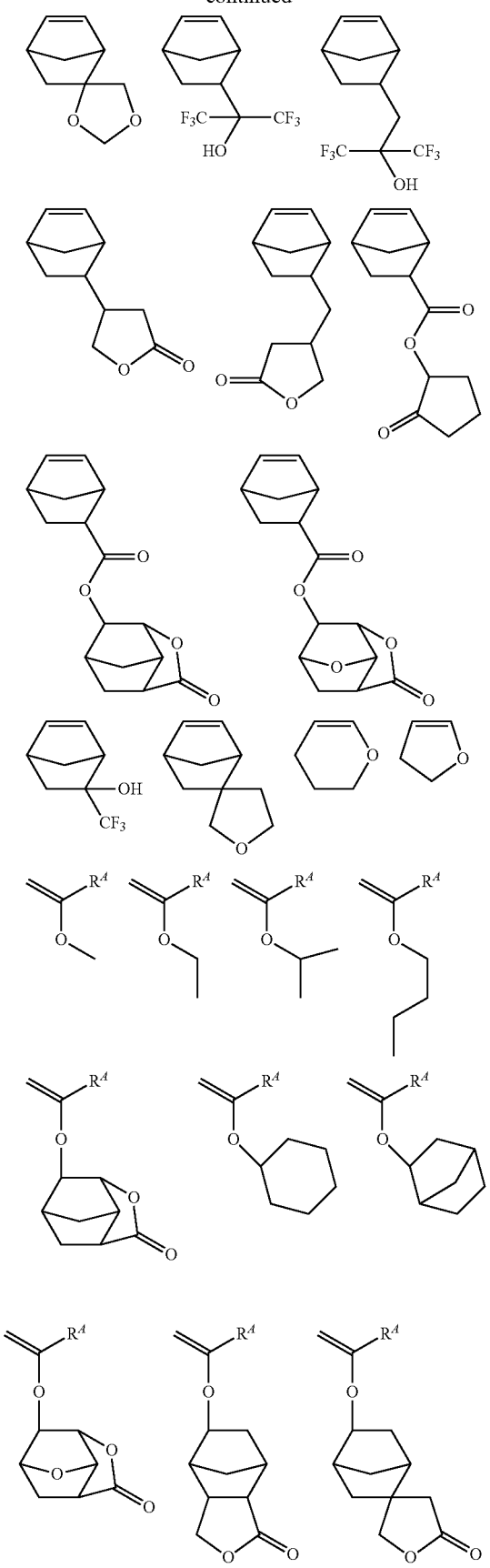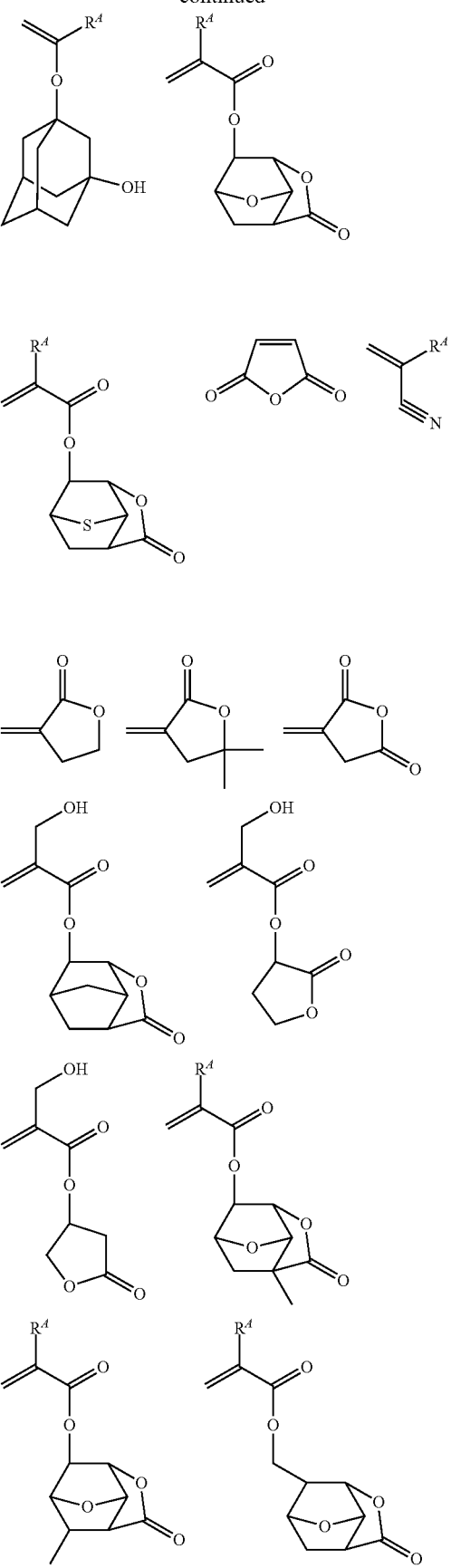

115
-continued
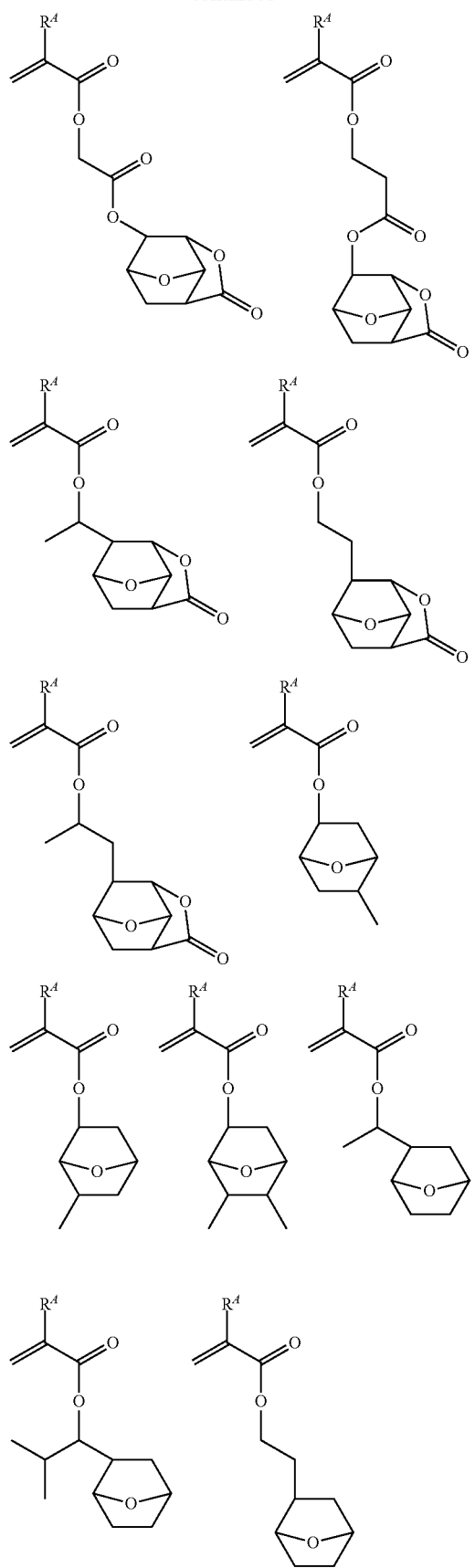
116
-continued
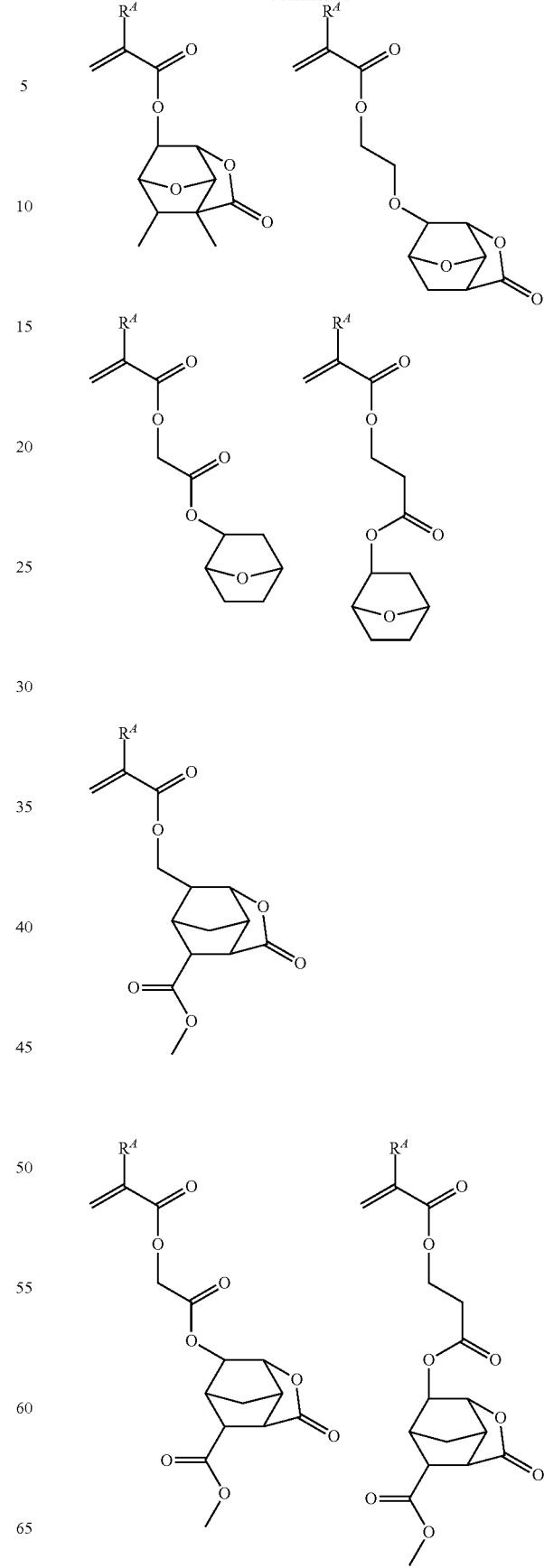

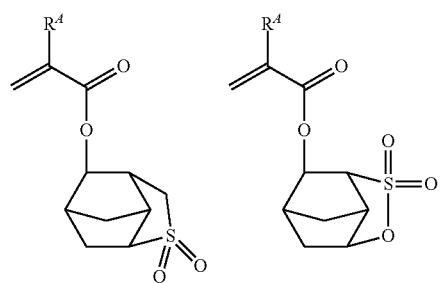
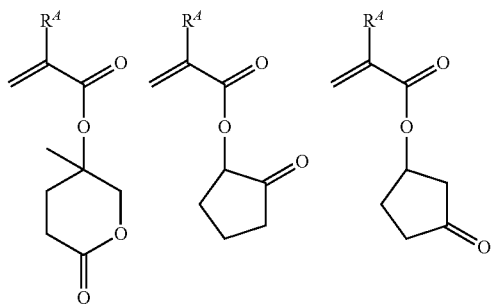
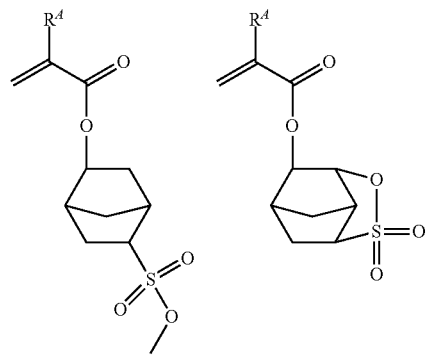
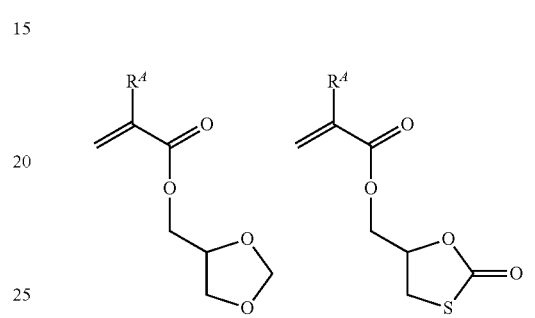
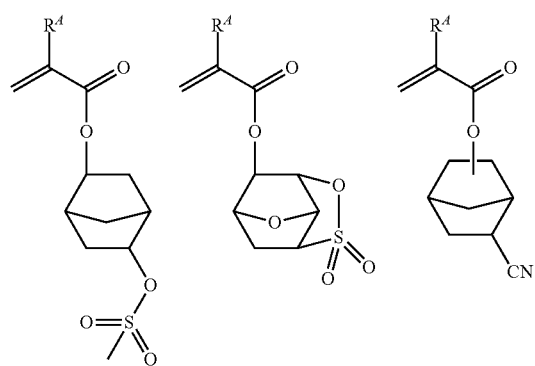
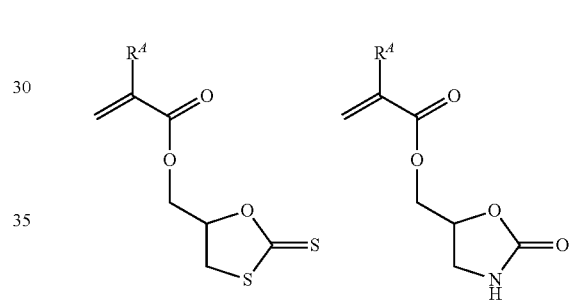
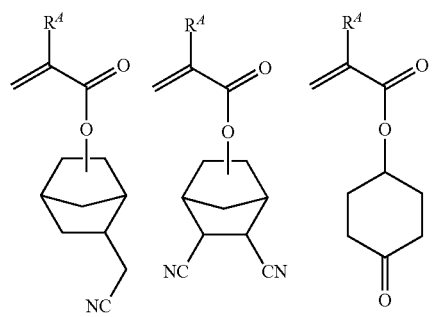
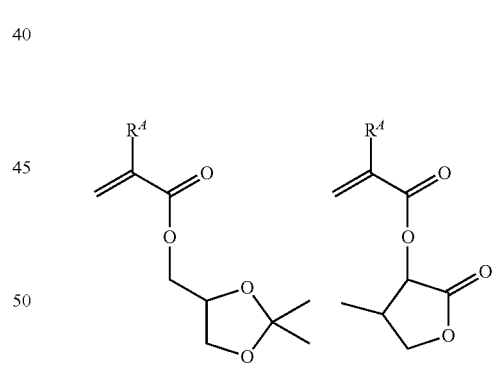
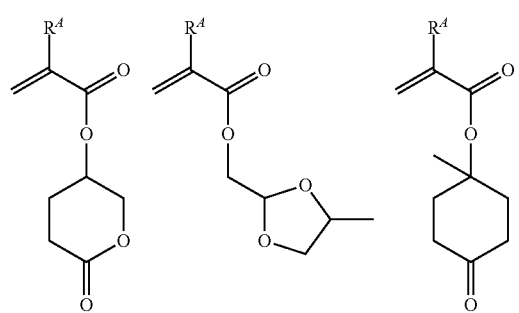
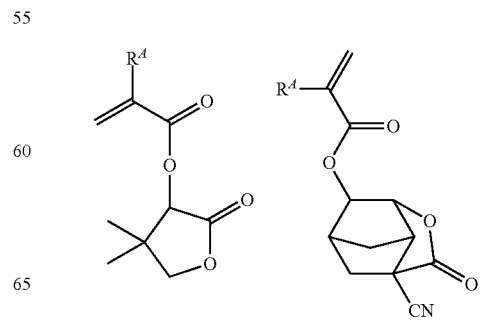

-continued
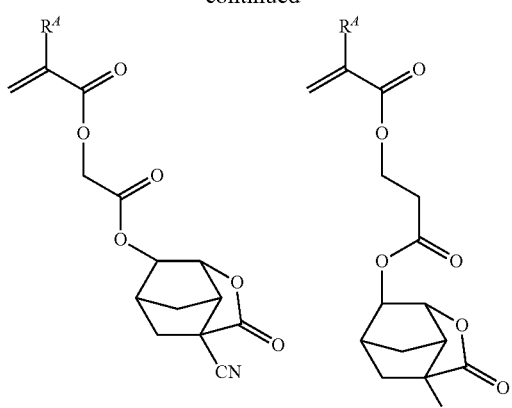
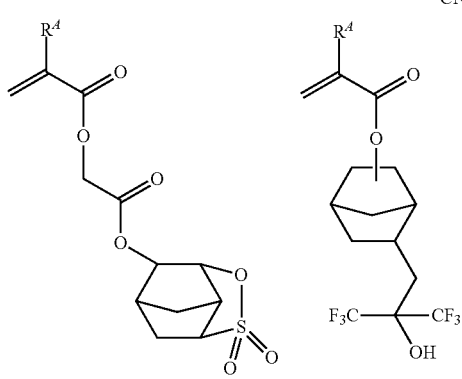
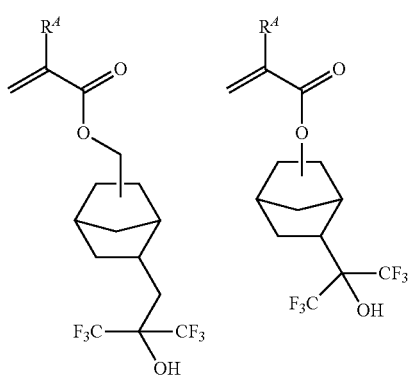
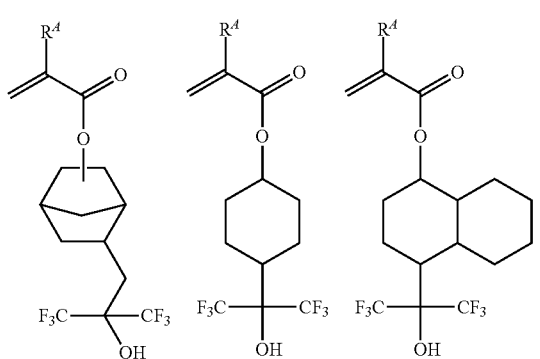
-continued
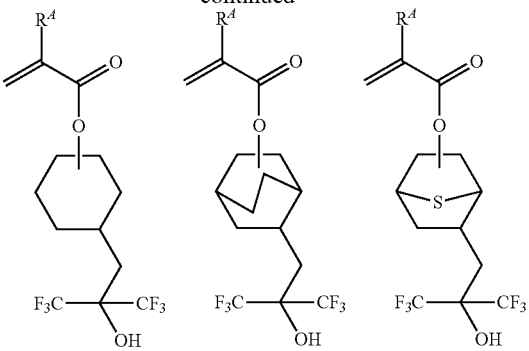
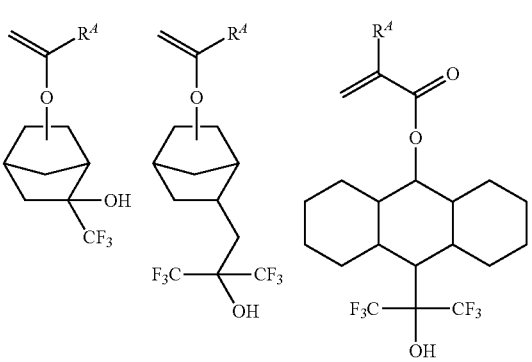
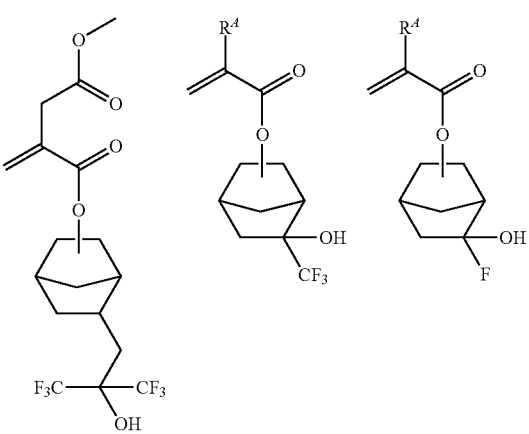
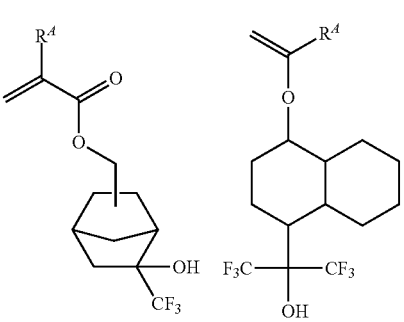

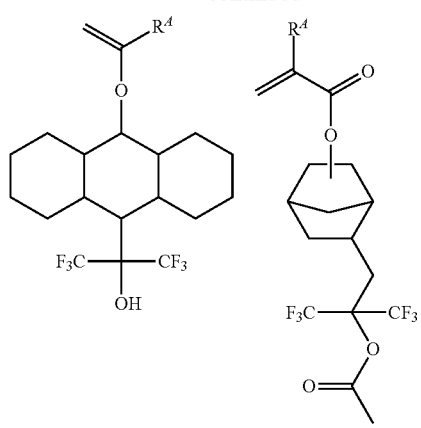
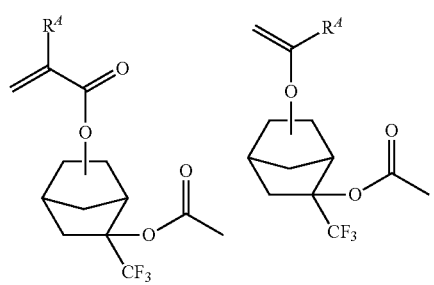
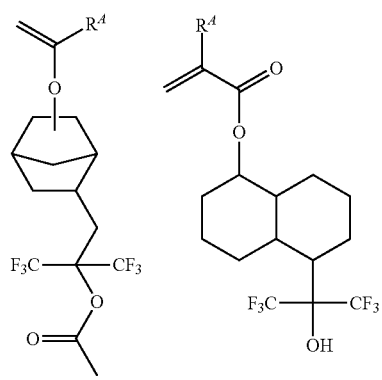
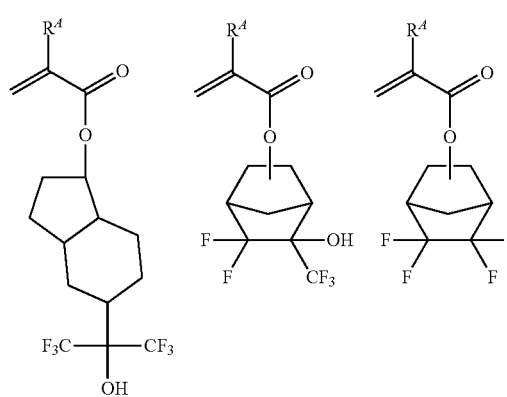
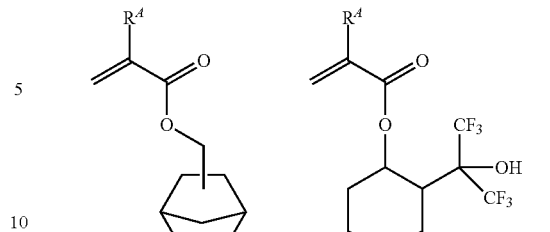
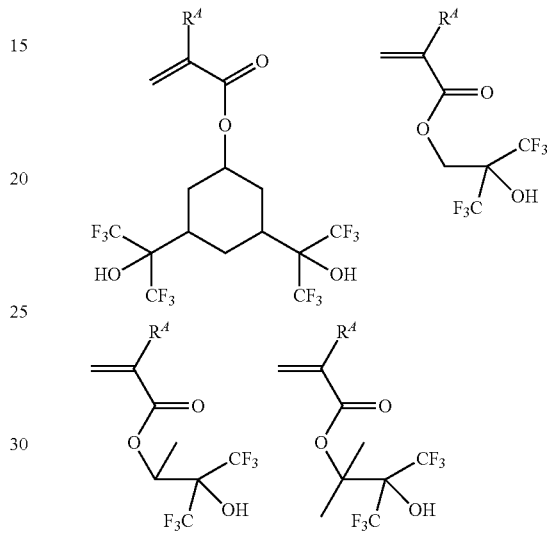
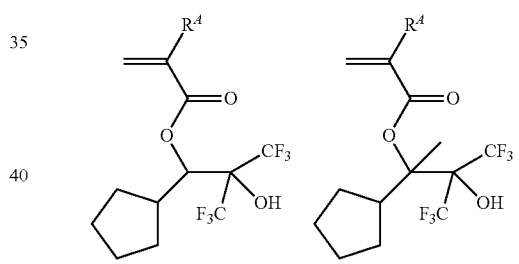
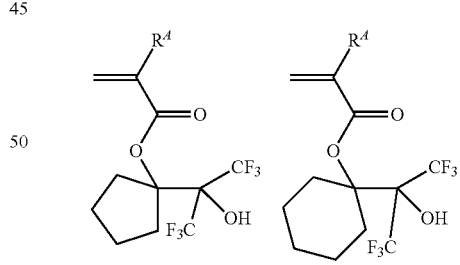
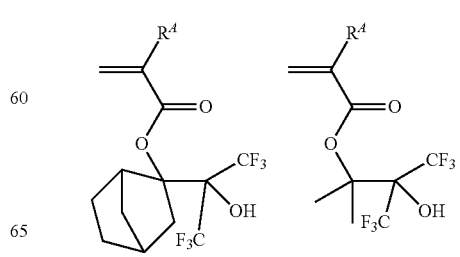

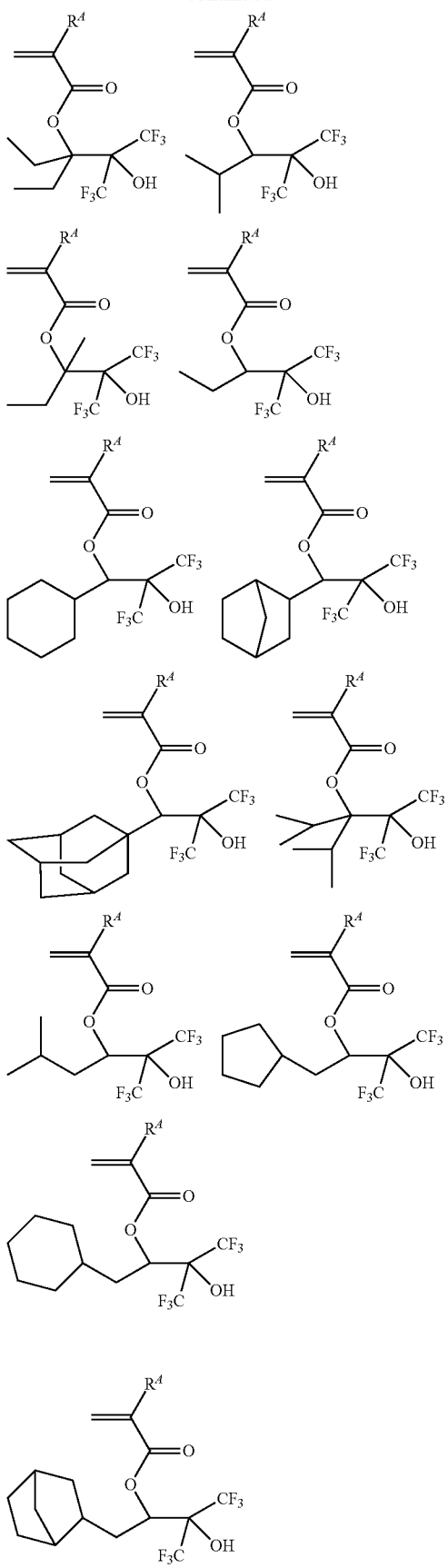
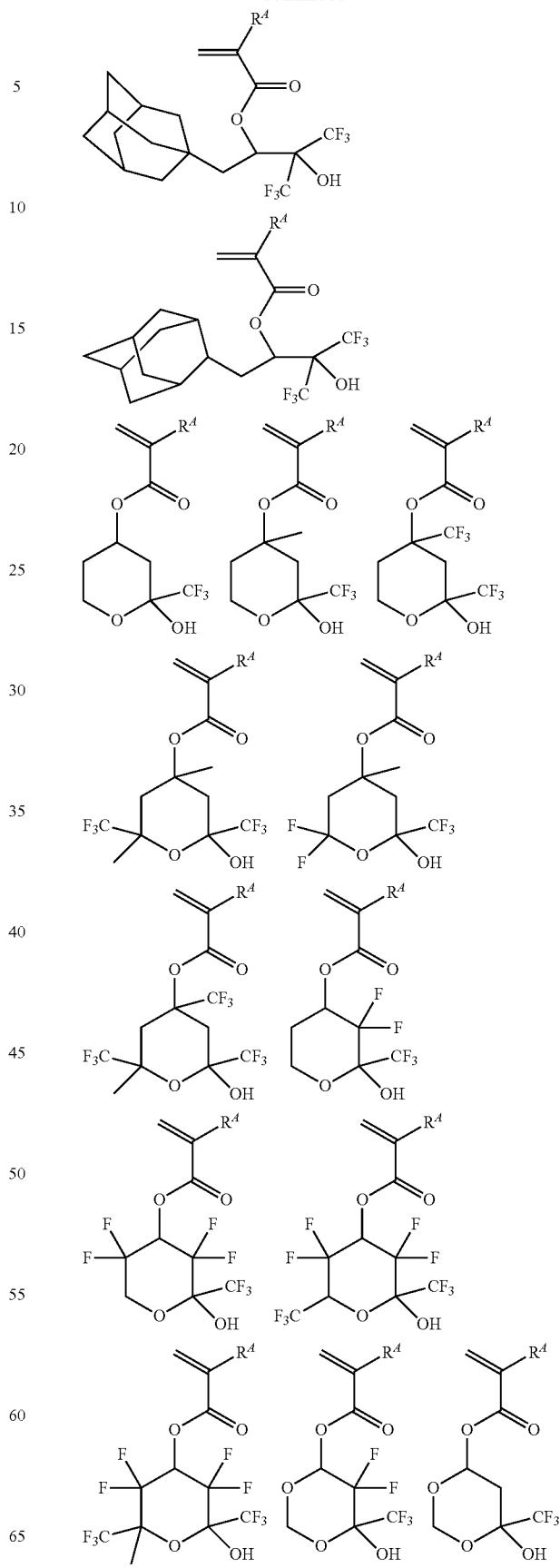

125
-continued
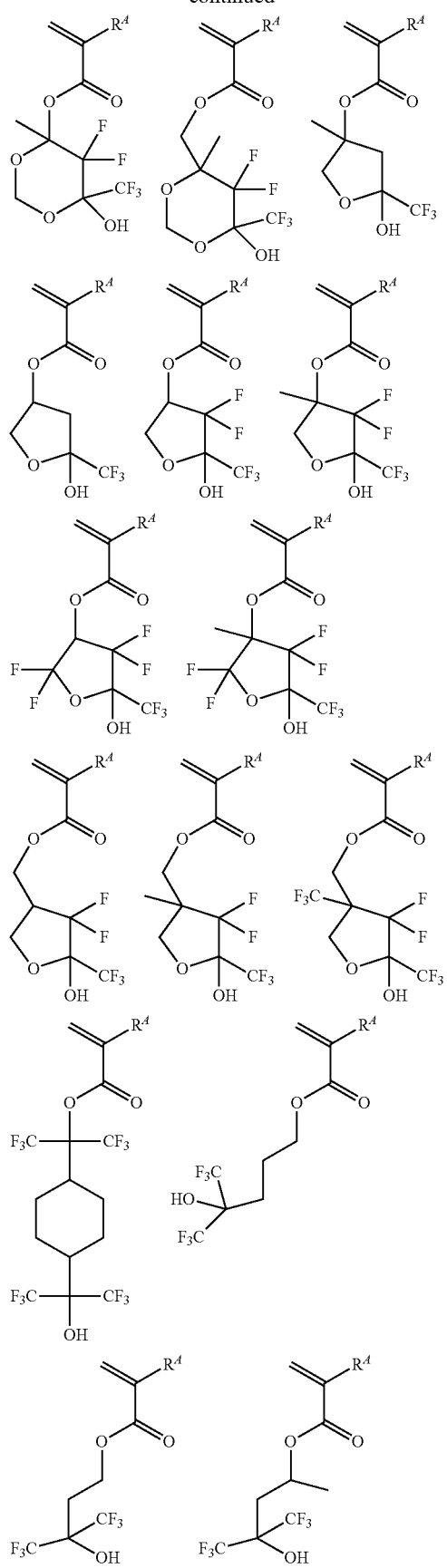
126
-continued
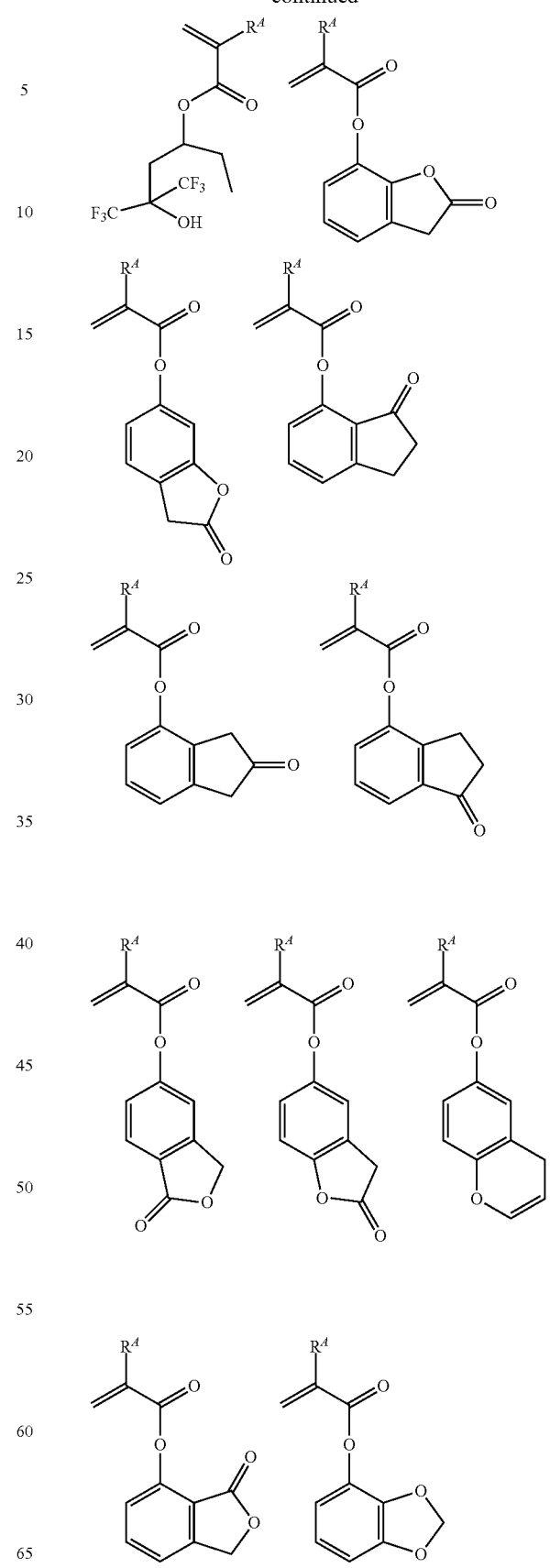

127
-continued
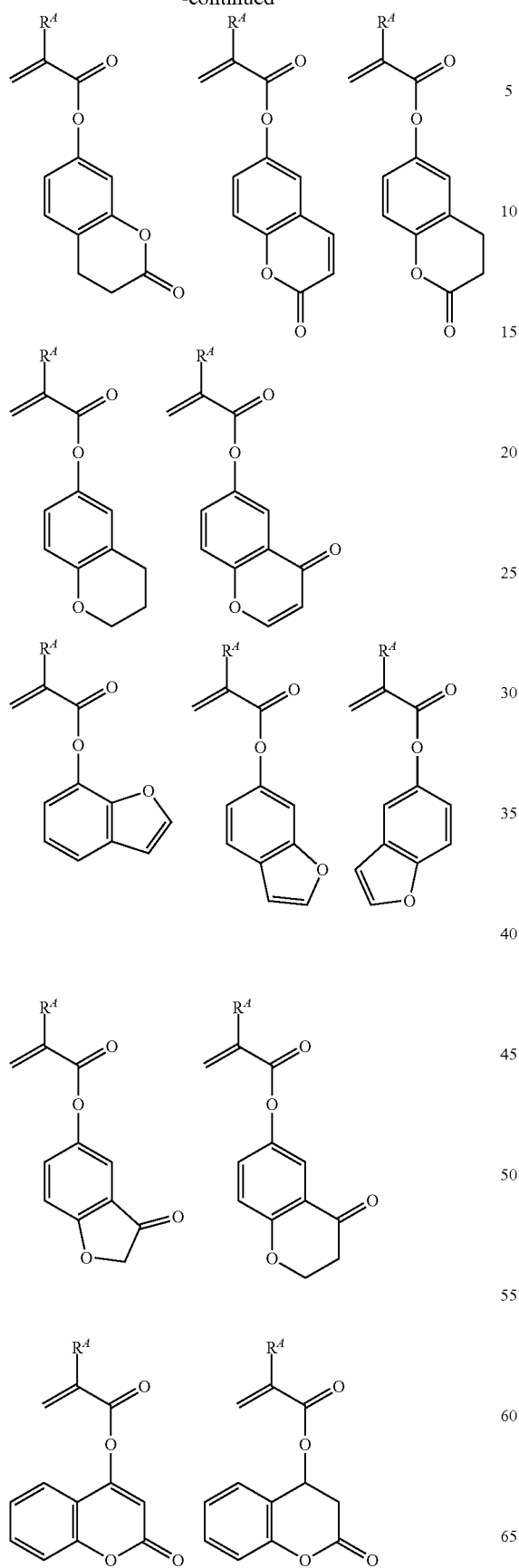
128
-continued
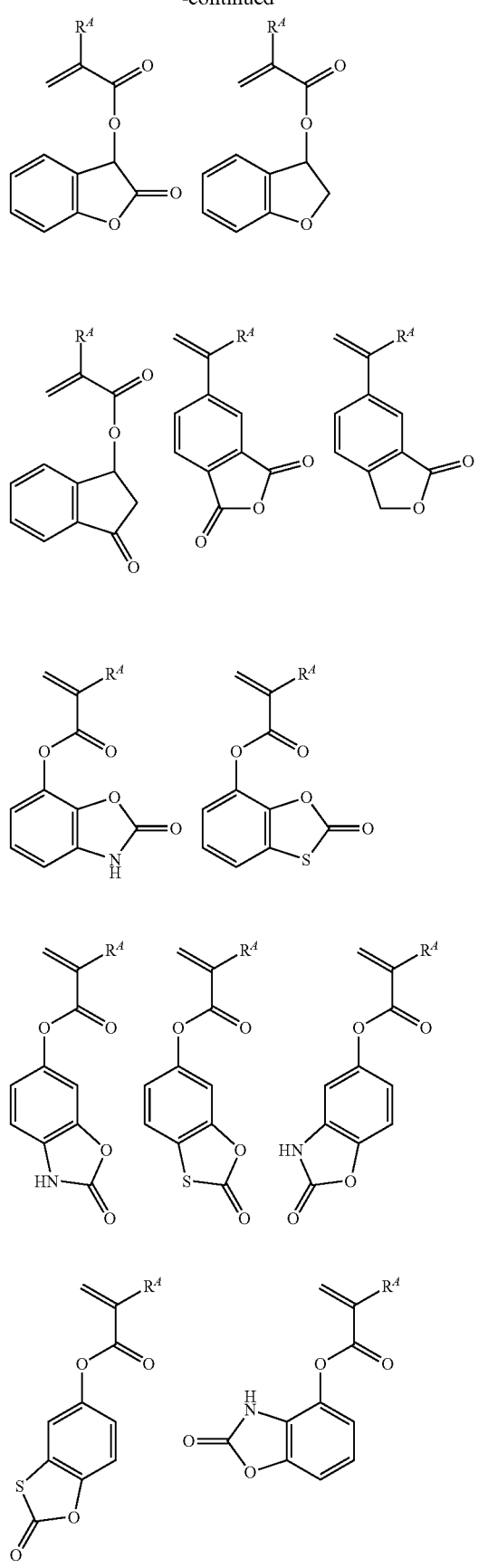

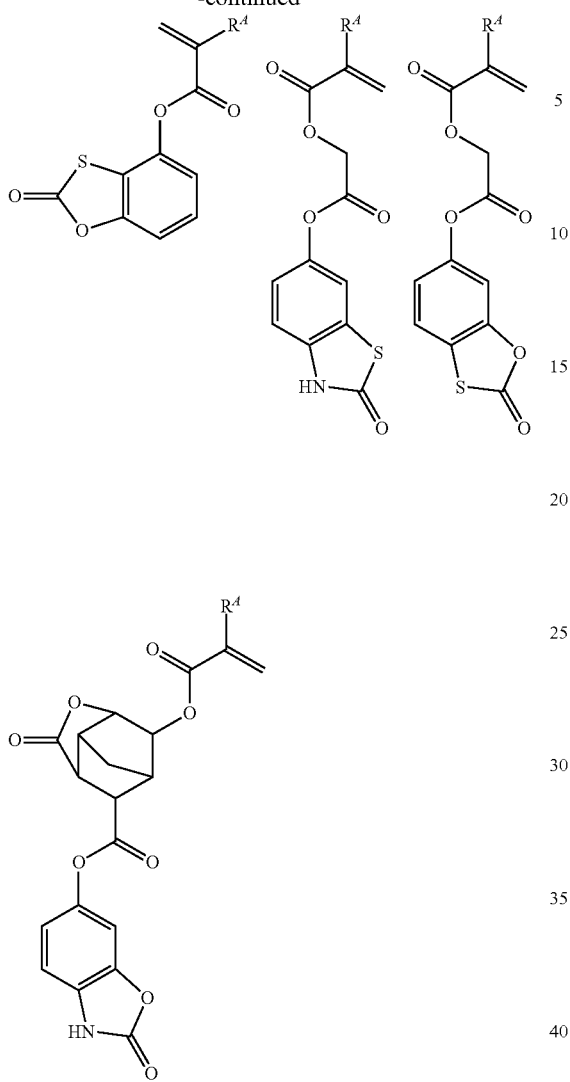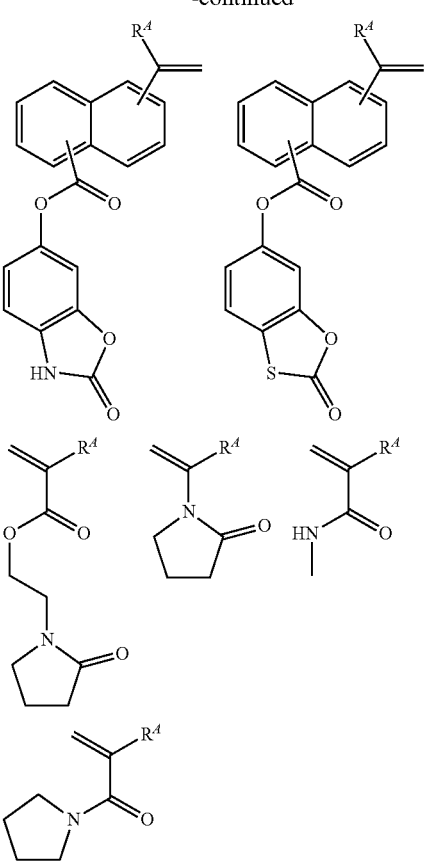
The base resin may further comprise reclining units (e) derived from indene, benzofuran, benzothiophene, acenaphthylene, chromone, coomarin, norbornadiene, and derivatives thereof.
Examples of the monomer from which recurring units (e) are derived are shown below, but not limited thereto.
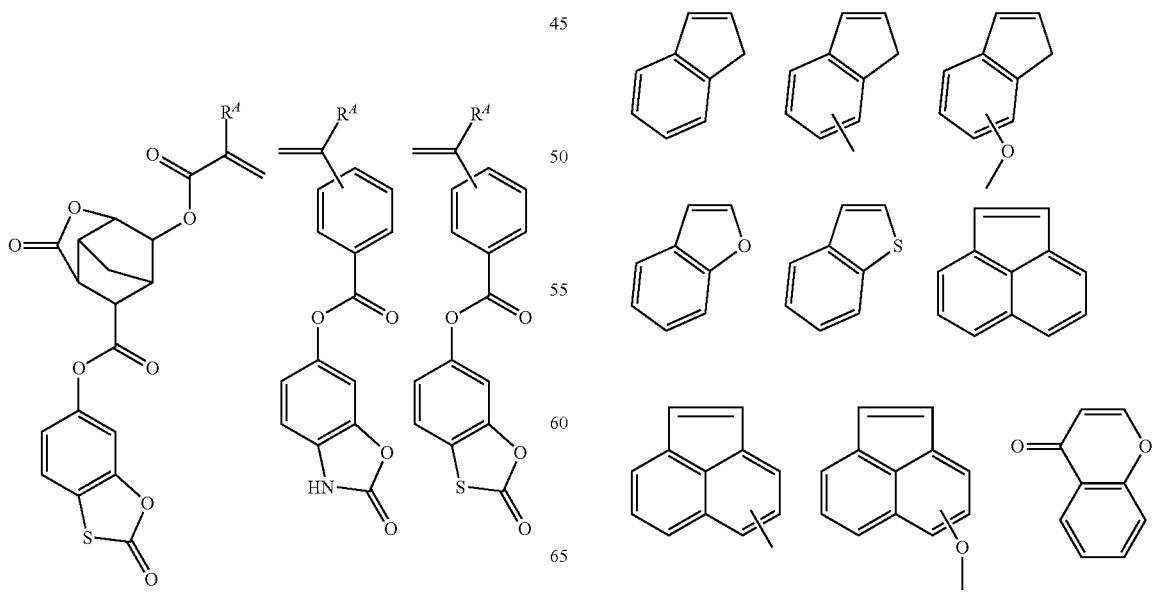

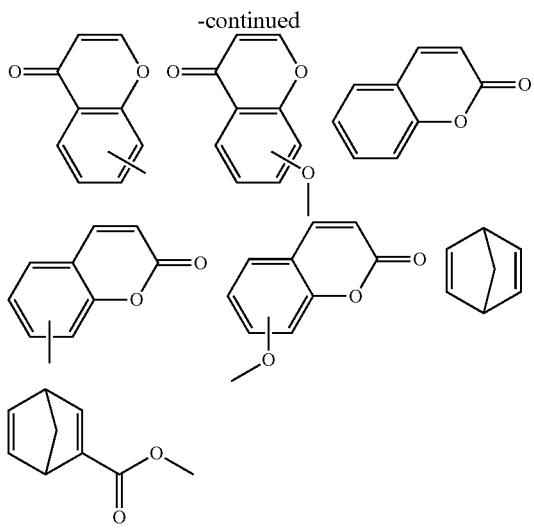

The base resin may further comprise recurring units (f) derived from styrene, vinylnaphthalene, vinylanthracene, vinylpyrene, mertyleneindane, and derivatives thereof.

In a base resin having recurring units (a1), (a2), (b1), (b2), (b3), (c), (d), (e) and (f) copolymerized therein, the fraction of each unit may preferably fall in the range: 0≤a1≤1.0, 0≤a2≤1.0, 0<a1+a2≤1.0, 0≤b1≤0.5, 0≤b2≤0.5, 0≤b3≤0.5, 0≤b1+b2+b3≤0.5, 0≤c≤0.9, 0≤d≤0.9, 0≤e≤0.9, and 0≤f≤0.5; more preferably 0≤a1≤0.8, 0≤a2≤0.8, 0.1≤a1+a2≤0.8, 0≤b1≤0.4, 0≤b2≤0.4, 0≤b3≤0.4, 0≤b1+b2+b3≤0.4, 0≤c≤0.8, 0≤d≤0.8, 0≤e≤0.8, and 0≤f≤0.4; even more preferably 0≤a1≤0.7, 0≤a2≤0.7, 0.15≤a1+a2≤0.7, 0≤b1≤0.3, 0≤b2≤0.3, 0≤b3≤0.3, 0≤b1+b2+b3≤0.3, 0≤c≤0.7, 0≤d≤0.7, 0≤e≤0.7, and 0≤f≤0.3; and most preferably 0≤a1≤0.7, 0≤a2≤0.7, 0.15≤a1+a2≤0.7, 0≤b1≤0.3, 0≤b2≤0.3, 0≤b3≤0.3, 0.1≤b1+b2+b3≤0.3, 0<c≤0.7, 0≤d≤0.7, 0≤e≤0.7, and 0≤f≤0.3; provided a1+a2+b1+b2+b3+c+d+e+f=1.

The base resin may be synthesized by any desired method, for example, by dissolving monomers corresponding to the respective units (a1), (a2), (b1), (b2), (b3), (c), (d), (e), and (f) in an organic solvent, adding a radical polymerization initiator thereto, and heating for polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

In the case of a hydroxyl-containing monomer, the hydroxyl group may be replaced by an acetal group which is susceptible to deprotection with acid, typically ethoxyethoxy, prior to polymerization, and polymerization be followed by deprotection with weak acid and water. Alternatively, the hydroxyl group may have been replaced by an acetyl, formyl or pivaloyl group, and polymerization be followed by alkaline hydrolysis.

When hydroxystyrene or hydroxyvinylnaphthalene is to be copolymerized, one possible procedure is by carrying out polymerization using acetoxystyrene or acetoxyvinylnaphthalene instead of hydroxystyrene or hydroxyvinylnaphthalene, and effecting alkaline hydrolysis for deprotection of the acetoxy group for converting back to hydroxystyrene or hydroxyvinylnaphthalene units. Suitable bases used for alkaline hydrolysis include ammonia water and triethylamine. The reaction conditions include a temperature of −20° C. to 100° C., preferably 0° C. to 60° C. and a time of 0.2 to 100 hours, preferably 0.5 to 20 hours.

The base resin should preferably have a weight average molecular weight (Mw) in the range of 1,000 to 500,000, and more preferably 2,000 to 30,000, as measured in tetrahydrofuran (THF) solvent by GPC versus polystyrene standards. With a Mw of at least 1,000, the resist composition is fully heat resistant. A polymer with a Mw of up to 500,000 may be devoid of a loss of alkaline solubility or a footing phenomenon after pattern formation.

If a multi-component copolymer has a broad molecular weight distribution or dispersity (Mw/Mn), which indicates the presence of lower and higher molecular weight polymer fractions, there is a possibility that following exposure, foreign matter is left on the pattern or the pattern profile is exacerbated. The influences of molecular weight and disparity become stronger as the pattern rule becomes finer. Therefore, the base resin should preferably have a narrow dispersity (Mw/Mn) of 1.0 to 2.0, especially 1.0 to 1.5, in order to provide a resist composition suitable for micropatterning to a small feature size.

The base resin defined above is especially suited for use in a positive resist composition. It is acceptable to use as the base resin a blend of two or more such polymers which differ in compositional ratio, Mw or Mw/Mn or a blend of an inventive polymer and another polymer as long as the benefits of the invention are not impaired.

Other Components

A positive resist composition may be prepared by using the relevant base resin and sulfonic acid metal salt and combining them with suitable other components such as organic solvent, dissolution inhibitor, acid generator, surfactant, quencher, and acetylene alcohol. This resist composition has a very high sensitivity in that the base resin in the exposed region accelerates its dissolution rate in developer through catalytic reaction. The resist composition has many advantages including a high dissolution contrast, a high resolution, exposure latitude, process adaptability, a good pattern profile after exposure, high etch resistance, and minimized proximity bias due to controlled acid diffusion. Because of these advantages, the resist composition is fully viable in commercial processes and best suited as the micropatterning resist material for the fabrication of VLSIs. Particularly when an acid generator is added to formulate a chemically amplified positive resist composition capable of utilizing acid catalyzed reaction, the resist composition is quite useful by virtue of a higher sensitivity and better properties.

Examples of the organic solvent used herein are described in JP-A 2008-111103, paragraphs [0144]-[0145] (U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture. The organic solvent is preferably added in an amount of 100 to 10,000 parts, and more preferably 200 to 8,000 parts by weight per 100 parts by weight of the base resin.

When a dissolution inhibitor is added to the positive resist composition, the difference in dissolution rate between the exposed and unexposed regions is enhanced, with the resolution being further improved. When a basic compound is added, the rate of acid diffusion in the resist film can be suppressed, with the resolution being further improved. When a surfactant is added, the resist composition is further improved or controlled in coating operation. Suitable dissolution inhibitors are described in JP-A 2008-122932, paragraphs [0155]-[0178]. When used, the dissolution inhibitor is preferably added in an amount of 0.5 to 50 parts, more preferably 1 to 30 parts by weight per 100 parts by weight of the base resin.

In one preferred embodiment, the resist composition further contains an acid generator, typically a compound (PAG) capable of generating an acid in response to actinic ray or radiation. The PAG may be any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. Exemplary acid generators are described in U.S. Pat. No. 7,537,880 (JP-A 2008-111103, paragraphs [0122]-[0142]), JP-A 2009-080474, and JP-A 2015-026064.

Also, onium salts having the formulae (3) and (4) are preferred as the PAG.

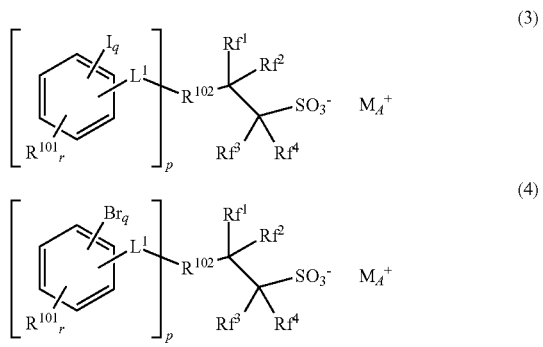

In formulae (3) and (4), $L^1$ is a single bond, ether bond, ester bond, or a $C_1$-$C_6$ alkylene group which may contain an ether bond or ester bond. The alkylene group may be straight, branched or cyclic.

In formulae (3) and (4), $R^{101}$ is hydroxyl, carboxyl, fluorine, chlorine, bromine, amino group, or a $C_1$-$C_{20}$ alkyl, $C_1$-$C_{20}$ alkoxy, $C_2$-$C_{20}$ alkoxycarbonyl, $C_2$-$C_{20}$ acyloxy or $C_1$-$C_{20}$ alkylsulfonyloxy group, which may contain fluorine, chlorine, bromine, hydroxy, amino or $C_1$-$C_{10}$ alkoxy moiety, or —$NR^8$—$C(=O)$—$R^9$ or —$NR^8$—$C(=O)$—$O$—$R^9$, wherein $R^8$ is hydrogen, or a $C_1$-$C_6$ alkyl group which may contain halogen, hydroxy, $C_1$-$C_6$ alkoxy, $C_2$-$C_6$ acyl or $C_2$-$C_6$ acyloxy moiety, and $R^9$ is a $C_1$-$C_{16}$ alkyl, $C_2$-$C_{16}$ is alkenyl, or $C_6$-$C_{12}$ aryl group, which may contain halogen, hydroxy, $C_1$-$C_6$ alkoxy, $C_2$-$C_6$ acyl or $C_2$-$C_6$ acyloxy moiety. The alkyl, alkoxy, alkoxycarbonyl, acyloxy, acyl, and alkenyl groups may be straight, branched or cyclic. Preferably, $R^{105}$ is hydroxyl, —$NR^8$—$C(=O)$—$R^9$, fluorine, chlorine, bromine, methyl or methoxy.

In formulae (3) and (4), $R^{102}$ is a single bond or a $C_1$-$C_{20}$ divalent linking group when p=1, or a $C_1$-$C_{20}$ tri- or tetravalent linking group when p=2 or 3, the linking group optionally containing an oxygen, sulfur or nitrogen atom.

In formulae (3) and (4), $Rf^{11}$ to $Rf^{14}$ are each independently hydrogen, fluorine or trifluoromethyl, at least one of $Rf^{11}$ to $Rf^{14}$ being fluorine or trifluoromethyl. $Rf^{11}$ and $Rf^{12}$, taken together, may form a carbonyl group.

In formulae (3) and (4), p is an integer of 1 to 3. Also, q is an integer of 1 to 5, r is an integer of 0 to 3, and q+r is 1 to 5. Preferably, q is an integer of 1 to 3, more preferably 2 or 3, and r is an integer of 0 to 2.

In formulae (3) and (4), $M_A^+$ is a sulfonium cation having the formula (5) or an iodonium cation having the formula (6).

In formulae (5) and (6), $R^{103}$, $R^{104}$, $R^{105}$, $R^{106}$, and $R^{107}$ are each independently a $C_1$-$C_{20}$ monovalent hydrocarbon group which may contain a heteroatom. Any two of $R^{103}$, $R^{104}$ and $R^{105}$ may bond together to form a ring with the sulfur atom to which they are attached. The monovalent hydrocarbon group may be straight, branched or cyclic, and examples thereof include $C_1$-$C_{12}$ alkyl, $C_2$-$C_{12}$ alkenyl, $C_2$-$C_{12}$ alkynyl, $C_6$-$C_{20}$ aryl, and $C_7$-$C_{12}$ aralkyl groups, with $C_6$-$C_{20}$ aryl groups being preferred. In the foregoing groups, at least one (one or more or even all) hydrogen may be substituted by hydroxyl, carboxyl, halogen, cyano, amide, nitro, mercapto, sultone, sulfone moiety or sulfonium salt-containing moiety, or at least one carbon may be substituted by an ether bond, ester bond, carbonyl moiety, carbonate moiety or sulfonic acid ester bond.

Examples of the anion in the onium salt having formula (3) or (4) include those which meet formula (3) or (4), selected from the aforementioned examples of the anion in the sulfonic acid metal salt having formula (1).

The acid generator may be used alone or in admixture. When used, the acid generator is preferably added in an amount of 0.1 to 50 parts by weight per 100 parts by weight of the base resin. Where the base resin contains recurring units of at least one type selected from recurring units (b1) to (b3), the resist composition may or may not contain the acid generator.

Exemplary surfactants are described in JP-A 2008-111103, paragraphs [0165]-[0166]. Inclusion of a surfactant may improve or control the coating characteristics of the resist composition. The surfactant may be used alone or in admixture. The surfactant is preferably added in an amount of 0.0001 to 10 parts by weight per 100 parts by weight of the base resin.

A quencher may be blended in the resist composition. The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the quencher. While an α-fluorinated sulfonic acid, imide acid, and methide acid are necessary to deprotect the acid labile group of carboxylic acid ester, an α-non-fluorinated sulfonic acid or carboxylic acid is released by salt exchange with an α-non-fluorinated onium salt. An α-non-fluorinated sulfonic acid and a carboxylic acid function as a quencher because they do not induce deprotection reaction.

An onium salt of carboxylic acid having the formula (7) is also an effective quencher.

$$R^{201}\text{—}CO_2^-M_B^+ \qquad (7)$$

In formula (7), $R^{201}$ is a $C_1$-$C_{40}$ monovalent hydrocarbon group which may contain a heteroatom. The monovalent hydrocarbon group may be straight, branched or cyclic, and examples thereof include $C_1$-$C_{40}$ alkyl, $C_2$-$C_{40}$ alkenyl, $C_2$-$C_{40}$ alkynyl, $C_6$-$C_{40}$ aryl, and $C_7$-$C_{40}$ aralkyl groups. In the foregoing groups, at least one (one or more or even all) hydrogen may be substituted by hydroxyl, carboxyl, halogen, cyano, amide, nitro, mercapto, sultone, sulfone moiety or sulfonium salt-containing moiety, or at least one carbon may be substituted by an ether bond, ester bond, carbonyl moiety, carbonate moiety or sulfonic acid ester bond.

In formula (7), $M_B^+$ is an onium cation. Examples of the onium cation include sulfonium, iodonium, and ammonium cations, with sulfonium or iodonium cations being preferred.

The preferred anion moiety in the carboxylic acid onium salt has the formula (8).

(8)

Herein $R^{202}$ and $R^{203}$ are each independently hydrogen, fluorine or trifluoromethyl. $R^{204}$ is hydrogen, hydroxyl or a $C_1$-$C_{35}$ monovalent hydrocarbon group which may contain a heteroatom. The monovalent hydrocarbon group any be straight, branched or cyclic, and examples thereof include $C_1$-$C_{35}$ alkyl, $C_2$-$C_{35}$ alkenyl, $C_2$-$C_{35}$ alkynyl, $C_6$-$C_{35}$ aryl, and $C_7$-$C_{35}$ aralkyl groups. In the foregoing groups, at least one (one or more or even all) hydrogen may be substituted by hydroxyl, carboxyl, halogen, cyano, amide, nitro, mercapto, sultone, sulfone moiety or sulfonium salt-containing moiety, or at least one carbon may be substituted by an ether bond, ester bond, carbonyl moiety, carbonate moiety or sulfonic acid ester bond.

Also useful are quenchers in the form of metal salts as described in U.S. Pat. No. 9,360,753 (JP-A 2013-025211). Suitable metal salts include salts of $C_1$-$C_{20}$ mono- to tetrafunctional carboxylic acid with a metal selected from sodium, magnesium, chromium, manganese, iron, cobalt, nickel, copper, zinc, silver, cadmium, indium, tin, antimony, cesium, zirconium and hafnium, and complexes of such metals with β-diketones.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

When used, the quencher is preferably added in an amount of 0.01 to 20 parts, more preferably 0.02 to 15 parts by weight per 100 parts by weight of the base resin. The quencher may be used alone or in admixture. When a quencher of polymer type is used, its amount is arbitrary as long as the benefits of the invention are not impaired.

Suitable acetylene alcohols are described in JP-A 2008-122932, paragraphs [0179]-[0182]. An appropriate amount of the acetylene alcohol blended is 0 to 2% by weight, more preferably 0.02 to 1% by weight based on the resist composition.

Process

Another embodiment of the invention is a pattern forming process comprising the steps of coating the resist composition defined above onto a substrate, baking the coating to form a resist film, exposing the resist film to high-energy radiation, and developing the exposed resist film in a developer. The step of exposing the resist film to high-energy radiation may use EUV of wavelength 3 to 15 nm or EB, specifically EB at an accelerating voltage of 1 to 150 kV as the energy source.

Since the sulfonic acid metal salt having formula (1) is an electrically conductive metal salt, it is effective for preventing any charge buildup in the resist film during EB image writing. It is then not necessarily essential to form an antistatic film on the resist film. Since the salt having formula (1) is strongly absorptive to EUV of wavelength 13.5 nm, the sensitivity of the resist film is increased upon exposure to EUV by the mechanism that the outer shell electrons of the metal are excited, and the elections transfer to the acid generator, whereby the efficiency of acid generation is enhanced.

When the resist composition is used for the microfabrication of various integrated circuits, any well-known lithography processes may be applied. For example, the resist composition is applied onto a substrate for integrated circuit fabrication or a processable layer thereon (e.g., Si, $SiO_2$, SiN, SiON, TiN, WSi, BPSG, SOG, or organic antireflective coating) or a substrate for mask circuit fabrication or a processable layer thereon (e.g., Cr, CrO, CrON, $MoSi_2$ or $SiO_2$) by any suitable technique such as spin coating, roll coating, flow coating, dip coating, spray coating or doctor coating. The coating is prebaked on a hotplate at a temperature of 60 to 150° C. for 10 seconds to 30 minutes, preferably at 80 to 120° C. for 30 seconds to 20 minutes to form a resist film having a thickness of 0.01 to 2 μm.

Next the resist film is exposed imagewise to high-energy radiation selected from among UV, DUV, EB, x-ray, soft x-ray, excimer laser, γ-ray, synchrotron radiation, or EUV directly or through a mask having the desired pattern. The exposure is preferably carried out to provide a dose of 1 to 200 mJ/cm³, preferably 10 to 100 mJ/cm², or 0.1 to 100 μC/cm², preferably 0.5 to 50 μC/cm². This is followed by baking (PEB) on a hotplate at 60 to 150° C. for 10 seconds to 30 minutes, preferably at 80 to 120° C. for 30 seconds to 20 minutes.

Finally, the exposed resist film is developed with a developer which is an aqueous alkaline solution, typically a 0.1 to 10%, preferably 2 to 5% by weight of tetramethylammonium hydroxide (TMAH), choline hydroxide, tetraethylammonium hydroxide (TEAH), tetrapropylammonium hydroxide (TPAH), tetrabutylammonium hydroxide (TBAH), benzyltrimethylammonium hydroxide or benzyltriethylammonium hydroxide. Development is carried out for 3 seconds to 3 minutes, preferably 5 seconds to 2 minutes by any conventional techniques such as dip, puddle and spray techniques. The exposed region of resist film is dissolved in the developer, but not the unexposed region. In this way, the desired positive pattern is formed on the substrate.

Alternatively, a negative tone pattern may be formed by organic solvent development. The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Besides the foregoing solvents, aromatic solvents may be used, for example, toluene, xylene, ethylbenzene, isopropylbenzene, t-butylbenzene and mesitylene. The solvents may be used alone or in admixture.

Of the variety of high-energy radiation, the resist composition is best suited in micropatterning with EB, EUV, x-ray, soft x-ray, γ-ray, or synchrotron radiation. Particularly when EUV of wavelength 3 to 15 nm or an accelerated EB at an accelerating voltage of 1 to 150 kV, preferably 1 to 100 kV, especially a low voltage accelerated EB at an accelerating voltage of 1 to 50 kV is used, a finer size pattern can be formed.

EXAMPLE

Examples are given below by way of illustration of the invention and not by way of limitation. The abbreviation "pbw" is parts by weight. For all polymers, Mw and Mn are determined versus polystyrene standards by GPC using THF solvent.

[1] Synthesis of Sulfonic Acid Metal Salt

Synthesis Example 1-1

Synthesis of benzyltrimethylammonimn 2-[4-(2,3,5-triiodobenzoyloxy)-butyryloxy]-1,1,3,3,3-pentafluoropropane-1-sulfonate

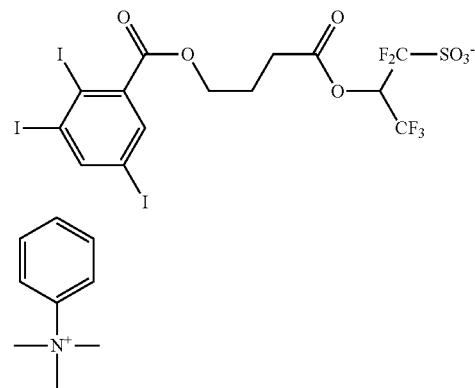

Benzyltrimethylammonium 2-(4-chlorobutyryloxy)-1,1,3,3,3-pentafluoropropane-1-sulfonate was prepared with reference to Synthesis Example 1-24-1 of U.S. Pat. No. 7,670,751 (JP 5019071), aside from using benzyltrimethylammonium 2-hydroxy-1,1,3,3,3-pentafluoropropane-1-sulfonate instead of triphenylsulfonium 2-hydroxy-1,1,3,3,3-pentafluoropropane-1-sulfonate.

Next, 16 g of benzyltrimethylammonium 2-(4-chlorobutyryloxy)-1,1,3,3,3-pentafluoropropane-1-sulfonate prepared above, 20 g of 2,3,5-triiodobenzoic acid, 0.5 g of sodium iodide, 6.1 g of potassium carbonate, and 200 mL of dimethylformamide were mixed and stirred overnight at 90° C. Once the solution was cooled down to room temperature, some dimethylformamide was removed under reduced pressure. Methyl isobutyl ketone (MIBK) was added to the residue, which was washed with water. Water washing was followed by concentration under reduced pressure. To the residue, diisopropyl ether was added for crystallization. The precipitate was collected by filtration and heat dried in vacuum, obtaining the target compound, benzyltrimethylammonium 2-[4-(2,3,5-triiodobenzoyloxy)-butyryloxy]-1,1,3,3,3-pentafluoropropane-1-sulfonate (23 g, yield 71%).

Synthesis Example 1-2

Synthesis of barium 2-[4-(2,3,5-triiodobenzoyloxy)-butyryloxy]-1,1,3,3,3-pentafluoropropane-1-sulfonate

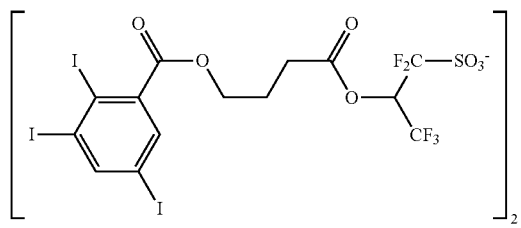

In 43 g of methanol was dissolved 14 g of benzyltrimethylammonium 2-[4-(2,3,5-triiodobenzoyloxy)-butyryloxy]-1,1,3,3,3-pentafluoropropane-1-sulfonate prepared above. To the solution, 42 g of ion exchange resin Duolite® 255LFH (Sumika Chemtex Co., Ltd.) was added. The mixture was agitated for 2 hours. The ion exchange resin was filtered off. The filtrate was concentrated under reduced pressure to remove methanol. Under ice cooling, 1.6 g of barium hydroxide octahydrate and 50 g of deionized water were added to the concentrate, which was stirred for 30 minutes. The stirring was followed by concentration in vacuum. MIBK was added to the concentrate, followed by concentration in vacuum again. To the residue, diisopropyl ether was added for crystallization. The precipitate was collected by filtration and heat dried in vacuum, obtaining the target compound, barium 2-[4-(2,3,5-triiodobenzoyloxy)-butyryloxy]-1,1,3,3,3-pentafluoropropane-1-sulfonate (Barium Salt 1-1) (4.7 g, yield 50%).

Synthesis Examples 1-3 to 1-17

Synthesis of Barium Salts 1-2 to 1-8, Cesium Salt 1-1, Rubidium Salt 1-1, Strontium Salt 1-1, Cerium Salt 1-1, Magnesium Salts 1-1 to 1-3, and Calcium Salt 1-1

Barium Salts 1-2 to 1-8, Cesium Salt 1-1, Rubidium Salt 1-1, Strontium Salt 1-1, Cerium Salt 1-1, Magnesium Salts 1-1 to 1-3, and Calcium Salt 1-1 were synthesized by the same procedure as in Synthesis Example 1-2 except that the type of anion and or the type of metal in metal hydroxide was changed.

Barium Salts 1-1 to 1-8, Cesium Salt 1-1, Rubidium Salt 1-1, Strontium Salt 1-1, Cerium Salt 1-1, Magnesium Salts 1-1 to 1-3, and Calcium Salt 1-1 are identified below by their structure formula.

Barium Salt 1-1

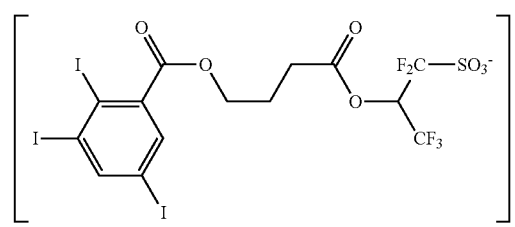

Balium Salt 1-2

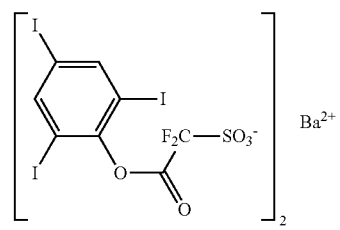

Balium Salt 1-3

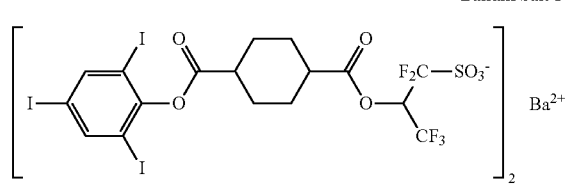

Balium Salt 1-4

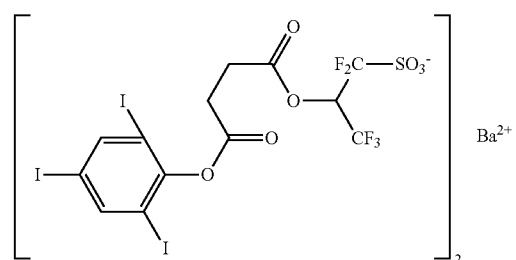

Balium Salt 1-5

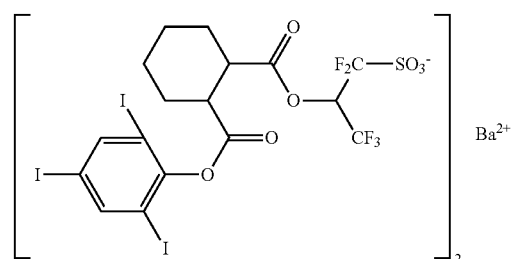

Balium Salt 1-6

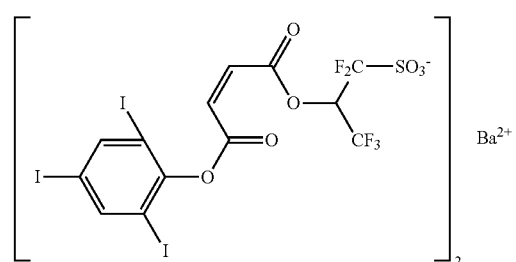

Balium Salt 1-7

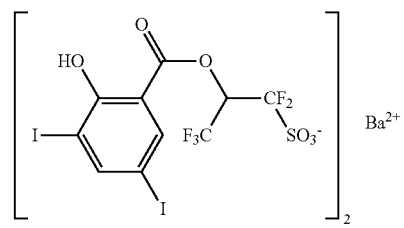

Balium Salt 1-8

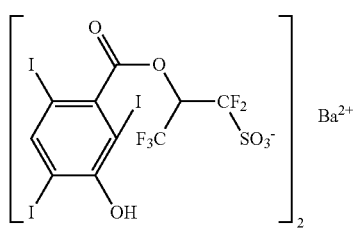

Cesrium Salt 1-1

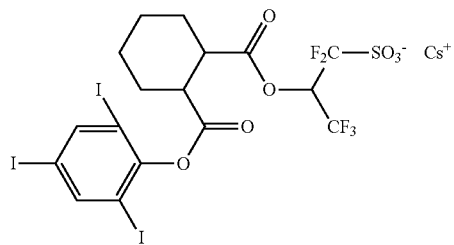

Rubidium Salt 1-1

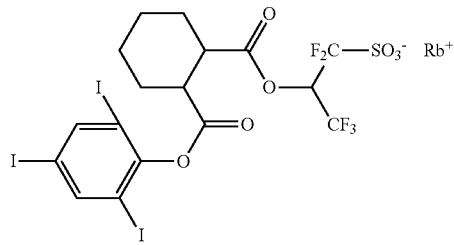

Strontium Salt 1-1

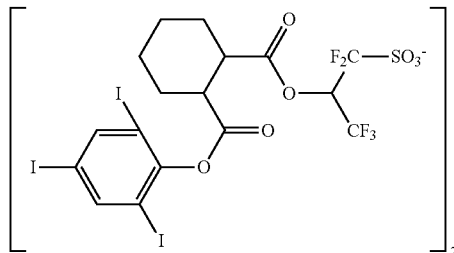

Cerium Salt 1-1

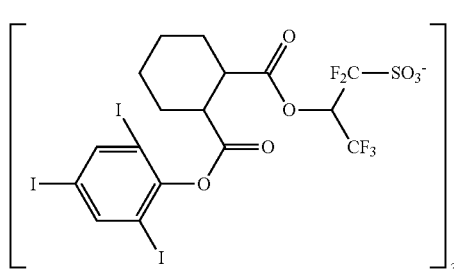

Magnesium Salt 1-1

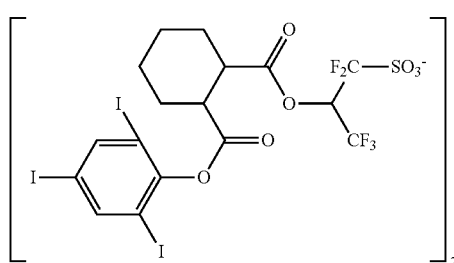

Magnesium Salt 1-2

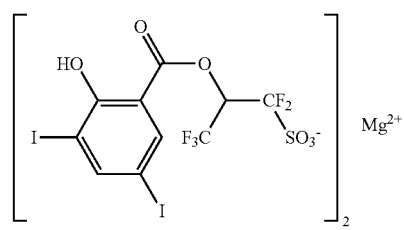

Magnesium Salt 1-3

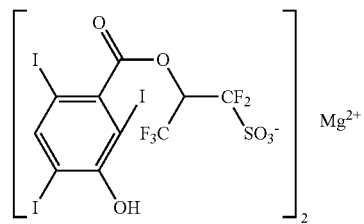

Calsium Salt 1-1

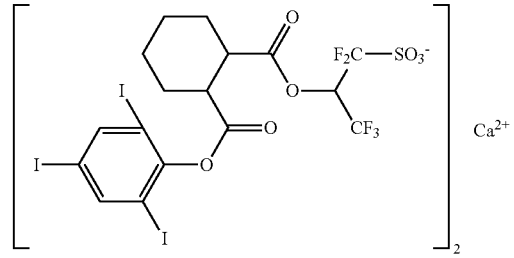

Synthesis Examples 2-1 to 2-16

Synthesis of Barium Salts 2-1 to 2-8, Cesium Salt 2-1, Rubidium Salt 2-1, Strontium Salt 2-1, Cerium Salt 2-1, Magnesium Salts 2-1 to 2-3, and Calcium Salt 2-1

Barium Salts 2-1 to 2-8, Cesium Salt 2-1, Rubidium Salt 2-1, Strontium Salt 2-1, Cerium Salt 2-1, Magnesium Salts 2-1 to 2-3, and Calcium Salt 2-1 were synthesized by the same procedure as in Synthesis Example 1-2 except that the type of anion and or the type of metal in metal hydroxide was changed.

Barium Salts 2-1 to 2-8, Cesium Salt 2-1, Rubidium Salt 2-1, Strontium Salt 2-1, Cerium Salt 2-1, Magnesium Salts 2-1 to 2-3, and Calcium Salt 2-1 are identified below by then structure formula.

Balium Salt 2-1

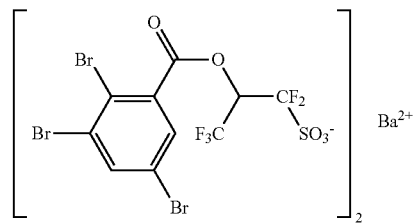

Balium Salt 2-2
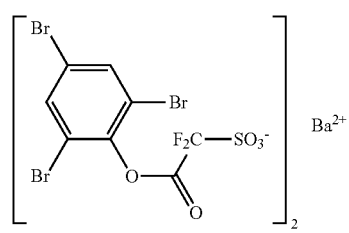
Balium Salt 2-3
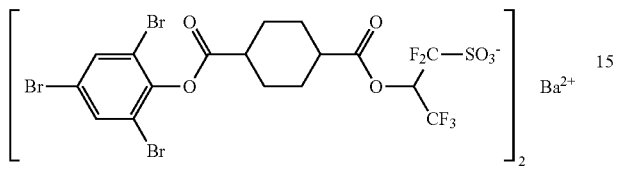
Balium Salt 2-4
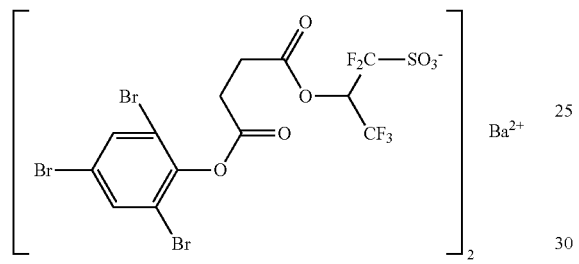
Balium Salt 2-5
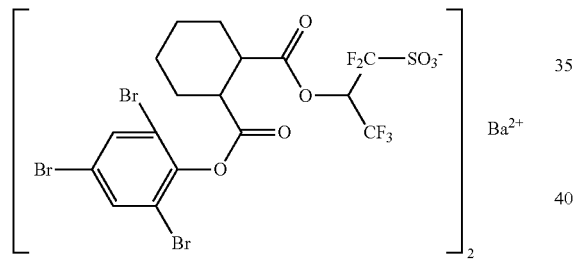
Balium Salt 2-6
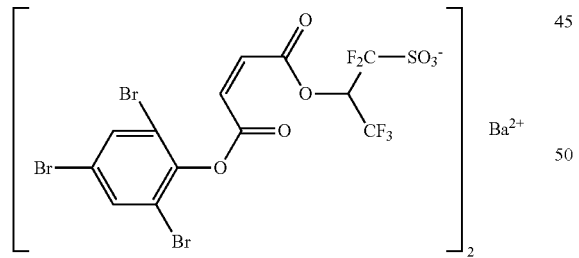
Balium Salt 2-7
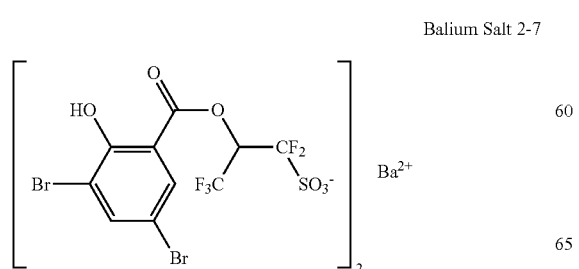
Balium Salt 2-8
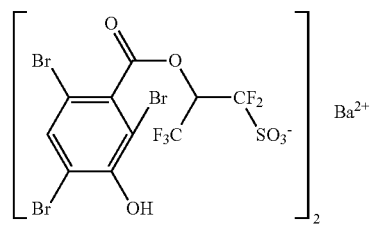
Cesium Salt 2-1
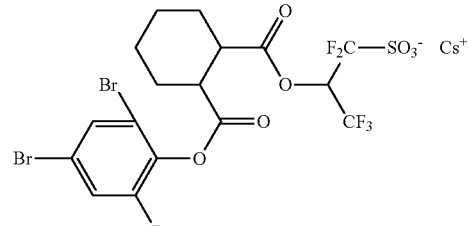
Rubidium Salt 2-1
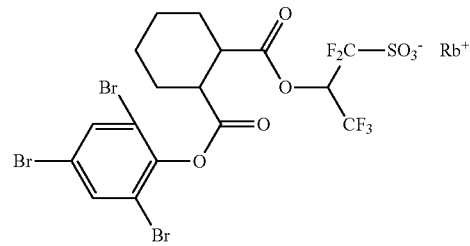
Strontium Salt 2-1
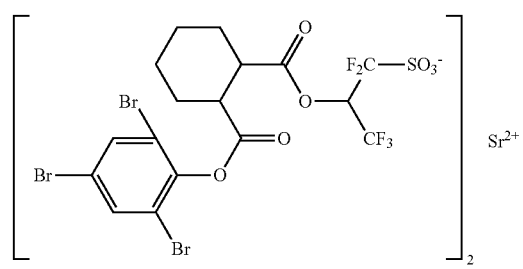
Cerium Salt 2-1
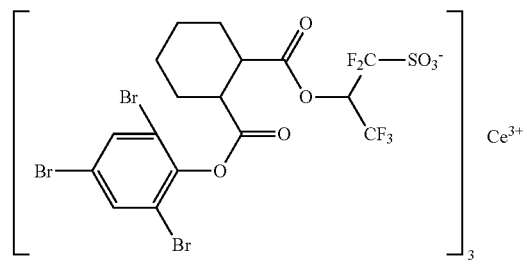
Magnesium Salt 2-1
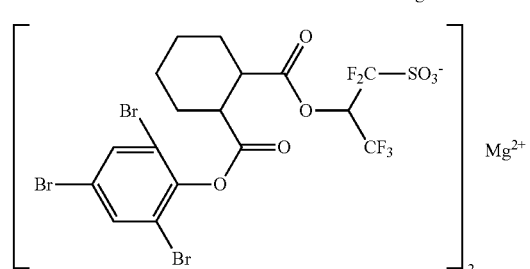

Magnesium Salt 2-2

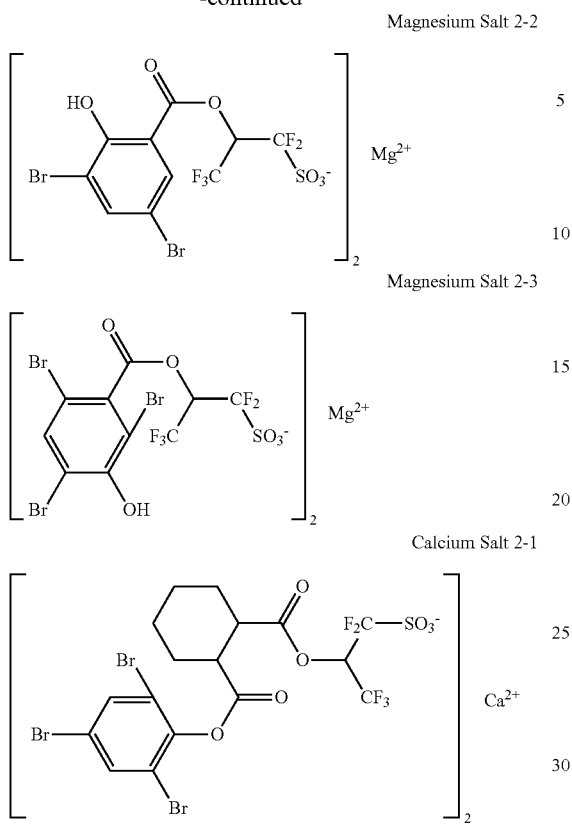

Magnesium Salt 2-3

Calcium Salt 2-1

[2] Synthesis of Base Resins

Various base resins (Polymers 1 to 5) were prepared by combining suitable monomers, effecting copolymerization reaction in THF solvent, pouring into methanol for crystallization, repeatedly washing with hexane, isolation, and drying. The base resins were analyzed by $^1$H-NMR to determine their composition and by GPC to determine Mw and dispersity Mw/Mn.

Synthesis Example 3-1

Polymer 1

Mw=7,900
Mw/Mn=1.97

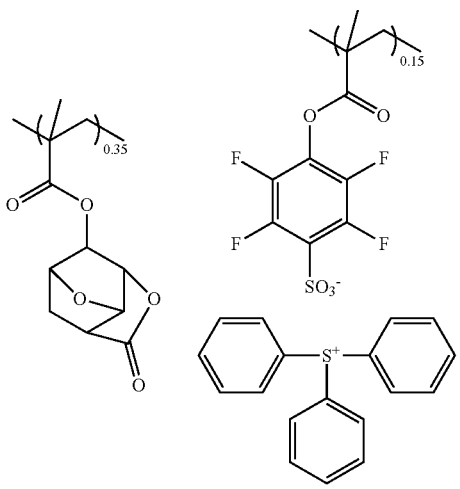

Synthesis Example 3-2

Polymer 2

Mw=8,300
Mw/Mn=1.98

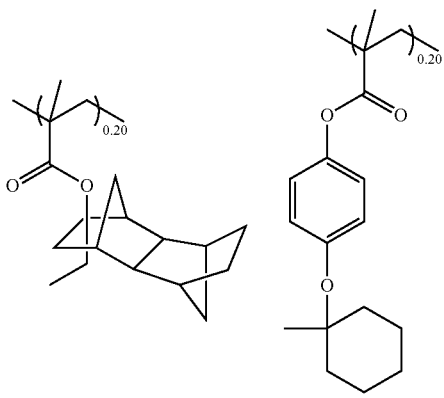

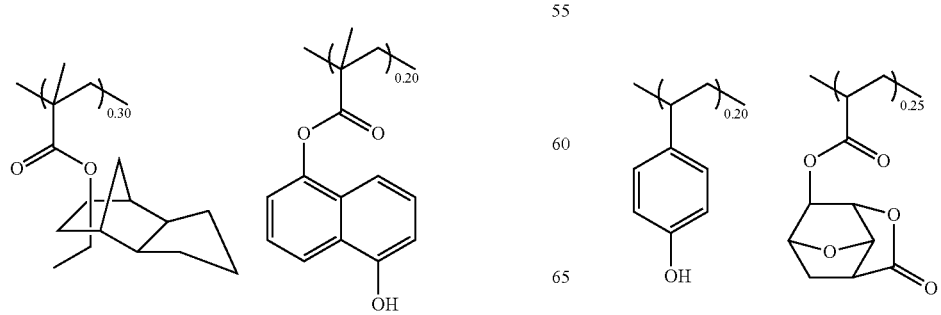

-continued
Synthesis Example 3-3
Polymer 3
Mw=8,300
Mw/Mn=1.76
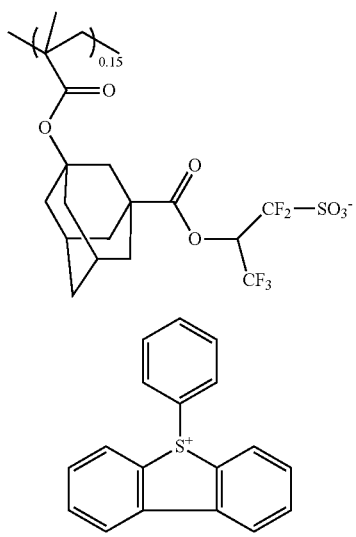
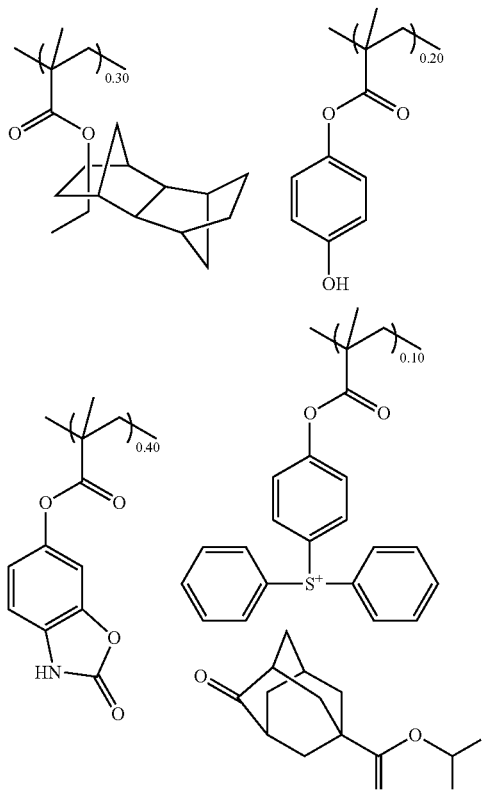
Synthesis Example 3-4
Polymer 4
Mw=9,000
Mw/Mn=1.98
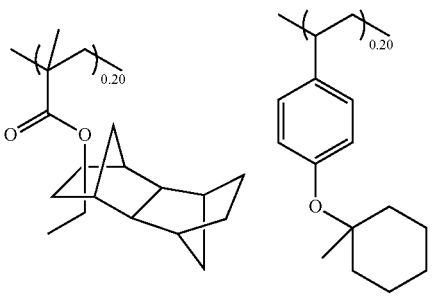
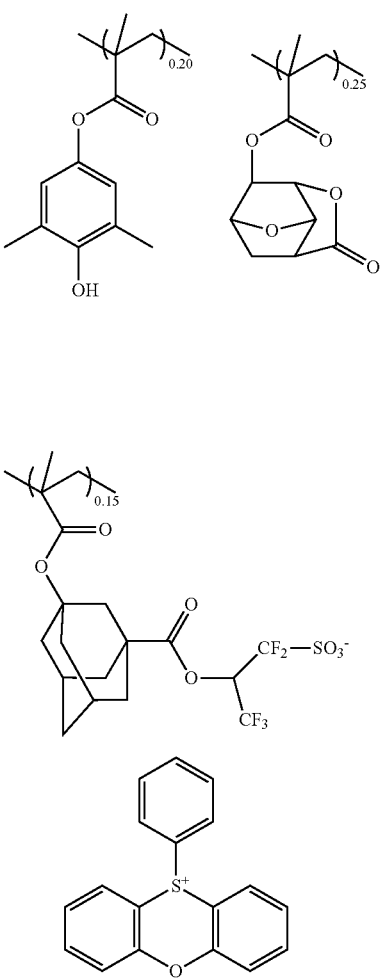

Synthesis Example 3-5

Polymer 5

Mw=8,400
Mw/Mn=1.91

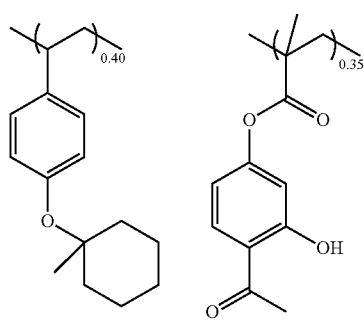

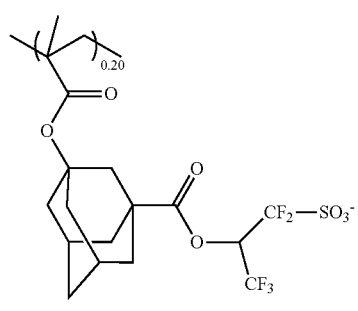

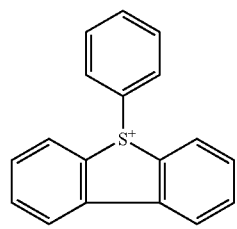

[3] Preparation of Resist Composition

Examples 1-1 to 1-24 and 2-1 to 2-20 & Comparative Examples 1-1 to 1-3

Positive resist compositions in solution form were prepared by dissolving a base resin (synthesized above) and selected components in a solvent in accordance with the formulation of Tables 1 to 3 and filtering through a filter with a pore size of 0.2 μm. The solvent contained 100 ppm of surfactant FC-4430 (commercially available from 3M).

The components in Tables 1 to 3 are identified below.

Acid/generator: PAG 1 to PAG 6 of the following structural formulae

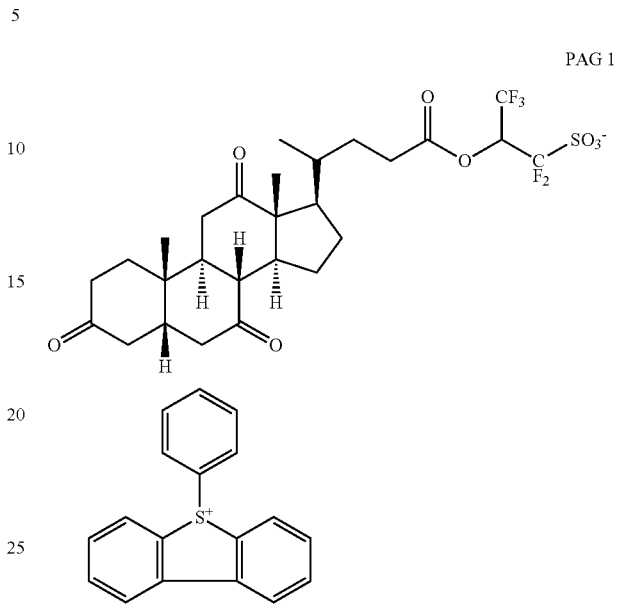

PAG 1

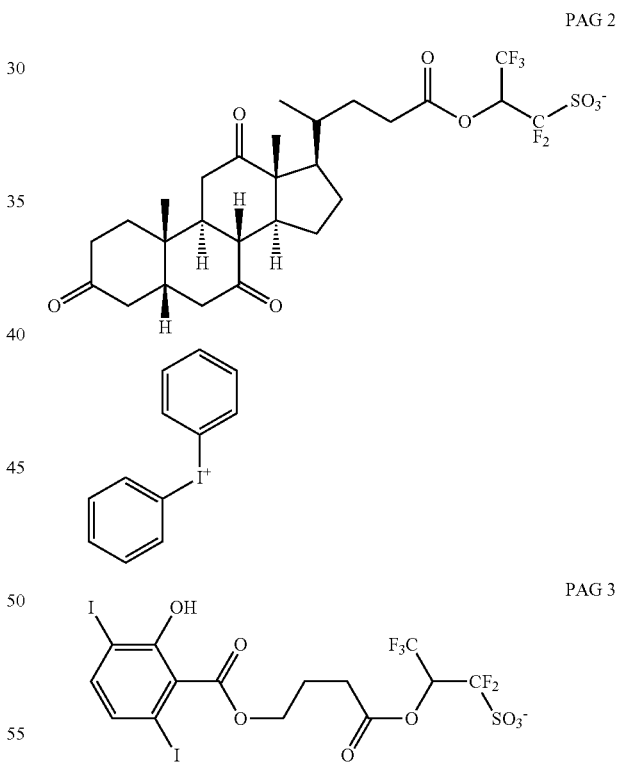

PAG 2

PAG 3

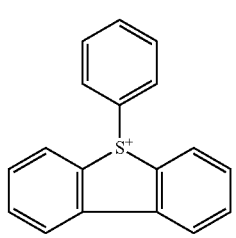

PAG 4

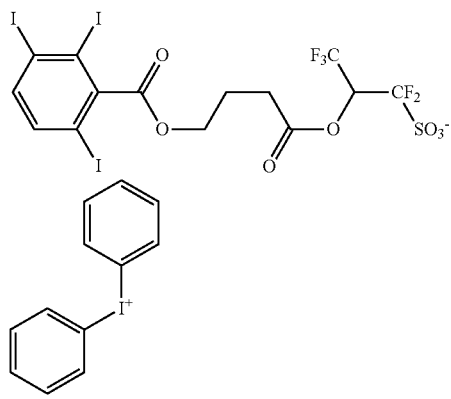

PAG 5

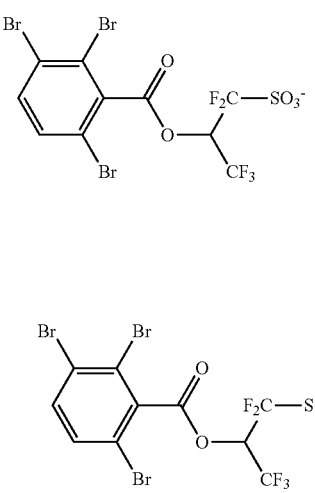
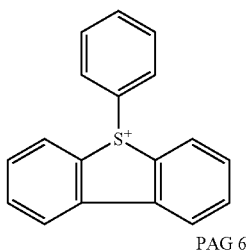

PAG 6

Quencher:
Amine 1, Amine 2, cesium pivalate, Quenchers 1 and 2 of the following structural formulae Amine 1

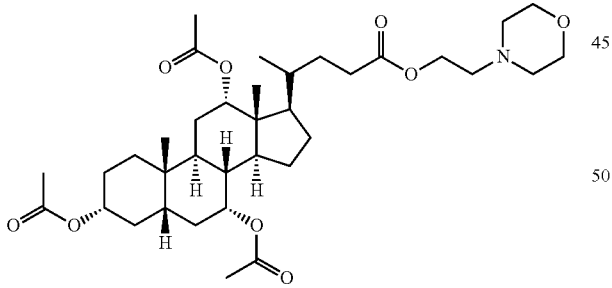

Amine 2

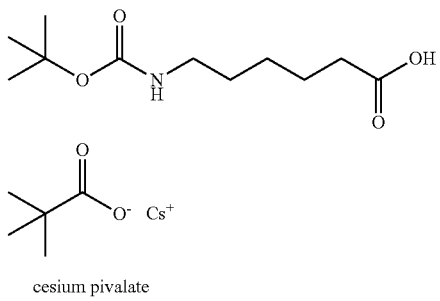

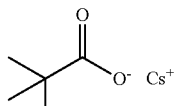

cesium pivalate

Quencher 1

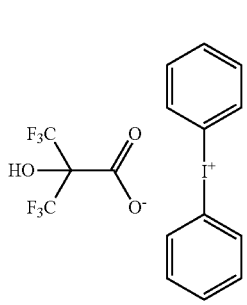

Quencher 2

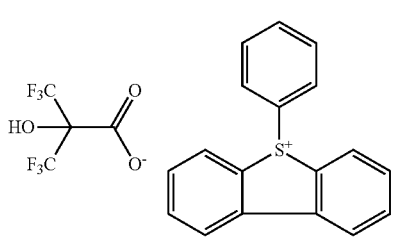
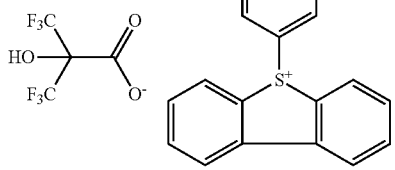

Organic Solvents:
PGMEA (propylene glycol monomethyl ether acetate)
PGME (propylene glycol monomethyl ether)
CyH (cyclohexanone)
GBL (γ-butyrolactone)
DAA (diacetone alcohol)

TABLE 1

|  |  | Resist | Polymer (pbw) | Metal compound (pbw) | Acid generator (pbw) | Quencher (pbw) | Organic solvent (pbw) |
| --- | --- | --- | --- | --- | --- | --- | --- |
| Example | 1-1 | Resist 1-1 | Polymer 1 (100) | Barium Salt 1-1 (8.0) | — | Amine 1 (1.3) | PGMEA (1,000) CyH (1,000) GBL (200) |
|  | 1-2 | Resist 1-2 | Polymer 2 (100) | Barium Salt 1-1 (8.0) | — | Amine 1 (1.3) | PGMEA (1,000) CyH (1,100) PGME (100) |

TABLE 1-continued

|  | Resist | Polymer (pbw) | Metal compound (pbw) | Acid generator (pbw) | Quencher (pbw) | Organic solvent (pbw) |
|---|---|---|---|---|---|---|
| 1-3 | Resist 1-3 | Polymer 3 (100) | Barium Salt 1-1 (8.0) | — | Amine 1 (1.3) | PGMEA (1,000) CyH (1,000) GBL (200) |
| 1-4 | Resist 1-4 | Polymer 4 (100) | Barium Salt 1-1 (8.0) | — | Amine 1 (1.3) | PGMEA (2,000) DAA (400) |
| 1-5 | Resist 1-5 | Polymer 5 (100) | Barium Salt 1-1 (8.0) | — | Amine 1 (1.3) | PGMEA (2,000) DAA (400) |
| 1-6 | Resist 1-6 | Polymer 1 (100) | Barium Salt 1-2 (8.0) | — | Amine 2 (0.5) | PGMEA (2,000) DAA (400) |
| 1-7 | Resist 1-7 | Polymer 1 (100) | Barium Salt 1-3 (9.1) | — | Amine 1 (1.3) | PGMEA (2,000) DAA (400) |
| 1-8 | Resist 1-8 | Polymer 1 (100) | Barium Salt 1-4 (11.2) | — | Amine 1 (1.3) | PGMEA (2,000) DAA (400) |
| 1-9 | Resist 1-9 | Polymer 1 (100) | Barium Salt 1-5 (9.2) | — | Amine 1 (1.3) | PGMEA (2,000) DAA (400) |
| 1-10 | Resist 1-10 | Polymer 1 (100) | Barium Salt 1-6 (9.2) | — | Amine 1 (1.3) | PGMEA (2,000) DAA (400) |
| 1-11 | Resist 1-11 | Polymer 1 (100) | Barium Salt 1-7 (9.2) | — | Amine 1 (1.3) | PGMEA (2,000) DAA (400) |
| 1-12 | Resist 1-12 | Polymer 1 (100) | Barium Salt 1-8 (9.2) | — | Amine 1 (1.3) | PGMEA (2,000) DAA (400) |
| 1-13 | Resist 1-13 | Polymer 1 (100) | Cesium Salt 1-1 (2.9) | — | Amine 1 (1.3) | PGMEA (2,000) DAA (400) |
| 1-14 | Resist 1-14 | Polymer 1 (100) | Rubidium Salt 1-1 (7.8) | — | Amine 1 (1.3) | PGMEA (2,000) DAA (400) |
| 1-15 | Resist 1-15 | Polymer 1 (100) | Strontium Salt 1-1 (10.6) | — | cesium pivalate (1.2) | PGMEA (2,000) DAA (400) |
| 1-16 | Resist 1-16 | Polymer 1 (100) | Cerium Salt 1-1 (9.6) | — | cesium pivalate (1.2) | PGMEA (2,000) DAA (400) |
| 1-17 | Resist 1-17 | Polymer 1 (100) | Magnesium Salt 1-1 (6.6) | — | cesium pivalate (1.2) | PGMEA (2,000) DAA (400) |
| 1-18 | Resist 1-18 | Polymer 1 (100) | Magnesium Salt 1-2 (6.6) | — | cesium pivalate (1.2) | PGMEA (2,000) DAA (400) |
| 1-19 | Resist 1-19 | Polymer 1 (100) | Magnesium Salt 1-3 (6.6) | PAG 1 (5.0) | Quencher 1 (4.0) | PGMEA (2,000) DAA (400) |
| 1-20 | Resist 1-20 | Polymer 1 (100) | Calcium Salt 1-1 (7.6) | PAG 2 (6.0) | Quencher 2 (3.5) | PGMEA (2,000) DAA (400) |
| 1-21 | Resist 1-21 | Polymer 1 (100) | Barium Salt 1-1 (4.0) | PAG 3 (5.0) | Quencher 2 (3.5) | PGMEA (2,000) DAA (400) |
| 1-22 | Resist 1-22 | Polymer 1 (100) | Barium Salt 1-1 (4.0) | PAG 4 (5.0) | Quencher 2 (3.5) | PGMEA (2,000) DAA (400) |
| 1-23 | Resist 1-23 | Polymer 1 (100) | Barium Salt 1-1 (4.0) | PAG 5 (5.0) | Quencher 2 (3.5) | PGMEA (2,000) DAA (400) |
| 1-24 | Resist 1-24 | Polymer 1 (100) | Barium Salt 1-1 (4.0) | PAG 6 (5.0) | Quencher 2 (3.5) | PGMEA (2,000) DAA (400) |

TABLE 2

|  |  | Resist | Polymer (pbw) | Metal compound (pbw) | Acid generator (pbw) | Quencher (pbw) | Organic solvent (pbw) |
|---|---|---|---|---|---|---|---|
| Example | 2-1 | Resist 2-1 | Polymer 1 (100) | Barium Salt 2-1 (8.0) | — | Amine 1 (1.3) | PGMEA (1,000) CyH (1,000) GBL (200) |
|  | 2-2 | Resist 2-2 | Polymer 2 (100) | Barium Salt 2-1 (8.0) | — | Amine 1 (1.3) | PGMEA (1,000) CyH (1,100) PGME (100) |
|  | 2-3 | Resist 2-3 | Polymer 3 (100) | Barium Salt 2-1 (8.0) | — | Amine 1 (1.3) | PGMEA (1,000) CyH (1,000) GBL (200) |
|  | 2-4 | Resist 2-4 | Polymer 4 (100) | Barium Salt 2-1 (8.0) | — | Amine 1 (1.3) | PGMEA (2,000) DAA (400) |
|  | 2-5 | Resist 2-5 | Polymer 5 (100) | Barium Salt 2-1 (8.0) | — | Amine 1 (1.3) | PGMEA (2,000) DAA (400) |
|  | 2-6 | Resist 2-6 | Polymer 1 (100) | Barium Salt 2-2 (8.0) | — | Amine 2 (0.5) | PGMEA (2,000) DAA (400) |
|  | 2-7 | Resist 2-7 | Polymer 1 (100) | Barium Salt 2-3 (9.1) | — | Amine 1 (1.3) | PGMEA (2,000) DAA (400) |
|  | 2-8 | Resist 2-8 | Polymer 1 (100) | Barium Salt 2-4 (11.2) | — | Amine 1 (1.3) | PGMEA (2,000) DAA (400) |
|  | 2-9 | Resist 2-9 | Polymer 1 (100) | Barium Salt 2-5 (9.2) | — | Amine 1 (1.3) | PGMEA (2,000) DAA (400) |

TABLE 2-continued

| Resist | | Polymer (pbw) | Metal compound (pbw) | Acid generator (pbw) | Quencher (pbw) | Organic solvent (pbw) |
|---|---|---|---|---|---|---|
| 2-10 | Resist 2-10 | Polymer 1 (100) | Barium Salt 2-6 (9.2) | — | Amine 1 (1.3) | PGMEA (2,000) DAA (400) |
| 2-11 | Resist 2-11 | Polymer 1 (100) | Barium Salt 2-7 (9.2) | — | Amine 1 (1.3) | PGMEA (2,000) DAA (400) |
| 7-12 | Resist 2-12 | Polymer 1 (100) | Barium Salt 2-8 (9.2) | — | Amine 1 (1.3) | PGMEA (2,000) DAA (400) |
| 2-13 | Resist 2-13 | Polymer 1 (100) | Cesium Salt 2-1 (2.9) | — | Amine 1 (1.3) | PGMEA (2,000) DAA (400) |
| 2-14 | Resist 2-14 | Polymer 1 (100) | Rubidium Salt 2-1 (7.8) | — | Amine 1 (1.3) | PGMEA (2,000) DAA (400) |
| 2-15 | Resist 2-15 | Polymer 1 (100) | Strontium Salt 2-1 (10.6) | — | cesium pivalate (1.2) | PGMEA (2,000) DAA (400) |
| 2-16 | Resist 2-16 | Polymer 1 (100) | Cerium Salt 2-1 (9.6) | — | cesium pivalate (1.2) | PGMEA (2,000) DAA (400) |
| 2-17 | Resist 2-17 | Polymer 1 (100) | Magnesium Salt 2-1 (6.6) | — | cesium pivalate (1.2) | PGMEA (2,000) DAA (400) |
| 2-18 | Resist 2-18 | Polymer 1 (100) | Magnesium Salt 2-2 (6.6) | — | cesium pivalate (1.2) | PGMEA (2,000) DAA (400) |
| 2-19 | Resist 2-19 | Polymer 1 (100) | Magnesium Salt 2-3 (6.6) | — | Quencher 1 (4.0) | PGMEA (2,000) DAA (400) |
| 2-20 | Resist 2-20 | Polymer 1 (100) | Calcium Salt 2-1 (7.6) | — | Quencher 2 (3.5) | PGMEA (2,000) DAA (400) |

TABLE 3

| | | Resist | Polymer (bpw) | Metal compound (pbw) | Acid generator (pbw) | Quencher (pbw) | Organic solvent (pbw) |
|---|---|---|---|---|---|---|---|
| Comparative Example | 1-1 | Comparative Resist 1 | Polymer 1 (100) | — | — | Amine 1 (1.3) | PGMEA (2,000) DAA (400) |
| | 1-2 | Comparative Resist 2 | Polymer 1 (100) | — | — | Amine 1 (0.6) | PGMEA (2,000) DAA (400) |
| | 1-3 | Comparative Resist 3 | Polymer 1 (100) | — | — | cesium pivalate (1.2) | PGMEA (2,000) DAA (400) |

[4] EB Writing Test

Examples 3-1 to 3-24 and 4-1 to 4-20 & Comparative Examples 2-1 to 2-3

A silicon substrate was coated with an antireflective coating of 60 nm thick (DUV-62, Nissan Chemical Corp.). Each of the resist compositions in Tables 1 to 3 was spin coated on the substrate and prebaked on a hotplate at 105° C. for 60 seconds to form a resist film of 50 nm thick. The resist film was exposed to election beam using an EB lithography system ELS-F125 (Elionix Co., Ltd., accelerating voltage 125 kV), then baked (PEB) on a hotplate at the temperature shown in Tables 4 to 6 for 60 seconds, and developed with a 2.38 wt % TMAH aqueous solution for 30 seconds to form a hole pattern having a size of 24 nm.

The resist pattern was observed under CD-SEM (CG-5000, Hitachi High-Technologies Corp.). The exposure dose that provides a hole pattern having a size of 24 nm is reported as sensitivity. The size of 50 holes was measured, from which a size variation (3σ) was computed and reported as CDU. The results are shown in Tables 4 to 6.

TABLE 4

| | | Resist | PEB temp. (° C.) | Sensitivity (μC/cm$^2$) | CDU (nm) |
|---|---|---|---|---|---|
| Example | 3-1 | Resist 1-1 | 85 | 155 | 6.1 |
| | 3-2 | Resist 1-2 | 80 | 135 | 5.2 |

TABLE 4-continued

| | Resist | PEB temp. (° C.) | Sensitivity (μC/cm$^2$) | CDU (nm) |
|---|---|---|---|---|
| 3-3 | Resist 1-3 | 80 | 130 | 5.3 |
| 3-4 | Resist 1-4 | 80 | 150 | 5.1 |
| 3-5 | Resist 1-5 | 70 | 140 | 5.3 |
| 3-6 | Resist 1-6 | 85 | 120 | 5.4 |
| 3-7 | Resist 1-7 | 85 | 110 | 6.1 |
| 3-8 | Resist 1-8 | 85 | 123 | 5.7 |
| 3-9 | Resist 1-9 | 85 | 122 | 5.5 |
| 3-10 | Resist 1-10 | 85 | 123 | 5.2 |
| 3-11 | Resist 1-11 | 85 | 128 | 4.8 |
| 3-12 | Resist 1-12 | 85 | 121 | 5.6 |
| 3-13 | Resist 1-13 | 85 | 125 | 5.6 |
| 3-14 | Resist 1-14 | 85 | 118 | 5.9 |
| 3-15 | Resist 1-15 | 85 | 119 | 5.6 |
| 3-16 | Resist 1-16 | 85 | 120 | 5.6 |
| 3-17 | Resist 1-17 | 85 | 125 | 5.6 |
| 3-18 | Resist 1-18 | 85 | 118 | 5.9 |
| 3-19 | Resist 1-19 | 85 | 103 | 5.6 |
| 3-20 | Resist 1-20 | 85 | 83 | 5.6 |
| 3-21 | Resist 1-21 | 85 | 100 | 5.8 |
| 3-22 | Resist 1-22 | 85 | 95 | 5.9 |
| 3-23 | Resist 1-23 | 85 | 95 | 5.9 |
| 3-24 | Resist 1-24 | 85 | 90 | 5.8 |

TABLE 5

| | | Resist | PEB temp. (° C.) | Sensitivity (μC/cm²) | CDU (nm) |
|---|---|---|---|---|---|
| Example | 4-1 | Resist 2-1 | 85 | 135 | 6.4 |
| | 4-2 | Resist 2-2 | 80 | 125 | 5.2 |
| | 4-3 | Resist 2-3 | 80 | 120 | 5.6 |
| | 4-4 | Resist 2-4 | 80 | 140 | 5.7 |
| | 4-5 | Resist 2-5 | 70 | 120 | 5.8 |
| | 4-6 | Resist 2-6 | 85 | 110 | 5.6 |
| | 4-7 | Resist 2-7 | 85 | 100 | 6.0 |
| | 4-8 | Resist 2-8 | 85 | 115 | 5.3 |
| | 4-9 | Resist 2-9 | 85 | 118 | 5.6 |
| | 4-10 | Resist 2-10 | 85 | 120 | 5.0 |
| | 4-11 | Resist 2-11 | 85 | 120 | 4.1 |
| | 4-12 | Resist 2-12 | 85 | 110 | 5.1 |
| | 4-13 | Resist 2-13 | 85 | 120 | 5.1 |
| | 4-14 | Resist 2-14 | 85 | 110 | 5.2 |
| | 4-15 | Resist 2-15 | 85 | 110 | 5.5 |
| | 4-16 | Resist 2-16 | 85 | 120 | 5.2 |
| | 4-17 | Resist 2-17 | 85 | 120 | 5.5 |
| | 4-18 | Resist 2-18 | 85 | 110 | 5.1 |
| | 4-19 | Resist 2-19 | 85 | 110 | 5.0 |
| | 4-20 | Resist 2-20 | 85 | 110 | 5.0 |

TABLE 6

| | | Resist | PEB temp. (° C.) | Sensitivity (μC/cm²) | CDU (nm) |
|---|---|---|---|---|---|
| Comparative Example | 2-1 | Comparative Resist 1 | 85 | 235 | 7.2 |
| | 2-2 | Comparative Resist 2 | 85 | 221 | 9.2 |
| | 2-3 | Comparative Resist 3 | 85 | 236 | 7.2 |

It is evident from Tables 4 to 6 that the resist compositions of Examples have a high sensitivity and a low value of CDU. The resist compositions of Comparative Examples have sensitivity and CDU values which are inferior to those of Examples. It is demonstrated that the resist composition comprising a base resin comprising acid labile group-containing recurring units and preferably acid generator-containing recurring units, and a sodium, magnesium, potassium, calcium, rubidium, strontium, yttrium, cesium, barium or cerium salt of fluorosulfonic acid having a benzene ring substituted with a plurality of iodine or bromine atoms exhibits a high resolution, a high sensitivity, and a minimal LWR. The resist composition is best suited as the resist material for VLSIs and patterning material for masks.

Japanese Patent Application No. 2017-201726 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base resin comprising recurring units having an acid labile group, and a metal salt of sulfonic acid having the formula (1):

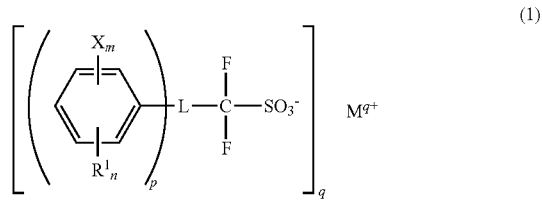

(1)

wherein X is each independently iodine or bromine,

R$^1$ is hydroxy, C$_1$-C$_{20}$ alkyl, C$_1$-C$_{20}$ alkoxy, C$_2$-C$_{20}$ acyloxy, fluorine, chlorine, amino, —NR$^2$—C(=O)—R$^3$, or —NR$^2$—C(=O)—O—R$^3$, at least one hydrogen on the alkyl, alkoxy or acyloxy group may be substituted by fluorine, chlorine, bromine, iodine, hydroxyl, amino or a C$_1$-C$_6$ alkoxy moiety, R$^2$ is a C$_1$-C$_6$ alkyl group, R$^3$ is a C$_1$-C$_{16}$ alkyl, C$_2$-C$_{16}$ alkenyl or C$_6$-C$_{12}$ aryl group in which at least one hydrogen may be substituted by a halogen, hydroxyl, C$_1$-C$_6$ alkoxy, C$_2$-C$_6$ acyl or C$_2$-C$_6$ acyloxy moiety, L is a single bond or a (p+1)-valent C$_1$-C$_{20}$ hydrocarbon group which may contain an ether bond, carbonyl, ester bond, amide bond, sultone, lactam, carbonate, halogen, hydroxyl or carboxyl moiety, M$^{q+}$ is a sodium, magnesium, potassium, calcium, rubidium, strontium, yttrium, cesium, barium or cerium ion, m is an integer of 2 to 5, n is an integer of 0 to 3, m+n is 2 to 5, p is an integer of 1 to 3, and q is an integer of 1 to 3.

2. The resist composition of claim 1 wherein the recurring units having an acid labile group have the formula (a1) or (a2):

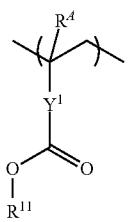

(a1)

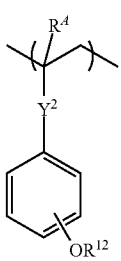

(a2)

wherein R$^A$ is each independently hydrogen or methyl, R$^{11}$ and R$^{12}$ each are an acid labile group, Y$^1$ is a single bond or a C$_1$-C$_{15}$ linking group containing an ester bond, lactone ring, phenylene or naphthylene moiety, and Y$^2$ is a single bond, ester bond or amide bond.

3. The resist composition of claim 1 wherein the base resin further comprises recurring units of at least one type selected from the formulae (b1) to (b3):

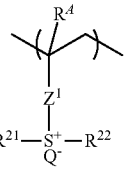

(b1)

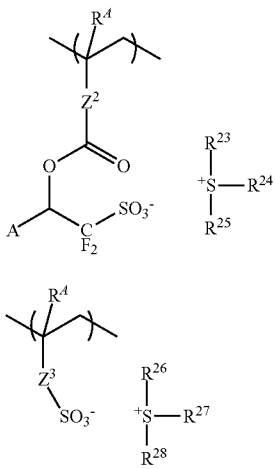

wherein $R^A$ is each independently hydrogen or methyl,
$Z^1$ is a single bond, phenylene group, —O—$Z^{11}$—, —C(=O)—O—$Z^{11}$—, or —C(=O)—NH—$Z^{11}$—,
$Z^2$ is a single bond, —C(=O)—O—$Z^{11}$—, or —C(=O)—NH—$Z^{11}$—,
$Z^3$ is a single bond, methylene, ethylene, phenylene, fluorinated phenylene, —O—$Z^{11}$—, —C(=O)—O—$Z^{11}$—, or —C(=O)—NH—$Z^{11}$—,
$Z^{11}$ is a $C_1$-$C_6$ alkanediyl group, phenylene group, or $C_2$-$C_{10}$ alkenediyl group, which may contain a carbonyl, ester bond, ether bond or hydroxyl moiety,
$R^{21}$ to $R^{28}$ are each independently a $C_1$-$C_{22}$ monovalent hydrocarbon group which may contain a heteroatom, a pair of $R^{21}$ and $R^{22}$ may bond together to form a ring with the sulfur atom to which they are attached, any two of $R^{23}$, $R^{24}$ and $R^{25}$ or any two of $R^{26}$, $R^{27}$ and $R^{28}$ may bond together to form a ring with the sulfur atom to which they are attached,
A is hydrogen or trifluoromethyl, and
$Q^-$ is a non-nucleophilic counter ion.

4. The resist composition of claim 3 wherein the base resin comprises recurring units of formula (b2).

5. The resist composition of claim 1 which is a chemically amplified positive resist composition.

6. The resist composition of claim 1, further comprising an organic solvent.

7. The resist composition of claim 1, further comprising an acid generator.

8. The resist composition of claim 1, further comprising a quencher.

9. The resist composition of claim 1, further comprising a surfactant.

10. A process for forming a pattern comprising the steps of applying the resist composition of claim 1 onto a substrate, baking to form a resist film, exposing the resist film to high-energy radiation, and developing the exposed film in a developer.

11. The process of claim 10 wherein the high-energy radiation is EUV of wavelength 3 to 15 nm.

12. The process of claim 10 wherein the high-energy radiation is EB emitted at an accelerating voltage of 1 to 150 kV.

13. The process of claim 11 wherein during the exposure step, the surface of the substrate underlying the resist film is electrically chained positive.

14. A barium salt having the formula (2):

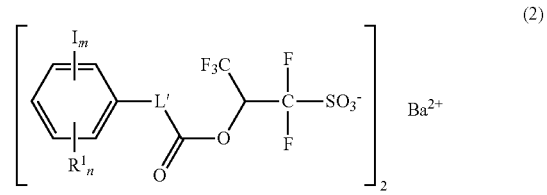

wherein $R^1$ is hydroxy, $C_1$-$C_{20}$ alkyl, $C_1$-$C_{20}$ alkoxy, $C_2$-$C_{20}$ acyloxy, fluorine, chlorine, amino, —$NR^2$—C(=O)—$R^3$, or —$NR^2$—C(=O)—O—$R^3$, at least one hydrogen on the alkyl, alkoxy or acyloxy group may be substituted by fluorine, chlorine, bromine, iodine, hydroxyl, amino or a $C_1$-$C_6$ alkoxy moiety,
$R^2$ is a $C_1$-$C_6$ alkyl group,
$R^3$ is a $C_1$-$C_{16}$ alkyl, $C_2$-$C_{16}$ alkenyl or $C_1$-$C_{12}$ aryl group in which at least one hydrogen may be substituted by a halogen, hydroxyl, $C_1$-$C_6$ alkoxy, $C_2$-$C_6$ acyl or $C_2$-$C_6$ acyloxy moiety,
L' is a single bond, or a $C_1$-$C_{12}$ alkanediyl, $C_2$-$C_{12}$ alkenediyl or $C_6$-$C_{10}$ arylene group which may contain an ether bond, carbonyl, ester bond,
m is an integer of 2 to 5, n is an integer of 0 to 3, m+n is 2 to 5.

* * * * *